(12) United States Patent
Gallagher et al.

(10) Patent No.: US 9,868,776 B2
(45) Date of Patent: *Jan. 16, 2018

(54) ANTI-SENSE OLIGONUCLEOTIDES TARGETED AGAINST EXON 9 OF IL-23R-ALPHA GENE AND METHOD OF USING SAME TO INDUCE EXON SKIPPING AND TO TREAT INFLAMMATORY BOWEL DISEASES

(71) Applicants: Grant Gallagher, Milltown, NJ (US); Raymond Yu, East Brunswick, NJ (US); Jonathan Brazaitis, Parlin, NJ (US)

(72) Inventors: Grant Gallagher, Milltown, NJ (US); Raymond Yu, East Brunswick, NJ (US); Jonathan Brazaitis, Parlin, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 169 days.

This patent is subject to a terminal disclaimer.

(21) Appl. No.: 14/918,657

(22) Filed: Oct. 21, 2015

(65) Prior Publication Data

US 2016/0115218 A1 Apr. 28, 2016

Related U.S. Application Data

(63) Continuation of application No. 14/088,553, filed on Nov. 25, 2013, now Pat. No. 9,187,750, which is a continuation of application No. 13/068,064, filed on May 2, 2011, now Pat. No. 8,618,070.

(60) Provisional application No. 61/343,615, filed on Apr. 30, 2010.

(51) Int. Cl.
| | |
|---|---|
| *C12N 15/11* | (2006.01) |
| *C07K 14/715* | (2006.01) |
| *C12N 15/113* | (2010.01) |
| *A61K 31/7088* | (2006.01) |

(52) U.S. Cl.
CPC ...... *C07K 14/7155* (2013.01); *A61K 31/7088* (2013.01); *C12N 15/113* (2013.01); *C12N 15/1138* (2013.01); *C12N 2310/11* (2013.01); *C12N 2310/14* (2013.01); *C12N 2310/315* (2013.01); *C12N 2310/321* (2013.01); *C12N 2320/33* (2013.01)

(58) Field of Classification Search
None
See application file for complete search history.

(56) References Cited

PUBLICATIONS

Dubinsky, M. C. et al. IL-23 receptor (IL-23R) gene protect against pediatric Crohn's disease. Inflamm Bowel Dis 13, 511-515 (2007).

Duerr, R. H. et al. A genome-wide association study identifies IL23R as an inflammatory bowel disease gene. Science 314, 1461-1463 (2006).

Newman W. G., Zhang, Q., Liu, X., Amos, C.I. & Siminovitch, K.A. Genetic variants in IL-23R and ATG16L1 independently predispose to increased susceptibility to Crohn's disease in Canadian population. J Clin Gastroenterol 43,444-447 (2009).

McKenzie, B. S., Kastelein, R. A. & Cua, D. J. Understanding the IL-23-1L-17 immune pathway. Trends Immunol 27, 17-23 (2006).

De Paus, R. A, Van De Wetering, D., Van Dissel, J. T. & Van De Vosse, E. IL-23 and IL-12 responses in activated human T cells retrovirally transduced with IL-23 receptor variants. Mol. Immunol 45, 3889-3895 (2008).

Kan, S. H., Mancini, G. & Gallagher, G. Identification and characterization of multiple splice forms of the human interleukin-23 receptor alpha chain in mitogenactivated leukocytes. Genes Immun. 9, 631-639 (2008).

Mancini, G., Kan, S. H. & Gallagher, G. A novel insertion variant of the human IL-23 receptor-alpha chain transcript. Genes Immun 9, 566-569 (2008).

Cooper, T. A. & Mattox, W. The regulation of splice-site selection, and its role in human disease. Am J Hum Genet 61, 259-266 (1997).

Watakabe, A., Tanaka, K. & Shimura, Y. The role of exon sequences in splice site selection. Genes Dev 7, 407-418 (1993).

Woodley, L & Valcarcel, J. Regulation of alternative pre-mRNA splicing. Brief Funct Genomic Proteomic 1, 266-277 (2002).

Lin, S. & Fu, X. D. SR proteins and related factors in alternative splicing. Adv Exp Med Biol 623, 107-122 (2007).

Shiga, N. et al. Disruption of the splicing enhancer sequence within exon 27 55 of the dystrophin gene by a nonsense mutation induces partial skipping of the exon and is responsible for Becker muscular dystrophy. J Clin Invest 100, 2204-2210 (1997).

Vuillaumier-Barrot, S. et al. Characterization of the 415G>A (E139K) PMM2 mutation in carbohydrate-deficient glycoprotein syndrome type la disrupting a splicing enhancer resulting in exon 5 skipping. Hum Mutat 14, 543-544 (1999).

Long, J. C. & Caceres, J. F. The SR protein family of splicing factors: master regulators of gene expression. Biochem J 417, 15-27 (2009).

Cua, D. J. et al. Interleukin-23 rather than interleukin-12 is the critical cytokine for autoimmune inflammation of the grain. Nature 421, 744-748 (2003).

Langrish, C. L. et al. IL-23 drives a pathogenic T cell population that induces autoimmune inflammation. J Exp Med 201, 233-240 (2005).

*Primary Examiner* — Ekaterina Poliakova-Georgantas
(74) *Attorney, Agent, or Firm* — Terence J. Bogie; Jessica Downing

(57) ABSTRACT

The present invention relates to anti-sense oligonucleotides (AONs) used to induce exon 9 skipping in IL-23Rα gene. Exon 9 skipping of the IL23Rα gene ultimately causes specific induction of a novel soluble truncated IL-23Rα (Δ9) protein, characterized by a lack in a transmembrane domain and has a unique eight (8) amino acids (GLKEGSYC) at its C-terminus end as a result of frame-shift. The present invention provides a utility application of the use of AONs to induce production of a Δ9 protein which inhibits IL-23R-mediated cell signaling. More particularly, Δ9 protein blocks STAT3 formation as well as Th17 maturation. There is provided a therapeutic application of AONs in treating a mammal such as a human patient inflicted with Crohn's disease.

9 Claims, 38 Drawing Sheets

Figure 3B

Exon 8 and 5' end of intron 8

```
1   TTCCCCAGGTCACATCAAAAGCATTCCAACATGACACATGGAATTCTGGG
51  CTAACAGTTGCTTCCATCTCTACAGGGCACCTTACTTCTGGTAAGAAAAT
101 ACAACTTAGGCTTTTTGAGTAGTCTTTTAGTAATTGCCCATTTTAACCCA
151 TCATACTGAAAAAATCACATCAGGTGTTAAGTTTCTGGACAATAAGATAT
201 GCCTTATGTCTTCCATAGGAAAATAATAGACAAAGTACAAAGATCTGCTT
251 AAAACTGAATGTAAGAAGTGGCTTAGGTGGATTTTGCCGGCTTTTGCAAT
301 AGATTGTATACATTTTTTAAAATTTTTATTTATTTTATTTTATTTTTTGA
351 GACGAAGCCTTGTTCTGTCACCCAGGCTGGAGTGCAATGGTGCAATCTCG
401 GCTCACTGCAACCTCCGCCTCCCAGGTTCAAGCGATTCTGCTGCCTCAGC
451 CTTCTGAGTAGCTGGGATTACAGGCATCCGCCATCACGCCCAGCTAATTT
501 TT
```

Figure 3C

3' end of intron 8, exon 9 and 5' end of intron 9

```
1   CCTGTGTCAGACAAGCCAAATGAAGCTCACCACTAAGAATTTATACGAAA
51  TTTGCATGCACAAGCCGACCACATTTGCCAGAGATGCACTTCTAAAAACC
101 CACTGACATCAGATACATGTAGCCCAACTTTCTCAAACAAAAAGTTGTTT
151 CCTGGGGTAGTTGTGCACTCTGGAAAAACAGTCACTCTGTGGCCTAAAGT
201 AAAGGTTAATTTTGCTTCCCCCACCCTTTCTCCTTTGAGACCTTTGCTT
251 TGAGCAGAGTAAAGAGAATAGTAATTCTGGTATCAAATGAAGACTAATGC
301 TTGGTTAAAATTATTTTTCTTTCCTTTCATTAGACAACAGAGGAGACATT
351 GGACTTTTATTGGGAATGATCGTCTTTGCTGTTATGTTGTCAATTCTTTC
401 TTTGATTGGGATATTTAACAGATCATTCCGAACTGGGTAGGTTTTGCAG
451 AATTTCTGTTTTCTGATTTAGACTACATGTATATGTATCACCAAAATTTA
501 GTCATTTCAGTTGTTTACTAGAAAAATCTGTTAACATTTTTATTCAGATA
551 AAGGAAAATAAAAAGAACAATGTTTAATAAGTACTTACCCATGCCAAACT
601 CTCTACAAATGTCTTTCCTTTAATCCTCAAAATGACCCTGCCAGAAAAGC
651 TTCCTGGCCTATTTTACAGGTGACTTAAATGAGGCTTAAAGAGGCTAAGT
701 CCTCAGCCCAGAATCACTGAACAGTAAGCCCTGAGTCCAAACACAGCTGA
751 TATCAAAGCCCATTTCTCTCCTTTACTACACGGCGTTTTCCATTGTGCCT
801 CAAATTTACCTACAGTGCCTAGATTCTTGAGAGTGGTGAAGTCACAAATT
851 GCCTTGTGTTAAAAGAAAAACTTCAGCCAAATTAAATTTAAAGGAGTTTA
901 ATTGAGCAATGAATGTGCGAATTGGGCAGCCCCCAGAATTACAGCAGATT
951 CAGAAAGACTCCAGGGTTGCCTT
```

Figure 3D

3' end of intron 9 and exon 10

```
1   TCTGTTGCCCAGAGTGAGTGCAGTGGCATGGTCACAGCTCACTACAGCCT
51  TGACCTCCCAGGCTCAAGCGATCTTTCCACCTCAGCCTCCCAAGTAGCTG
101 GGACCACAGGCATGCACCACCACACCCAGCTAATTTTTTAATATTCTGTA
151 GAGACAGGGTCTTGCTATGTTGCCCAGGCTGGTCTCGAACTCCTGGACTC
201 AAGCAATCCTCCCACCTCAGCCTCCCAAAGTGCTGGGATTACAGGCATGA
251 GCCACTGTGCCCGACCTAGGAAATTTGATTTTTAATATACATTTTATTCT
301 AGTTGACTTCCTAATCTCCTATATGATTGCCTGCTTCTTCTAACGTGTCA
351 TTTTTGTTTTTTAGGATTAAAAGAAGGATCTTATTGTTAATACCAAAGTG
401 GCTTTATGAAGATATTCCTAATATGAAAACAGCAATGTTGTGAAAATGC
451 TACAG
```

Figure 8B

>Nucleotide
ATGAATCAGGTCACTATTCAATGGGATGCAGTAATAGCCCTTTACATACTCTTCA
GCTGGTGTCATGGAGGAATTACAAATATAAACTGCTCTGGCCACATCTGGGTAGA
ACCAGCCACAATTTTTAAGATGGGTATGAATATCTCTATATATTGCCAAGCAGCA
ATTAAGAACTGCCAACCAAGGAAACTTCATTTTTATAAAAATGGCATCAAAGAAA
GATTTCAAATCACAAGGATTAATAAAACAACAGCTCGGCTTTGGTATAAAAACTT
TCTGGAACCACATGCTTCTATGTACTGCACTGCTGAATGTCCCAAACATTTTCAA
GAGACACTGATATGTGGAAAAGACATTTCTTCTGGATATCCGCCAGATATTCCTG
ATGAAGTAACCTGTGTCATTTATGAATATTCAGGCAACATGACTTGCACCTGGAA
TGCTGGGAAGCTCACCTACATAGACACAAAATACGTGGTACATGTGAAGAGTTTA
GAGACAGAAGAAGAGCAACAGTATCTCACCTCAAGCTATATTAACATCTCCACTG
ATTCATTACAAGGTGGCAAGAAGTACTTGGTTTGGGTCCAAGCAGCAAACGCACT
AGGCATGGAAGAGTCAAAACAACTGCAAATTCACCTGGATGATATAGTGATACCT
TCTGCAGCCGTCATTTCCAGGGCTGAGACTATAAATGCTACAGTGCCCAAGACCA
TAATTTATTGGGATAGTCAAACAACAATTGAAAAGGTTTCCTGTGAAATGAGATA
CAAGGCTACAACAAACCAAACTTGGAATGTTAAAGAATTTGACACCAATTTTACA
TATGTGCAACAGTCAGAATTCTACTTGGAGCCAAACATTAAGTACGTATTTCAAG
TGAGATGTCAAGAAACAGGCAAAAGGTACTGGCAGCCTTGGAGTTCACTGTTTTT
TCATAAAACACCTGAAACAGTTCCCCAGGTCACATCAAAAGCATTCCAACATGAC
ACATGGAATTCTGGGCTAACAGTTGCTTCCATCTCTACAGGGCACCTTACTTCTG
GATTAAAAGAAGGATCTTATTGTTAA >Protein
Δ9
MNQVTIQWDAVIALYILFSWCHGGITNINCSGHIWVEPATIFKMGMNISIYCQAAI
KNCQPRKLHFYKNGIKERFQITRINKTTARLWYKNFLEPHASMYCTAECPKHFQ
ETLICGKDISSGYPPDIPDEVTCVIYEYSGNMTCTWNAGKLTYIDTKYVVHVKSL
ETEEEQQYLTSSYINISTDSLQGGKKYLVWVQAANALGMEESKQLQIHLDDIVIP
SAAVISRAETINATVPKTIIYWDSQTTIEKVSCEMRYKATTNQTWNVKEFDTNFT
YVQQSEFYLEPNIKYVFQVRCQETGKRYWQPWSSLFFHKTPETVPQVTSKAFQH
DTWNSGLTVASISTGHLTS<u>GLKEGSYC</u>

Figure 8C

```
                         Signal peptide         Cleavage site
SEQ ID NO: 41  Wild-type  MNQVTIQWDA VIALYILFSW CHG|GITNINC SGHIWVEPAT IFKMGMNISI
SEQ ID NO: 5   Δ9        MNQVTIQWDA VIALYILFSW CHG|GITNINC SGHIWVEPAT IFKMGMNISI Wild-type  YCQAAIKNCQ PRKLHFYKNG IKERFQITRI NKTTARLWYK NFLEPHASMY
               Δ9        YCQAAIKNCQ PRKLHFYKNG IKERFQITRI NKTTARLWYK NFLEPHASMY Wild-type  CTAECPKHFQ ETLICGKDIS SGYPPDIPDE VTCVIYEYSG NMTCTWNAGK
               Δ9        CTAECPKHFQ ETLICGKDIS SGYPPDIPDE VTCVIYEYSG NMTCTWNAGK Wild-type  LTYIDTKYVV HVKSLETEEE QQYLTSSYIN ISTDSLQGGK KYLVWVQAAN
               Δ9        LTYIDTKYVV HVKSLETEEE QQYLTSSYIN ISTDSLQGGK KYLVWVQAAN Wild-type  ALGMEESKQL QIHLDDIVIP SAAVISRAET INATVPKTII YWDSQTTIEK
               Δ9        ALGMEESKQL QIHLDDIVIP SAAVISRAET INATVPKTII YWDSQTTIEK Wild-type  VSCEMRYKAT TNQTWNVKEF DTNFTYVQQS EFYLEPNIKY VFQVRCQETG
               Δ9        VSCEMRYKAT TNQTWNVKEF DTNFTYVQQS EFYLEPNIKY VFQVRCQETG Wild-type  KRYWQPWSSL FFHKTPETVP QVTSKAFQHD TWNSGLTVAS ISTGHLTSDN
               Δ9        KRYWQPWSSL FFHKTPETVP QVTSKAFQHD TWNSGLTVAS ISTGHLTS--

Transmembrane domain
               Wild-type  RGD|GLLLGM IVFAVMLSIL SLIGIF|NRSF RTGIKRRILL LIPKWLYEDI
               Δ9        --- -------- ---------- -------- ---------- ----------

Wild-type  PNMKNSNVVK MLQENSELMN NNSSEQVLYV DPMITEIKEI FIPEHKPTDY
               Δ9        ---------- ---------- ---------- ---------- ----------

Wild-type  KKENTGPLET RDYPQNSLFD NTTVVYIPDL NTGYKPQISN FLPEGSHLSN
               Δ9        ---------- ---------- ---------- ---------- ----------

Wild-type  NNEITSLTLK PPVDSLDSGN NPRLQKHPNF AFSVSSVNSL SNTIFLGELS
               Δ9        ---------- ---------- ---------- ---------- ----------

Wild-type  LILNQGECSS PDIQNSVEEE TTMLLENDSP SETIPEQTLL PDEFVSCLGI
               Δ9        ---------- ---------- ---------- ---------- ----------

Wild-type  VNEELPSINT YFPQNILESH FNRISLLEK- --------
               Δ9        ---------- ---------- ---------G LKEGSYC
                                                       Extra 8 amino acids
                                                       SEQ ID NO: 42
```

Figure 10A

```
>SF2 coding sequence
ATGTCGGGAGGTGGTGTGATTCGTGGCCCCGCAGGGAACAACGATTGCCGCATCTACGTGGGTAACTTAC
CTCCAGACATCCGAACCAAGGACATTGAGGACGTGTTCTACAAATACGGCGCTATCCGCGACATCGACCT
CAAGAATCGCCGCGGGGGACCGCCCTTCGCCTTCGTTGAGTTCGAGGACCCGCGAGACGCGGAAGACGCG
GTGTATGGTCGCGACGGCTATGATTACGATGGGTACCGTCTGCGGGTGGAGTTTCCTCGAAGCGGCCGTG
GAACAGGCCGAGGCGGCGGCGGGGGTGGAGGTGGCGGAGCTCCCCGAGGTCGCTATGGCCCCCCATCCAG
GCGGTCTGAAAACAGAGTGGTTGTCTCTGGACTGCCTCCAAGTGGAAGTTGGCAGGATTTAAAGGATCAC
ATGCGTGAAGCAGGTGATGTATGTTATGCTGATGTTTACCGAGATGGCACTGGTGTCGTGGAGTTTGTAC
GGAAAGAAGATATGACCTATGCAGTTCGAAAACTGGATAACACTAAGTTTAGATCTCATGAGGGAGAAAC
TGCCTACATCCGGGTTAAAGTTGATGGGCCCAGAAGTCCAAGTTATGGAAGATCTCGATCTCGAAGCCGT
AGTCGTAGCAGAAGCCGTAGCAGAAGCAACAGCAGGAGTCGCAGTTACTCCCCAAGGAGAAGCAGAGGAT
CACCACGCTATTCTCCCCGTCATAGCAGATCTCGCTCTCGTACATAA >SF2 amino acid sequence
MSGGGVIRGPAGNNDCRIYVGNLPPDIRTKDIEDVFYKYGAIRDIDLKNRRGGPP
FAFVEFEDPRDAEDAVYGRDGYDYDGYRLRVEFPRSGRGTGRGGGGGGGGAPRG
RYGPPSRRSENRVVVSGLPPSGSWQDLKDHMREAGDVCYADVYRDGTGVVEFVRK
EDMTYAVRKLDNTKFRSHEGETAYIRVKVDGPRSPSYGRSRSRSRSRSRSRSRSN
SRSRSYSPRRSRGSPRYSPRHSRSRSRT
```

Figure 10B

```
>SRp40 coding sequence
atgagtggctgtcgggtattcatcgggagactaaatccagcggccagggagaaggacgtg
gaaagattcttcaagggatatggacggataagagatattgatctgaaaagaggctttggt
tttgtggaatttgaggatccaagggatgcagatgatgctgtgtatgagcttgatggaaaa
gaactctgtagtgaaagggttactattgaacatgctagggctcggtcacgaggtggaaga
ggtagaggacgatactctgaccgttttagtagtcgcagacctcgaaatgatagacgaaat
gctccacctgtaagaacagaaaatcgtcttatagttgagaatttatcctcaagagtcagc
tggcaggatctcaaagatttcatgagacaagctggggaagtaacgtttgcggatgcacac
cgacctaaattaaatgaaggggtggttgagtttgcctcttatggtgacttaaagaatgct
attgaaaaactttctggaaaggaaataaatgggagaaaaataaaattaattgaaggcagc
aaaaggcacagtaggtcaagaagcaggtctcgatcccggaccagaagttcctctaggtct
cgtagccgatcccgttccgtagtcgcaaatcttacagccggtcaagaagcaggagcagg
agccggagccggagcaagtcccgttctgttagtaggtctcccgtgcctgagaagagccag
aaacgtggttcttcaagtagatctaagtctccagcatctgtggatcgccagaggtcccgg
tcccgatcaaggtccagatcagttgacagtggcaattaaactgtaaataa
```

```
>SRp40 amino acid sequence
MSGCRVFIGRLNPAAREKDVERFFKGYGRIRDIDLKRGFGFVEFEDPRDADDAVY
ELDGKELCSERVTIEHARARSRGGRGRGRYSDRFSSRRPRNDRRNAPPVRTENRL
IVENLSSRVSWQDLKDFMRQAGEVTFADAHRPKLNEGVVEFASYGDLKNAIEKLS
GKEINGRKIKLIEGSKRHSRSRSRSRSRTRSSSRSRSRSRSRSRKSYSRSRSRSR
SRSRSKSRSVSRSPVPEKSQKRGSSSRSKSPASVDRQRSRSRSRSRSVDSGN
```

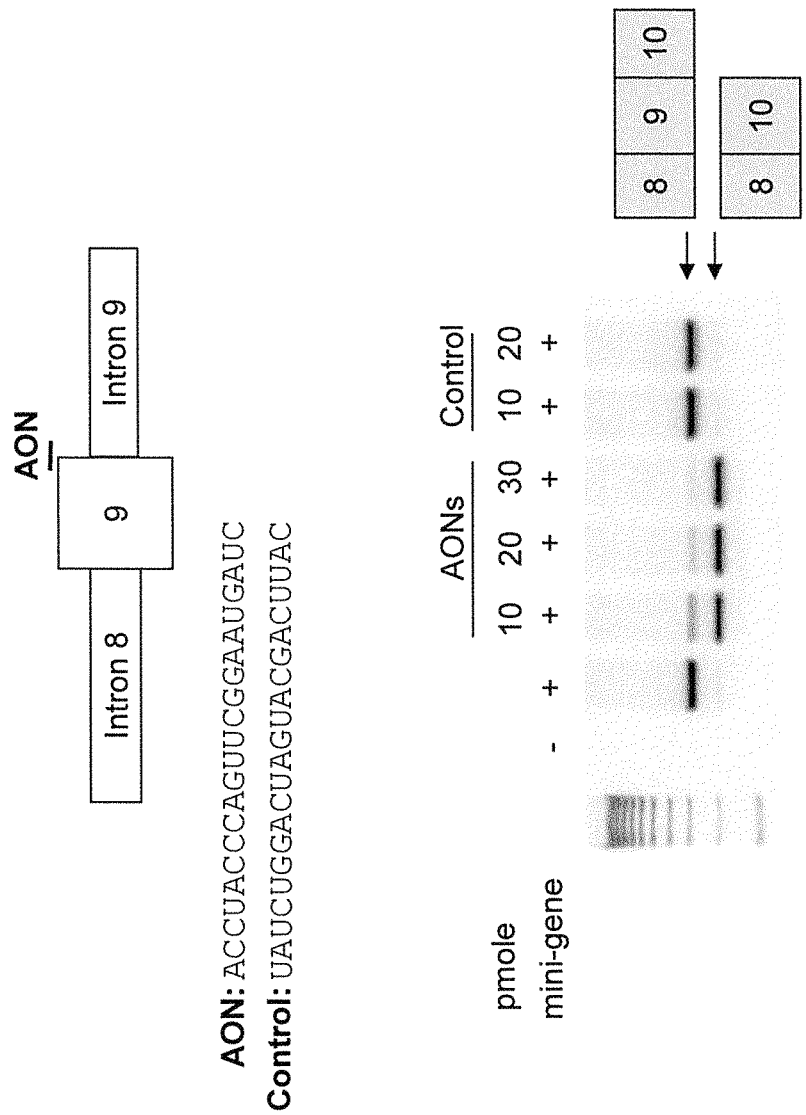

Figure 23
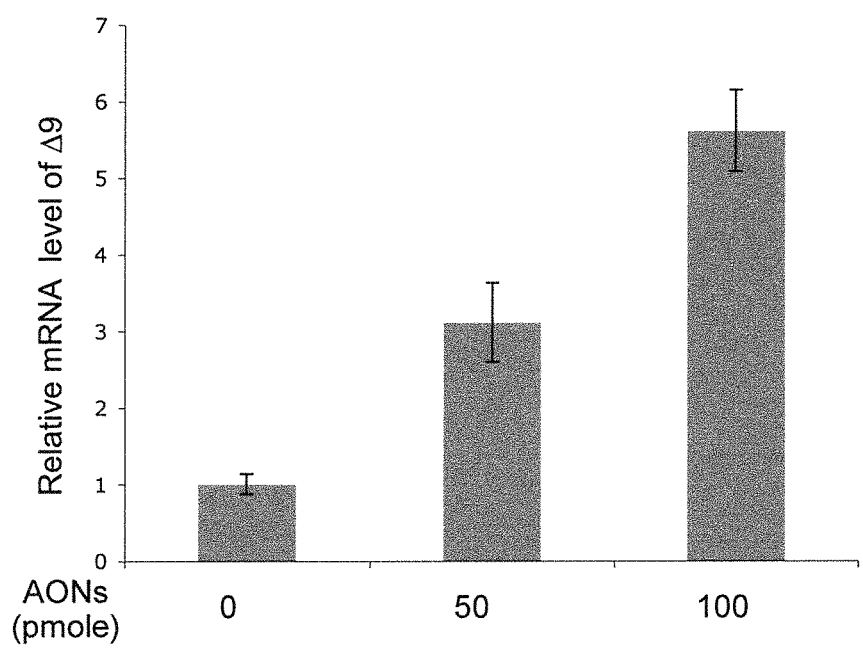
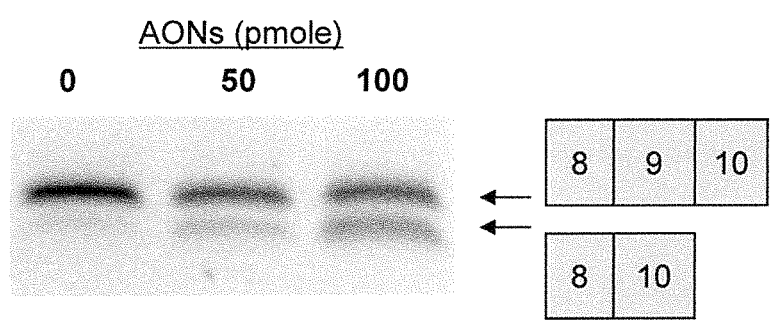

SEQUENCE LISTING

```
<160> NUMBER OF SEQ ID NOS: 50

<210> SEQ ID NO 1
<211> LENGTH: 502
<212> TYPE: DNA
<213> ORGANISM: Homo sapiens

<400> SEQUENCE: 1
ttccccaggt cacatcaaaa gcattccaac atgacacatg gaattctggg ctaacagttg      60
cttccatctc tacagggcac cttacttctg gtaagaaaat acaacttagg cttttttgagt    120 agtcttttag taattgccca ttttaaccca tcatactgaa aaaatcacat caggtgttaa    180
gtttctggac aataagatat gccttatgtc ttccatagga aaataataga caaagtacaa    240
agatctgctt aaaactgaat gtaagaagtg gcttaggtgg attttgccgg cttttgcaat    300
agattgtata catttttaa aattttatt tattttattt tatttttga gacgaagcct       360 tgttctgtca cccaggctgg agtgcaatgg tgcaatctcg gctcactgca acctccgcct    420
cccaggttca gcgattctg ctgcctcagc cttctgagta gctgggatta caggcatccg     480
ccatcacgcc cagctaattt tt                                              502

<210> SEQ ID NO 2
<211> LENGTH: 973
<212> TYPE: DNA
<213> ORGANISM: Homo sapiens

<400> SEQUENCE: 2
cctgtgtcag acaagccaaa tgaagctcac cactaagaat ttatacgaaa tttgcatgca      60
caagccgacc acatttgcca gagatgcact tctaaaaacc cactgacatc agatacatgt    120
agcccaactt tctcaaacaa aaagttgttt cctggggtag ttgtgcactc tggaaaaaca    180
gtcactctgt ggcctaaagt aaaggttaat tttgcttccc cccacccttt ctcctttgag    240
acctttgctt tgagcagagt aaagagaata gtaattctgg tatcaaatga agactaatgc    300
```

```
ttggttaaaa ttattttcct ttcctttcat tagacaacag aggagacatt ggactttat      360 tgggaatgat cgtctttgct gttatgttgt caattctttc tttgattggg atatttaaca     420
gatcattccg aactgggtag gttttttgcag aatttctgtt ttctgattta gactacatgt    480
atatgtatca ccaaaattta gtcatttcag ttgtttacta gaaaaatctg ttaacatttt     540
tattcagata aaggaaaata aaaagaacaa tgtttaataa gtacttaccc atgccaaact     600
ctctacaaat gtctttcctt taatcctcaa aatgaccctg ccagaaaagc ttcctggcct     660
attttacagg tgacttaaat gaggcttaaa gaggctaagt cctcagccca gaatcactga     720
acagtaagcc ctgagtccaa acacagctga tatcaaagcc catttctctc ctttactaca     780
cggcgttttc cattgtgcct caaatttacc tacagtgcct agattcttga gagtggtgaa     840
gtcacaaatt gccttgtgtt aaaagaaaaa cttcagccaa attaaattta aaggagttta    900
attgagcaat gaatgtgcga attgggcagc ccccagaatt acagcagatt cagaaagact     960
ccagggttgc ctt                                                        973
```

```
<210> SEQ ID NO 3
<211> LENGTH: 455
<212> TYPE: DNA
<213> ORGANISM: Homo sapiens

<400> SEQUENCE: 3
tctgttgccc agagtgagtg cagtggcatg gtcacagctc actacagcct tgacctccca     60
ggctcaagcg atcttccac ctcagcctcc caagtagctg ggaccacagg catgcaccac     120
cacacccagc taattttta atattctgta gagacagggt cttgctatgt tgcccaggct    180
ggtctcgaac tcctggactc aagcaatcct cccacctcag cctcccaaag tgctgggatt    240
acaggcatga gccactgtgc ccgacctagg aaatttgatt tttaatatac attttattct    300
agttgacttc ctaatctcct atatgattgc ctgcttcttc taacgtgtca ttttgtttt     360 ttaggattaa aagaaggatc ttattgttaa taccaaagtg gctttatgaa gatattccta    420
atatgaaaaa cagcaatgtt gtgaaaatgc tacag                                455
```

```
<210> SEQ ID NO 4
<211> LENGTH: 1071
<212> TYPE: DNA
<213> ORGANISM: Homo sapiens

<400> SEQUENCE: 4
atgaatcagg tcactattca atgggatgca gtaatagccc tttacatact cttcagctgg    60
tgtcatggag gaattacaaa tataaactgc tctggccaca tctgggtaga accagccaca    120
atttttaaga tgggtatgaa tatctctata tattgccaag cagcaattaa gaactgccaa    180
ccaaggaaac ttcattttta taaaaatggc atcaaagaaa gatttcaaat cacaaggatt    240
aataaaacaa cagctcggct ttggtataaa aactttctgg aaccacatgc ttctatgtac    300
tgcactgctg aatgtcccaa acattttcaa gagacactga tatgtggaaa agacatttct    360
tctggatatc cgccagatat tcctgatgaa gtaacctgtg tcatttatga atattcaggc    420
aacatgactt gcacctggaa tgctgggaag ctcacctaca gacacaaa atacgtggta    480 catgtgaaga gtttagagac agaagaagag caacagtatc tcacctcaag ctatattaac    540
atctccactg attcattaca aggtggcaag aagtacttgg tttgggtcca agcagcaaac    600
gcactaggca tggaagagtc aaaacaactg caaattcacc tggatgatat agtgataccg    660
```

```
tctgcagccg tcatttccag ggctgagact ataaatgcta cagtgcccaa gaccataatt    720
tattgggata gtcaaacaac aattgaaaag gtttcctgtg aaatgagata caaggctaca    780
acaaaccaaa cttggaatgt taagaatttg acaccaatt ttacatatgt gcaacagtca     840
gaattctact tggagccaaa cattaagtac gtatttcaag tgagatgtca agaaacaggc    900
aaaaggtact ggcagccttg gagttcactg ttttttcata aacacctgaa acagttccc    960
caggtcacat caaaagcatt ccaacatgac acatggaatt ctgggctaac agttgcttcc   1020
atctctacag ggcaccttac ttctggatta aagaaggat cttattgtta a            1071

<210> SEQ ID NO 5
<211> LENGTH: 356
<212> TYPE: PRT
<213> ORGANISM: Homo sapiens

<400> SEQUENCE: 5

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
                20                  25                  30

His Ile Trp Val Glu Pro Ala Thr Ile Phe Lys Met Gly Met Asn Ile
            35                  40                  45

Ser Ile Tyr Cys Gln Ala Ala Ile Lys Asn Cys Gln Pro Arg Lys Leu
        50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser Ser
                165                 170                 175

Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300
```

```
Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
            325                 330                 335

Thr Val Ala Ser Ile Ser Thr Gly His Leu Thr Ser Gly Leu Lys Glu
            340                 345                 350

Gly Ser Tyr Cys
        355

<210> SEQ ID NO 6
<211> LENGTH: 747
<212> TYPE: DNA
<213> ORGANISM: Homo sapiens

<400> SEQUENCE: 6
atgtcgggag gtggtgtgat tcgtggcccc gcaggaaca acgattgccg catctacgtg      60
ggtaacttac ctccagacat ccgaaccaag gacattgagg acgtgttcta caaatacggc    120
gctatccgcg acatcgacct caagaatcgc cgcggggac cgcccttcgc cttcgttgag     180
ttcgaggacc cgcgagacgc ggaagacgcg gtgtatggtc gcgacggcta tgattacgat    240
gggtaccgtc tgcgggtgga gtttcctcga agcggccgtg aacaggccg aggcggcggc     300 ggggtggag gtggcggagc tccccgaggt cgctatggcc ccccatccag gcggtctgaa    360
aacagagtgg ttgtctctgg actgcctcca agtggaagtt ggcaggattt aaaggatcac    420
atgcgtgaag caggtgatgt atgttatgct gatgtttacc gagatggcac tggtgtcgtg    480
gagtttgtac ggaaagaaga tatgacctat gcagttcgaa aactggataa cactaagttt    540
agatctcatg agggagaaac tgcctacatc cgggttaaag ttgatgggcc agaagtcca    600 agttatggaa gatctcgatc tcgaagccgt agtcgtagca aagccgtag cagaagcaac    660 agcaggagtc gcagttactc cccaaggaga agcagaggat caccacgcta ttctccccgt    720
catagcagat ctcgctctcg tacataa                                         747

<210> SEQ ID NO 7
<211> LENGTH: 248
<212> TYPE: PRT
<213> ORGANISM: Homo sapiens

<400> SEQUENCE: 7

Met Ser Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
    50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Arg Ser Gly Arg Gly Thr Gly
            85                  90                  95

Arg Gly Gly Gly Gly Gly Gly Gly Gly Ala Pro Arg Gly Arg Tyr
            100                 105                 110

Gly Pro Pro Ser Arg Arg Ser Glu Asn Arg Val Val Ser Gly Leu
        115                 120                 125

Pro Pro Ser Gly Ser Trp Gln Asp Leu Lys Asp His Met Arg Glu Ala
```

```
              130                 135                 140
Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Glu Thr Ala Tyr Ile Arg Val
            180                 185                 190

Lys Val Asp Gly Pro Arg Ser Pro Ser Tyr Gly Arg Ser Arg Ser Arg
                195                 200                 205

Ser Arg Ser Arg Ser Arg Ser Arg Ser Asn Ser Arg Ser Arg
            210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
                245

<210> SEQ ID NO 8
<211> LENGTH: 830
<212> TYPE: DNA
<213> ORGANISM: Homo sapiens

<400> SEQUENCE: 8
atgagtggct gtcgggtatt catcgggaga ctaaatccag cggccaggga gaaggacgtg      60
gaaagattct tcaagggata tggacggata agagatattg atctgaaaag aggctttggt     120
tttgtggaat tgaggatcc aagggatgca atgatgctg tgtatgagct tgatggaaaa     180
gaactctgta gtgaaagggt tactattgaa catgctaggg ctcggtcacg aggtggaaga     240
ggtagaggac gatactctga ccgttttagt agtcgcagac ctcgaaatga tagacgaaat     300
gctccacctg taagaacaga aaatcgtctt atagttgaga atttatcctc aagagtcagc     360
tggcaggatc tcaaagattt catgagacaa gctggggaag taacgtttgc ggatgcacac     420
cgacctaaat taaatgaagg ggtggttgag tttgcctctt atggtgactt aaagaatgct     480
attgaaaaac tttctggaaa ggaaataaat gggagaaaaa taaaattaat tgaaggcagc     540
aaaaggcaca gtaggtcaag aagcaggtct cgatcccgga ccagaagttc ctctaggtct     600
cgtagccgat cccgttcccg tagtcgcaaa tcttacagcc ggtcaagaag caggagcagg     660
agccggagcc ggagcaagtc ccgttctgtt agtaggtctc ccgtgcctga aagagccag     720 aaacgtggtt cttcaagtag atctaagtct ccagcatctg tggatcgcca gaggtcccgg     780
tcccgatcaa ggtccagatc agttgacagt ggcaattaaa ctgtaaataa                830

<210> SEQ ID NO 9
<211> LENGTH: 272
<212> TYPE: PRT
<213> ORGANISM: Homo sapiens

<400> SEQUENCE: 9

Met Ser Gly Cys Arg Val Phe Ile Gly Arg Leu Asn Pro Ala Ala Arg
1               5                   10                  15

Glu Lys Asp Val Glu Arg Phe Phe Lys Gly Tyr Gly Arg Ile Arg Asp
                20                  25                  30

Ile Asp Leu Lys Arg Gly Phe Gly Phe Val Glu Phe Glu Asp Pro Arg
            35                  40                  45

Asp Ala Asp Asp Ala Val Tyr Glu Leu Asp Gly Lys Glu Leu Cys Ser
        50                  55                  60
```

```
Glu Arg Val Thr Ile Glu His Ala Arg Ala Arg Ser Arg Gly Gly Arg
 65                  70                  75                  80
Gly Arg Gly Arg Tyr Ser Asp Arg Phe Ser Arg Arg Pro Arg Asn
                 85                  90                  95
Asp Arg Arg Asn Ala Pro Pro Val Arg Thr Glu Asn Arg Leu Ile Val
            100                 105                 110
Glu Asn Leu Ser Ser Arg Val Ser Trp Gln Asp Leu Lys Asp Phe Met
        115                 120                 125
Arg Gln Ala Gly Glu Val Thr Phe Ala Asp Ala His Arg Pro Lys Leu
    130                 135                 140
Asn Glu Gly Val Val Glu Phe Ala Ser Tyr Gly Asp Leu Lys Asn Ala
145                 150                 155                 160
Ile Glu Lys Leu Ser Gly Lys Glu Ile Asn Gly Arg Lys Ile Lys Leu
                165                 170                 175
Ile Glu Gly Ser Lys Arg His Ser Arg Ser Arg Ser Arg Ser Arg Ser
            180                 185                 190
Arg Thr Arg Ser Ser Ser Arg Ser Arg Ser Arg Ser Arg Ser Arg Ser
        195                 200                 205
Arg Lys Ser Tyr Ser Arg Ser Arg Ser Arg Ser Arg Ser Arg Ser Arg
    210                 215                 220
Ser Lys Ser Arg Ser Val Ser Arg Ser Pro Val Pro Glu Lys Ser Gln
225                 230                 235                 240
Lys Arg Gly Ser Ser Ser Arg Ser Lys Ser Pro Ala Ser Val Asp Arg
                245                 250                 255
Gln Arg Ser Arg Ser Arg Ser Arg Ser Arg Ser Val Asp Ser Gly Asn
            260                 265                 270
```

<210> SEQ ID NO 10
<211> LENGTH: 22
<212> TYPE: RNA
<213> ORGANISM: Homo sapiens

<400> SEQUENCE: 10
accuacccag uucggaauga uc                                          22

<210> SEQ ID NO 11
<211> LENGTH: 22
<212> TYPE: RNA
<213> ORGANISM: Homo sapiens

<400> SEQUENCE: 11
uaucuggacu aguacgacuu ac                                          22

<210> SEQ ID NO 12
<211> LENGTH: 18
<212> TYPE: RNA
<213> ORGANISM: Homo sapiens

<400> SEQUENCE: 12
cuacccaguu cggaauga                                               18

<210> SEQ ID NO 13
<211> LENGTH: 15
<212> TYPE: RNA
<213> ORGANISM: Homo sapiens

<400> SEQUENCE: 13
uacccaguuc ggaau                                                  15

```
<210> SEQ ID NO 14
<211> LENGTH: 22
<212> TYPE: DNA
<213> ORGANISM: Homo sapiens

<400> SEQUENCE: 14
atgtctcctc tgttgtctaa tg                                              22

<210> SEQ ID NO 15
<211> LENGTH: 22
<212> TYPE: DNA
<213> ORGANISM: Homo sapiens

<400> SEQUENCE: 15
taacagcaaa gacgatcatt cc                                              22

<210> SEQ ID NO 16
<211> LENGTH: 22
<212> TYPE: DNA
<213> ORGANISM: Homo sapiens

<400> SEQUENCE: 16
gaaacaactt tttgtttgag aa                                              22

<210> SEQ ID NO 17
<211> LENGTH: 22
<212> TYPE: DNA
<213> ORGANISM: Homo sapiens

<400> SEQUENCE: 17
gtttttccag agtgcacaac ta                                              22

<210> SEQ ID NO 18
<211> LENGTH: 22
<212> TYPE: DNA
<213> ORGANISM: Homo sapiens

<400> SEQUENCE: 18
acaactgaaa tgactaaatt tt                                              22

<210> SEQ ID NO 19
<211> LENGTH: 22
<212> TYPE: DNA
<213> ORGANISM: Homo sapiens

<400> SEQUENCE: 19
aaaacgccgt gtagtaaagg ag                                              22

<210> SEQ ID NO 20
<211> LENGTH: 20
<212> TYPE: DNA
<213> ORGANISM: Homo sapiens

<400> SEQUENCE: 20
tccccaggtc acatcaaaag                                                 20

<210> SEQ ID NO 21
<211> LENGTH: 22
<212> TYPE: DNA
<213> ORGANISM: Homo sapiens

<400> SEQUENCE: 21
ttcacaacat tgctgttttt ca                                              22
```

```
<210> SEQ ID NO 22
<211> LENGTH: 24
<212> TYPE: DNA
<213> ORGANISM: Homo sapiens

<400> SEQUENCE: 22
ggcaccttac ttctggatta aaag                                              24

<210> SEQ ID NO 23
<211> LENGTH: 24
<212> TYPE: DNA
<213> ORGANISM: Homo sapiens

<400> SEQUENCE: 23
ggcaccttac ttctggatta aaag                                              24

<210> SEQ ID NO 24
<211> LENGTH: 35
<212> TYPE: DNA
<213> ORGANISM: Homo sapiens

<400> SEQUENCE: 24
acaagcttgc caccatgtcg ggaggtggtg tgatt                                  35

<210> SEQ ID NO 25
<211> LENGTH: 29
<212> TYPE: DNA
<213> ORGANISM: Homo sapiens

<400> SEQUENCE: 25
atctcgagtt atgtacgaga gcgagatct                                         29

<210> SEQ ID NO 26
<211> LENGTH: 35
<212> TYPE: DNA
<213> ORGANISM: Homo sapiens

<400> SEQUENCE: 26
acaagcttgc caccatgagt ggctgtcggg tattc                                  35

<210> SEQ ID NO 27
<211> LENGTH: 29
<212> TYPE: DNA
<213> ORGANISM: Homo sapiens

<400> SEQUENCE: 27
atctcgagtt aattgccact gtcaactga                                         29

<210> SEQ ID NO 28
<211> LENGTH: 21
<212> TYPE: DNA
<213> ORGANISM: Homo sapiens

<400> SEQUENCE: 28
aggacctgct cactggaatt a                                                 21

<210> SEQ ID NO 29
<211> LENGTH: 20
<212> TYPE: DNA
<213> ORGANISM: Homo sapiens

<400> SEQUENCE: 29
```

```
agaactgcca accaaggaaa                                            20

<210> SEQ ID NO 30
<211> LENGTH: 20
<212> TYPE: DNA
<213> ORGANISM: Homo sapiens

<400> SEQUENCE: 30
taggtgagct tcccagcatt                                            20

<210> SEQ ID NO 31
<211> LENGTH: 24
<212> TYPE: DNA
<213> ORGANISM: Homo sapiens

<400> SEQUENCE: 31
ctgggaagac ctcattggtg tcac                                       24

<210> SEQ ID NO 32
<211> LENGTH: 24
<212> TYPE: DNA
<213> ORGANISM: Homo sapiens

<400> SEQUENCE: 32
cggttatgga tgttcaggtt gacc                                       24

<210> SEQ ID NO 33
<211> LENGTH: 23
<212> TYPE: DNA
<213> ORGANISM: Homo sapiens

<400> SEQUENCE: 33 cctcccctg gaattacact gtc                                         23

<210> SEQ ID NO 34
<211> LENGTH: 21
<212> TYPE: DNA
<213> ORGANISM: Homo sapiens

<400> SEQUENCE: 34
cagggtctct tgctggatgg g                                          21

<210> SEQ ID NO 35
<211> LENGTH: 28
<212> TYPE: DNA
<213> ORGANISM: Homo sapiens

<400> SEQUENCE: 35
aagctagctc cccaggtcac atcaaaag                                   28

<210> SEQ ID NO 36
<211> LENGTH: 28
<212> TYPE: DNA
<213> ORGANISM: Homo sapiens

<400> SEQUENCE: 36
aaggtaccaa aattagctgg gcgtgatg                                   28

<210> SEQ ID NO 37
<211> LENGTH: 28
<212> TYPE: DNA
<213> ORGANISM: Homo sapiens

<400> SEQUENCE: 37
```

```
aaggtacccc tgtgtcagac aagccaaa                                            28
```

<210> SEQ ID NO 38
<211> LENGTH: 28
<212> TYPE: DNA
<213> ORGANISM: Homo sapiens

<400> SEQUENCE: 38

```
aaggatccaa ggcaaccctg gagtctttt                                           28
```

<210> SEQ ID NO 39
<211> LENGTH: 28
<212> TYPE: DNA
<213> ORGANISM: Homo sapiens

<400> SEQUENCE: 39

```
aaggatcctc tgttgcccag agtgagtg                                            28
```

<210> SEQ ID NO 40
<211> LENGTH: 30
<212> TYPE: DNA
<213> ORGANISM: Homo sapiens

<400> SEQUENCE: 40

```
aactcgagtt cacaacattg ctgtttttca                                          30
```

<210> SEQ ID NO 41
<211> LENGTH: 629
<212> TYPE: PRT
<213> ORGANISM: Homo sapiens

<400> SEQUENCE: 41

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Leu Phe Phe His Lys Thr Pro Glu Thr Val Pro
305                 310                 315                 320

Gln Val Thr Ser Lys Ala Phe Gln His Asp Thr Trp Asn Ser Gly Leu
                325                 330                 335

Thr Val Ala Ser Ile Ser Thr Gly His Leu Thr Ser Asp Asn Arg Gly
                340                 345                 350

Asp Ile Gly Leu Leu Leu Gly Met Ile Val Phe Ala Val Met Leu Ser
            355                 360                 365

Ile Leu Ser Leu Ile Gly Ile Phe Asn Arg Ser Phe Arg Thr Gly Ile
        370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
                405                 410                 415

Glu Leu Met Asn Asn Asn Ser Ser Glu Gln Val Leu Tyr Val Asp Pro
                420                 425                 430

Met Ile Thr Glu Ile Lys Glu Ile Phe Ile Pro Glu His Lys Pro Thr
            435                 440                 445

Asp Tyr Lys Lys Glu Asn Thr Gly Pro Leu Glu Thr Arg Asp Tyr Pro
        450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
                485                 490                 495

His Leu Ser Asn Asn Asn Glu Ile Thr Ser Leu Thr Leu Lys Pro Pro
                500                 505                 510

Val Asp Ser Leu Asp Ser Gly Asn Asn Pro Arg Leu Gln Lys His Pro
            515                 520                 525

Asn Phe Ala Phe Ser Val Ser Ser Val Asn Ser Leu Ser Asn Thr Ile
        530                 535                 540

Phe Leu Gly Glu Leu Ser Leu Ile Leu Asn Gln Gly Glu Cys Ser Ser
545                 550                 555                 560

Pro Asp Ile Gln Asn Ser Val Glu Glu Glu Thr Thr Met Leu Leu Glu
                565                 570                 575

Asn Asp Ser Pro Ser Glu Thr Ile Pro Glu Gln Thr Leu Leu Pro Asp
            580                 585                 590

Glu Phe Val Ser Cys Leu Gly Ile Val Asn Glu Glu Leu Pro Ser Ile
        595                 600                 605

Asn Thr Tyr Phe Pro Gln Asn Ile Leu Glu Ser His Phe Asn Arg Ile
    610                 615                 620

Ser Leu Leu Glu Lys
625

<210> SEQ ID NO 42
<211> LENGTH: 8
<212> TYPE: PRT
<213> ORGANISM: Homo sapiens

<400> SEQUENCE: 42

Gly Leu Lys Glu Gly Ser Tyr Cys
1               5

<210> SEQ ID NO 43
<211> LENGTH: 5
<212> TYPE: PRT
<213> ORGANISM: Homo sapiens

<400> SEQUENCE: 43

Asp Asn Arg Gly Asp
1               5

<210> SEQ ID NO 44
<211> LENGTH: 21
<212> TYPE: DNA
<213> ORGANISM: Homo sapiens

<400> SEQUENCE: 44
atcattccga actgggtagg t                                             21

<210> SEQ ID NO 45
<211> LENGTH: 21
<212> TYPE: DNA
<213> ORGANISM: Homo sapiens

<400> SEQUENCE: 45
atcattccaa actgggtagg t                                             21

<210> SEQ ID NO 46
<211> LENGTH: 2766
<212> TYPE: DNA
<213> ORGANISM: Homo sapiens

<400> SEQUENCE: 46
aaacagtctt ttcctgcttc cagacatgaa tcaggtcact attcaatggg atgcagtaat      60 agcccttac atactcttca gctggtgtca tggaggaatt acaaatataa actgctctgg     120
ccacatctgg gtagaaccag ccacaatttt taagatgggt atgaatatct ctatatattg    180
ccaagcagca attaagaact gccaaccaag gaaacttcat ttttataaaa atggcatcaa    240
agaaagattt caaatcacaa ggattaataa acaacagctc cggctttggt ataaaaactt    300
tctggaacca catgcttcta tgtactgcac tgctgaatgt cccaaacatt ttcaagagac    360
actgatatgt ggaaaagaca tttcttctgg atatccgcca gatattcctg atgaagtaac    420
ctgtgtcatt tatgaatatt caggcaacat gacttgcacc tggaatgctg ggaagctcac    480
ctacatagac acaaaatacg tggtacatgt gaagagttta gagacagaag aagagcaaca    540
gtatctcacc tcaagctata ttaacatctc cactgattca ttacaaggtg caagaagta    600 cttggttttgg gtccaagcag caaacgcact aggcatggaa gagtcaaaac aactgcaaat    660
tcacctggat gatatagtga taccttctgc agccgtcatt tccagggctg agactataaa    720
tgctacagtg cccaagacca taatttattg ggatagtcaa acaacaattg aaaaggtttc    780

```
ctgtgaaatg agatacaagg ctacaacaaa ccaaacttgg aatgttaaag aatttgacac    840
caattttaca tatgtgcaac agtcagaatt ctacttggag ccaaacatta agtacgtatt    900
tcaagtgaga tgtcaagaaa caggcaaaag gtactggcag ccttggagtt cactgttttt    960
tcataaaaca cctgaaacag ttccccaggt cacatcaaaa gcattccaac atgacacatg   1020
gaattctggg ctaacagttg cttccatctc tacagggcac cttacttctg acaacagagg   1080
agacattgga ctttattgg gaatgatcgt ctttgctgtt atgttgtcaa ttctttcttt   1140
gattgggata tttaacagat cattccgaac tgggattaaa agaaggatct tattgttaat   1200
accaaagtgg ctttatgaag atattcctaa tatgaaaaac agcaatgttg tgaaaatgct   1260
acaggaaaat agtgaactta tgaataataa ttccagtgag caggtcctat atgttgatcc   1320
catgattaca gagataaaag aaatcttcat cccagaacac aagcctacag actacaagaa   1380
ggagaataca ggacccctgg agacaagaga ctacccgcaa aactcgctat cgacaatac   1440
tacagttgta tatattcctg atctcaacac tggatataaa ccccaaattt caaattttct   1500
gcctgaggga agccatctca gcaataataa tgaaattact tccttaacac ttaaaccacc   1560
agttgattcc ttagactcag gaaataatcc caggttacaa aagcatccta attttgcttt   1620
ttctgtttca agtgtgaatt cactaagcaa cacaatattt cttggagaat taagcctcat   1680
attaaatcaa ggagaatgca gttctcctga catacaaaac tcagtagagg aggaaaccac   1740
catgcttttg gaaaatgatt cacccagtga aactattcca gaacagaccc tgcttcctga   1800
tgaatttgtc tcctgtttgg ggatcgtgaa tgaggagttg ccatctatta atacttattt   1860
tccacaaaat attttggaaa gccacttcaa taggatttca ctcttggaaa agtagagctg   1920
tgtggtcaaa atcaatatga gaaagctgcc ttgcaatctg aacttgggtt ttccctgcaa   1980
tagaaattga attctgcctc ttttgaaaa aaatgtattc acatacaaat cttcacatgg   2040
acacatgttt tcatttccct tggataaata cctaggtagg ggattgctgg gccatatgat   2100
aagcatatgt ttcagttcta ccaatcttgt ttccagagta gtgacatttc tgtgctccta   2160
ccatcaccat gtaagaattc ccgggagctc catgcctttt taattttagc cattcttctg   2220
cctcatttct taaaattaga gaattaaggt cccgaaggtg gaacatgctt catggtcaca   2280
catacaggca caaaacagc attatgtgga cgcctcatgt atttttata gagtcaacta   2340
tttcctcttt attttccctc attgaaagat gcaaaacagc tctctattgt gtacagaaag   2400
ggtaaataat gcaaaatacc tggtagtaaa ataaatgctg aaaattttcc tttaaaatag   2460
aatcattagg ccaggcgtgg tggctcatgc ttgtaatccc agcactttgg taggctgagg   2520
taggtggatc acctgaggtc aggagttcga gtccagcctg gccaatatgc tgaaaccctg   2580
tctctactaa aattacaaaa attagccggc catggtggca ggtgcttgta atcccagcta   2640
cttgggaggc tgaggcagga gaatcacttg aaccaggaag gcagaggttg cactgagctg   2700
agattgtgcc actgcactcc agcctgggca acaagagcaa aactctgtct ggaaaaaaaa   2760
aaaaaa                                                              2766
```

<210> SEQ ID NO 47
<211> LENGTH: 20
<212> TYPE: DNA
<213> ORGANISM: Homo sapiens

<400> SEQUENCE: 47

```
gagtcaacgg atttggtcgt                                                 20
```

```
<210> SEQ ID NO 48
<211> LENGTH: 20
<212> TYPE: DNA
<213> ORGANISM: Homo sapiens

<400> SEQUENCE: 48
gacaagcttc ccgttctcag                                               20

<210> SEQ ID NO 49
<211> LENGTH: 24
<212> TYPE: DNA
<213> ORGANISM: Homo sapiens

<400> SEQUENCE: 49
aatgctggga agctcaccta cata                                          24

<210> SEQ ID NO 50
<211> LENGTH: 25
<212> TYPE: DNA
<213> ORGANISM: Homo sapiens

<400> SEQUENCE: 50
gcttgtgttc tgggatgaag atttc                                         25
```

US 9,868,776 B2

ANTI-SENSE OLIGONUCLEOTIDES TARGETED AGAINST EXON 9 OF IL-23R-ALPHA GENE AND METHOD OF USING SAME TO INDUCE EXON SKIPPING AND TO TREAT INFLAMMATORY BOWEL DISEASES

CROSS-REFERENCE TO RELATED APPLICATION

This application is a continuation of U.S. Utility application Ser. No. 14/088,553, filed Nov. 25, 2013, which is a continuation of U.S. Pat. No. 8,618,070, filed May 2, 2011, which claims the benefit of U.S. Provisional Application No. 61/343,615 filed Apr. 30, 2010 under 35 U.S.C. §119(e), the contents of which are incorporated by reference herein in their entireties.

FIELD OF THE INVENTION

The present invention generally relates to anti-sense oligonucleotides targeted against an exon region on the IL-23Rα gene to enhance IL-23Rα alternative gene splicing. Specifically, the present invention relates to anti-sense oligonucleotides and compositions thereof against the exon 9 of the IL-23Rα to induce exon skipping and thus increase the production of a soluble translated form of IL-23Rα (Δ9 protein, which lacks a transmembrane domain and a cytoplasmic domain, but has a unique eight (8) amino acid sequence (GLKEGSYC) as a result of exon 9 skipping. The soluble truncated IL-23Rα (Δ9) protein is useful as a therapeutic agent to inhibit cell signaling mediated by IL-23 necessary for differentiation of Th17 cells. The present invention hence provides a method of treating inflammatory bowel diseases (e.g., Crohn's disease) using anti-sense oligonucleotides targeted against the exon 9 of the IL-23Rα gene.

BACKGROUND OF THE INVENTION

IL-23 comprises a p19 subunit and a p40 subunit that are disulfide-linked. IL-23 exerts its biological activities by binding to IL-23 receptor (IL-23R). IL-23R comprises an IL-23Rα subunit and an IL-12R81 subunit. When IL-23 binds to IL-23R, it leads to intracellular signaling including phosphorylation of STAT1, STAT3, STAT4 and STAT5. IL-23R is expressed on T-cells, NK cells, monocytes, and dendritic cells and its expression pattern corresponds with the ability of these cells to respond to IL-23. Mice lacking p19 exhibit a decreased pro-inflammatory response to experimental autoimmune encephalomyelitis, inflammatory bowel disease and collagen-induced arthritis. While IL-23 per se cannot induce the differentiation of naïve CD4 T-cells into Th-17 cells in vitro, the differentiation of Th17 cells in vivo may require IL-23. The observed protective effect in p19-deficient mice may relate to the lack of differentiation of Th17 cells.

IL-23Rα mRNA in human is 2.8 kb long and contains a total of 11 exons (NM_144701). The mature translated IL-23Rα protein is a type-I transmembrane protein (629 amino acids) and contains three (3) structural domains: (1) a signal peptide domain; (2) an extracellular region containing a fibronectin III-like domain; and (3) a 253 amino acid residue cytoplasmic domain with three (3) potential tyrosine phosphorylation sites.

While IL-23 is shown to bind to IL-23R and mediates Jak-STAT cell signaling, Parham et al. explicitly stated their inability to demonstrate human IL-23Rα-Ig and soluble human IL-23Rα-V5-His6 (composed of the entire extracellular domain—amino acids 1-353) as effective antagonists for human IL-23R. Daniel J. Cua et al. disclosed treatment methods for multiple sclerosis, neuropathic pain, and inflammatory bowel disorders using antibodies against IL-23 and its receptor. Contrary to Parham's statement, Cua proposes using a soluble receptor based on the extracellular region of a subunit of the IL-23 receptor (PCT/US2004/003126) as an antagonist. A recombinant human IL-23Rα Fc chimeric protein is commercially available (R&D Systems) and claimed to have the ability to inhibit IL-23 induced IL-17 secretion in a mouse splenocytes system. It remains unclear as to whether any of these proposed soluble IL-23R as may in fact exist in vivo as a naturally-occurring protein, let alone the possibility that such soluble IL-23R as may possess ability to block IL-23Rα mediated cell signaling. To this end, Daniel J. Cua et al. (PCT/US2004/003126) failed to provide any evidence that a soluble IL-23 receptor can indeed block IL-23 mediated cell signaling as well as inhibit Th17 producing cells.

Parham et al. disclosed the genomic organization of the IL-23R (composed of an IL-23α subunit and an IL-12W subunit). Recent evidence suggests that IL-23Rα gene may undergo extensive alternative mRNA splicing. There are at least twenty-four (24) potential gene transcripts for IL23Rα. From these IL-23Rα alternatively spliced mRNA sequences, there appears at least four (4) deduced putative translated proteins: (1) a short premature IL-23Rα extracellular peptide; (2) a possible soluble form of IL-23Rα lacking the transmembrane/intracellular domain; (3) a full-length IL23Rα with truncated extracellular region; and (4) a non-responsive membrane bound receptor isoform of IL-23Rα with deletion in intracellular signaling components.

Although many gene transcripts for IL-23Rα (i.e., IL-23Rα splice variants) are suggested, it is important to point out that their actual existence in vivo is unknown. There is little information regarding whether any of the deduced IL-23Rα translated products actually exist in vivo, let alone the function of these IL-23Rα protein variants, if any.

Duerr et al. first reported rs11209026 as an IL-23Rα coding variant (single nucleotide polymorphism, SNP) and associated the rs11209026 with protection against Crohn's disease (Science, Vol. 314 1 Dec. 2006). The mechanism by which SNP (rs11209026) functions is not known. Because rs11209026 is present on the exon 9 and results in amino acid change in the cytoplasmic domain of IL-23Rα, it is speculated that the SNP may affect IL-23Rα-mediated intracellular signaling.

To this end, Pidasheva et al. reported that the presence of rs11209026 interferes with the IL-23Rα intracellular signaling. Using the CD4+ T cells generated from healthy donors with wild-type and SNP rs11209026 haplotypes, this research group reported that donors with protective haplotype had significantly reduced STAT3 phosphorylation when compared to the wild-type counterparts. In contrast, de Paus et al. measured IL-23 signal transduction (i.e., STAT3) and IFN-γ and IL-10 production and found no detectable differences between the genetic variant (SNP rs11209026) and wild-type in the function of the IL-23Rα chain. (de Paus et al., 2008, Mol. Immunol., 45, 3889-95). These contradicting findings highlight the fact that the functional role of SNP rs 11209026 in IL-23Rα is far from clear.

Accordingly, there is continuing need for discovery of a therapeutic agent that inhibits IL-23 cellular signaling and antagonizes Th17 cell maturation. The present inventors have surprisingly discovered that the rs11209026 increases alternative splicing and leads to production of a naturally-occurring soluble form of IL-23Rα. The soluble form of IL-23Rα lacks the exon-9 of the IL-23Rα chain mRNA transcript (e.g., Δ9) and is found to be capable of blocking IL-23R signaling. The present inventors further discovered the use of anti-sense oligonucleotides to mimics rs11209026 to increase exon 9 skipping and increases production of Δ9. The present anti-sense oligonucleotides have the utility application to treat inflammatory bowel diseases such as Crohn's disease.

SUMMARY OF THE INVENTION

In one aspect, the present invention provides an anti-sense oligonucletode 15-30 nucleobases in length targeted to exon 9 of IL-23Rα gene, wherein said anti-sense oligonucleotide induces exon 9 skipping and increases the production of a truncated IL-23Rα mRNA form having a nucleotide sequence set forth in SEQ ID NO: 4.

In one aspect, the anti-sense oligonucleotide is targeted to the exon 9 of the IL-23Rα gene, the nucleotide sequence of which is set forth in SEQ ID NO: 2. The present inventors showed that as long as the anti-sense oligonucleotide anneals to exon 9 or at least to a portion of exon 9, they would sufficiently induce exon 9 skipping. Success in exon 9 skipping by anti-sense oligonucleotides can be measured via an increase in the production of a truncated IL-23Rα (Δ9) mRNA (SEQ ID NO: 4) or its translated protein (i.e., soluble truncated IL-23Rα (Δ9) protein (SEQ ID NO: 5). One embodiment of the present invention includes anti-sense oligonucleotides that anneal to sixteen (16) nucleotides of the exon 9. Another embodiment of the present invention includes anti-sense oligonucleotides that anneal to twenty-two (22) nucleotides of exon 9. Another embodiment includes anti-sense oligonucleotides that anneal to fourteen (14) nucleotides of exon 9. Yet, another embodiment includes anti-sense oligonucleotides that anneal to twelve (12) nucleotides of exon 9. All these anti-sense oligonucleotides that anneal to a portion of exon 9 are found to be sufficient to induce exon 9 skipping, as evidenced by an increase in Δ9 mRNA and Δ9 protein production (See, FIG. 28 and FIG. 29).

In one aspect, the present invention provides an anti-sense oligonucleotide selected from the group consisting of SEQ ID NO: 10, SEQ ID NO: 12, SEQ ID NO: 13, SEQ ID NO: 14, and SEQ ID NO: 15.

In one aspect, the anti-sense oligonucleotide comprises a modified inter-nucleoside linkage. Preferably, the modified inter-nucleoside linkage is a phosphorothioate linkage.

In one aspect, the anti-sense oligonucleotide comprises a modified sugar moiety. Preferably, the modified sugar moiety is a 2'-O-methyl sugar moiety.

In one aspect, the present invention provides a pharmaceutical composition comprising an anti-sense oligonucletode 15-30 nucleobases in length targeted to exon 9 of IL-23Rα gene and a pharmaceutical acceptable excipient, wherein said anti-sense oligonucleotide induces exon 9 skipping and increases the production of a soluble truncated IL-23Rα form having a nucleotide sequence set forth in SEQ ID NO: 4. Preferably, the anti-sense oligonucleotide is selected from the group consisting of SEQ ID NO: 10, SEQ ID NO: 12, SEQ ID NO: 13, SEQ ID NO: 14, and SEQ ID NO: 15.

In one aspect, the present invention provides a method of producing a soluble truncated IL-23Rα having a nucleotide sequence set forth in SEQ ID NO: 4, comprising the step of exposing an anti-sense oligonucleotide to a mammalian cell, wherein said anti-sense oligonucleotide targeted to exon 9 of IL-23Rα gene to induce skipping of exon 9 in said cell. Preferably, the mammalian cell is a human cell; such as a human immune cell.

In one aspect, the present invention provides a method of treating a human inflicted with inflammatory bowel diseases such as Crohn's disease or ulcerative colitis, comprising the steps of: (a) administering an effective amount of an anti-sense oligonucleotide to said human, wherein said anti-sense oligonucleotide induces exon 9 skipping and induces production of a soluble truncated IL-23Rα protein, wherein said anti-sense oligonucleotide is targeted against exon 9 of IL-23Rαgene and wherein said soluble truncated IL-23Rα protein has an amino acid sequence set forth in SEQ ID NO: 5.

In one aspect, the present invention provides a method of using an anti-sense oligonucleotide to induce exon skipping (of exon 9) and production of an isolated soluble IL-23Rα protein, wherein said protein has the following characteristics of: a) lacking a transmembrane domain; b) existing as a monomer; and c) having the ability to inhibit IL-23R-mediated cell signaling. The soluble IL-23Rαprotein has the capability of inhibiting IL23R-mediated cell signaling. An exemplary cell signaling event includes the formation of at least one transcriptional factor (phosphorylated) selected from the group consisting of STAT1, STAT2, STAT3, and STAT5. Preferably, the IL-23R-mediated cell signaling is the STAT3 formation.

In one aspect, the soluble IL-23Rα protein has the capability of inhibiting IL-23R-mediated cell signaling. An exemplary cell signaling includes the formation of IL-17A or IL-17F. Preferably, it is the IL-17A formation (i.e., production or secretion) of IL-17A.

In one aspect, the present invention provides a soluble IL-23Rα protein that has the ability to inhibit Th17 cell maturation.

In one aspect, the present invention provides a method of using an anti-sense oligonucleotide to induce exon skipping (of exon 9) and production of an isolated soluble IL-23Rα protein, wherein said protein contains eight (8) amino acids of GLKEGSYC (SEQ ID NO: 42), which are present at the C-terminus of the soluble IL-23Rα protein. The GLKEGSYC sequence is novel (i.e., not present in the native IL-23Rα protein), and occurs as a result of frame-shift on exon 10 (due to exon 9 skipping). The GLKEGSYC (SEQ ID NO: 42) sequence is found present in the C-term inal end of the Δ9 protein. The soluble IL23Rαprotein (Δ9) lacks five (5) amino acids (i.e., DNRGD (SEQ ID NO: 43)). The missing five (5) amino acid residues are located at the extracellular domain (i.e., C-terminal end of the extracellular domain), and in the proximity of the transmembrane domain.

In one aspect, the present invention provides a method of using an anti-sense oligonucleotide to induce exon skipping (of exon 9) and production of an isolated soluble IL-23Rα protein, wherein said soluble IL23Rα has a total of 356 amino acid residues, after protein translation (See, FIG. 8B). However, when the IL-23Rα protein becomes mature (i.e., signal peptide is cleaved to form the mature protein), it has a total of 333 amino acid residues (because the signal peptide is a 23 amino acid residue long) (Δ9) (See, FIG. 8C). The soluble IL-23Rα (represents a mature protein) has an amino acid sequence set forth in SEQ ID NO: 5. The isolated soluble IL-23Rα protein is encoded by a cDNA having a nucleotide sequence set forth in SEQ ID NO: 4. The soluble IL-23Rα protein (Δ9) (SEQ ID NO: 5) is derived from a human cell, and the protein may be a recombinant protein.

In one aspect, the present invention provides a method of treating a human, comprising the steps of: a) identifying a human inflicted with an inflammatory bowel disease; b) administrating a pharmaceutical composition comprising an anti-sense oligonucleotide and a pharmaceutical acceptable excipient. The anti-sense oligonucleotides function to induce exon 9 skipping and production of a protein containing an amino acid sequence as set forth in SEQ ID NO: 5. Preferably, the anti-sense oligonucleotide is selected from the group consisting of SEQ ID NO: 10, SEQ ID NO: 12, SEQ ID NO: 13, SEQ ID NO: 14, and SEQ ID NO: 15.

DESCRIPTION OF THE DRAWINGS

FIG. 3B depicts the DNA sequence of exon 8 and 5' end of intron 8 (SEQ ID NO: 1). The underline region represents exon 8. The bold "GT" represents the 5' splice donor site.

FIG. 3C depicts the DNA sequence of 3' end of intron 8, exon 9 and 5' end of intron 9 (SEQ ID NO: 2). The underline region represents exon 9. The bold "CTAA" represents the predicted branch site. The bold "AG" represents the 3' splice acceptor site. The bold "GT" represents the 5' splice donor site.

FIG. 3D depicts the DNA sequence of 3' end of intron 9 and exon 10 (SEQ ID NO: 3). The underline region represents exon 10. The bold "CTAA" represents the predicted branch site. The bold "AG" represents the 3' splice acceptor site.

FIG. 8B depicts the nucleotide sequence of the coding region for Δ9 (Top) (SEQ ID NO: 4) as well as the amino acid sequence for the translated Δ9 protein (Below) (SEQ ID NO: 5).

FIG. 8C depicts the amino acid alignment between wild-type IL-23Rα and that of Δ9.

FIG. 19 depicts the effect of 2'-O-methyl anti-sense oligonucleotides (AONs) with phosphorothioate bonds modification on the exon 9. The AONs is 22 nucleotides long and binds to the end of exon 9 and the 5' splice donor site on the intron 9. The sequence of AONs (SEQ ID NO: 10) and control oligos (SEQ ID NO: 11) were shown in the figure. 293T cells were co-transfected with common allele minigene plasmid and control or IL23Rαspecific AONs. RNA was prepared 24 hours post-transfection and was reverse transcribed into cDNA. The expression levels of two mRNA transcripts, exon 8/9/10 and exon 8/10, were measure by RT-PCR.

FIG. 23 depicts the dose effect of AONs on the exon 9 skipping in the human leukocytes. Two different doses of AONs, 50 pmole and 100 pmole, were transfected into the human leukocytes. The expression level of Δ9, which was consequence of the AONs-mediated exon 9 skipping, was measure by real-time qRT-PCR (Top) and RT-PCR (Bottom).

DETAILED DESCRIPTION OF THE INVENTION

Definitions

Figure 1:
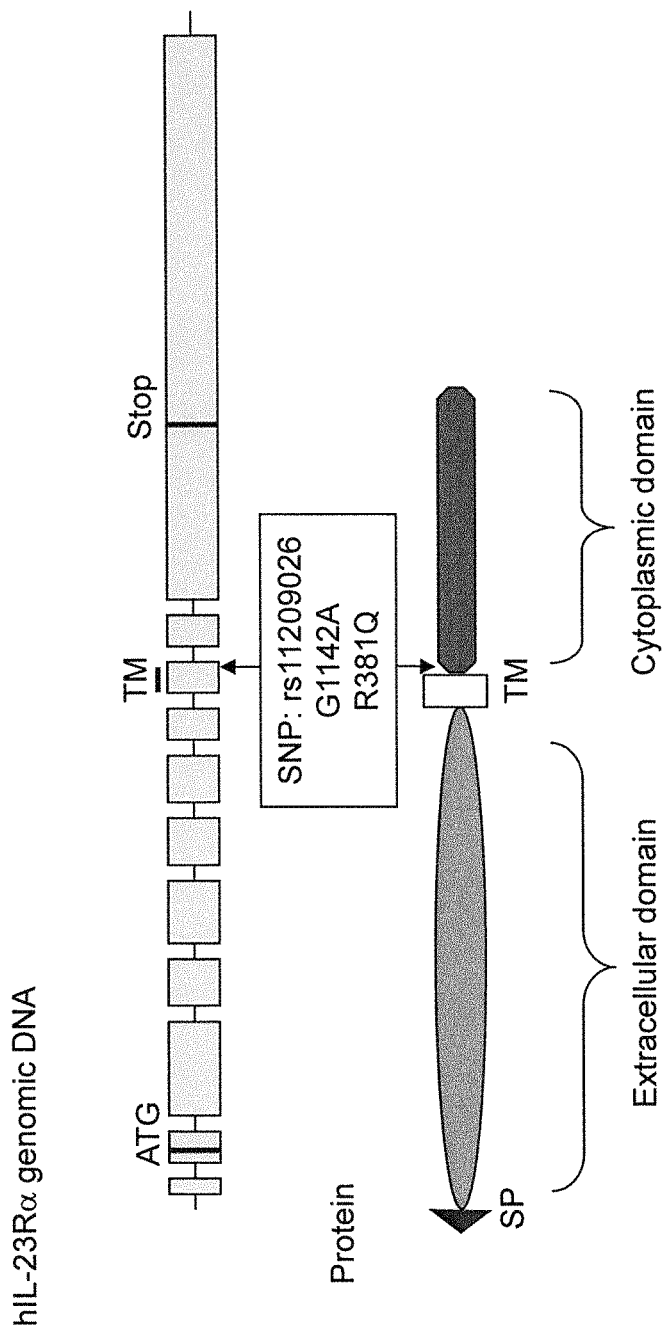
FIG. 1 depicts the schematic representation of gene organization of human IL-23Rα: Protein translation starts at exon 2 and stops at exon 11. The transmembrane region is encoded by the exon 9. The SNP rs11209026 is mapped on exon 9 after the transmembrane coding region (Top). The bottom panel depicts the protein organization of IL-23Rα. The protein starts with signal peptide and is followed by the extracellular domain, the transmembrane region and the cytoplasmic domain. The SNP rs11209026 causes the amino acid change from Arginine (R) to Glutamine (Q) at position 381 located in the cytoplasmic domain.

The following definitions are used for this application:

The term "IL-23R" refers to interleukin-23 receptor. IL-23R is composed of two (2) subunits: IL-23Rα and IL-12R/31. The IL-23Rα gene is located on chromosome 1 p31.3. The full-length translated IL-23Rα protein is a type I cytokine receptor and interacts with human IL-12Rβ1 to form the heterodimeric IL-23R receptor. Human IL-12R/31 also partners with human IL-12Rβ2 to form the cell-surface IL-12 receptor. When IL-23 is bound to the IL-23 receptor, the IL-23Rα chain triggers a series of cell signaling events including activation of Janus kinase 2 (JAK2), and transcription activator STAT3. IL-23R is present on many immune system cells, including T cells, natural killer (NK) cells, monocytes, and dendritic cells.

The term "soluble IL-23Rα" refers to an IL-23Rα lacking a transmembrane domain and a cytoplasmic domain, thus rendering the protein soluble in an aqueous medium. A soluble IL-23Rα protein may be present as monomer or form a homodimer (as is the case for the chimeric molecule where human Fc (from an IgG1 molecule) that is fused with IL-23Rα molecule. For purposes of this application, the term "soluble IL-23Rα" includes the naturally-occurring truncated IL-23Rα as a result of alternative gene splicing. In particular, it includes Δ9 protein having an amino acid sequence set forth in SEQ ID NO: 5.

The term "Δ9" refers to the naturally-occurring truncated IL-23Rα resulting from IL-23Rα alternative splicing. Exon 9 is skipped during mRNA splicing resulting in the fusion of exon 8 to exon 10 of IL-23Rα mRNA. The resulting mRNA of the "Δ9" refers to spliced isoform of IL-23Rα without exon 9. For a detailed description, please refer to Kan et al., Genes Immun. 9, 631-639 (2008), the content of which is herein incorporated by reference. The Δ9 protein has 348 amino acids plus eight (8) novel amino acid sequences unique to Δ9 (a total of 356 amino acids). Amino acid sequence comparison between Δ9 and wild-type IL-23Rα (extracellular domain; 353 amino acids) is provided in FIG. 8C. The signal sequence (i.e., 1-23 amino acids) on the immature Δ9 protein (located inside the cells) is cleaved before the mature Δ9 protein is released outside of the cells. The mature Δ9 protein therefore has a total of 333 amino acids (i.e., 356-23). For purposes of this application, therefore, the term "Δ9 protein" is intended to include Δ9 proteins with or without the signal sequence.

The term "Δ5" refers to the naturally-occurring alternatively spliced IL-23Rα isoform. Exon 5 is skipped during mRNA splicing resulting in the fusion of exon 4 to exon 6 of IL-23Rα mRNA. The resulting mRNA of the "Δ5" refers to spliced isoform of IL-23Rα without exon 5. Δ5 protein is a translated protein from Δ5 mRNA. For a detailed description, please refer to Kan et al., Genes Immun. 9, 631-639 (2008), the content of which is herein incorporated by reference.

The term "Δ8" refers to the naturally-occurring alternatively spliced IL-23Rα isoform. Exon 8 is skipped during mRNA splicing resulting in the fusion of exon 7 to exon 9 of IL-23Rα mRNA. The resulting mRNA of "Δ8" isoform refers to spliced isoform of IL-23Rα without exon 8. Δ8 protein is a translated protein from Δ8 mRNA. For a detailed description, please refer to Kan et al., Genes Immun. 9, 631-639 (2008), the content of which is herein incorporated by reference.

The term "Δ8,9" refers to the naturally-occurring truncated IL-23Rα resulting from IL-23Rα gene splicing. Exons 8 and 9 are skipped during mRNA splicing resulting in the fusion of exon 7 to exon 10 of IL-23Rα mRNA. The resulting mRNA of "Δ8,9" isoform refers to spliced isoform of IL-23Rα without exons 8,9. For a detailed description, please refer to Kan et al., Genes Immun. 9, 631-639 (2008), the content of which is herein incorporated by reference. The Δ8,9 protein has 318 amino acids plus eight (8) novel amino acid sequence unique to Δ8,9 (a total of 326 amino acids). Amino acid sequence comparison between Δ8,9 and wild-type IL-23Rα (extracellular domain; 353 amino acids) is provided in FIG. 3E. The signal sequence (i.e., 1-23 amino acids) on the Δ8,9 is cleaved before the mature Δ8,9 protein is released. Therefore, the mature Δ8,9 has a total of 303 amino acids (i.e., 24-326). For purposes of this application, the term "Δ8,9" is intended to include Δ8,9 forms with or without the signal sequence (i.e., immature and mature Δ8,9 proteins).

The term "anti-sense oligonucleotides" (AONs) refers to a single-stranded RNA or DNA that specifically binds to a target nucleic acid sequence. Such oligonucleotide is complementary to a target "sense" nucleic acid, and functions by sequence-specific mechanisms. The binding interferes with the normal regulatory function of the target nucleic acid. For examples, an AON that hybridizes to a pre-mRNA would interfere with the mRNA splicing and causes exon skipping. The functions of the target nucleic acid to be interfered with include, for example, replication, transcription, mRNA splicing and exon skipping.

The term "mRNA" refers to the template for protein synthesis; the form of RNA that carries information from DNA in the nucleus to the ribosome sites of protein synthesis in the cell.

The term "pre-mRNA" refers to an immature single strand of messenger ribonucleic acid (mRNA). Pre-mRNA is synthesized from a DNA template in the cell nucleus by transcription. Pre-mRNAs include two different types of segments, exons and introns.

The term "exon" refers to protein-coding sequences of a gene. The nucleic acid sequence of an exon is represented in the mature form of an RNA molecule after portions of a precursor RNA (introns) have been removed.

The term "intron" refers to a segment of a gene situated between exons that is removed before translation of messenger RNA and does not function in coding for protein synthesis. Thus, intron is a DNA region within a gene that is not translated into protein.

The term "splicing" refers to the maturation process of mRNA after transcription, in which introns are removed and exons are joined.

The term "exon skipping" refers to the process results in mature RNA (i.e. mRNA) that does not contain the skipped exon and may lead to the expression of an altered protein product (when compared to that without exon skipping).

The term "exonic splicing enhancer" (ESE) is a DNA sequence motif within an exon that directs, or enhances, accurate splicing pre-mRNA into messenger RNA (mRNA).

The term "exonic splicing silencer" (ESS) is a small region of an exon that inhibits or silences splicing of the pre-mRNA.

Figure 10:
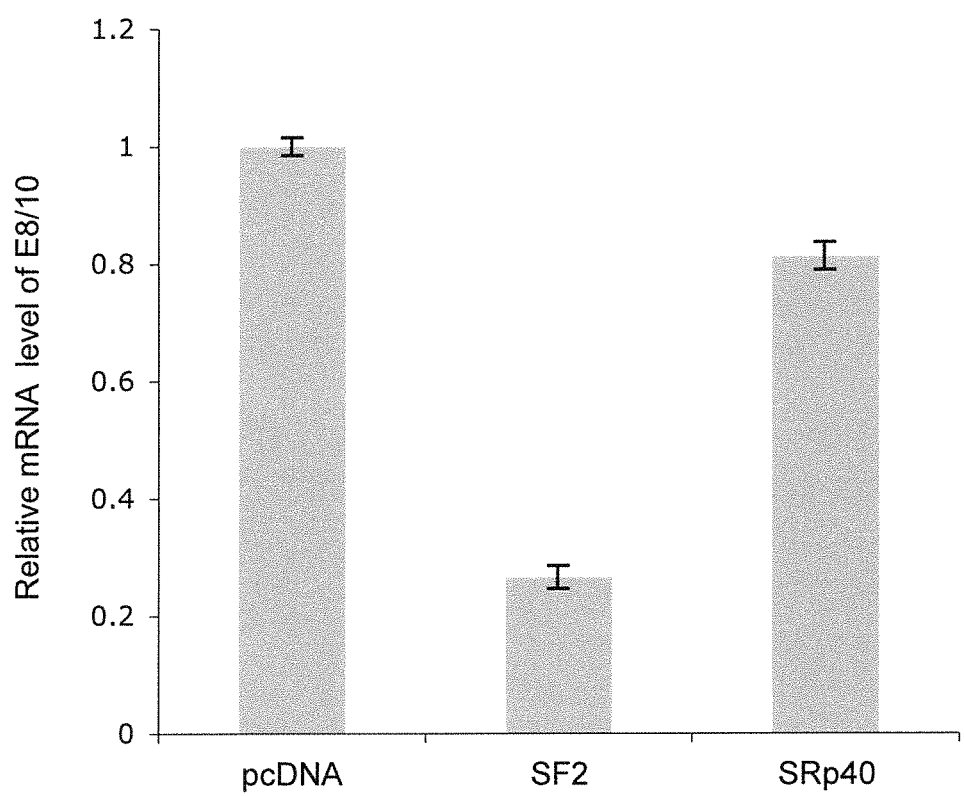
FIG. 10A depicts the DNA coding sequence (SEQ ID NO: 6) and amino acid sequence (SEQ ID NO: 7) for SF2.
FIG. 10B depicts the DNA coding sequence (SEQ ID NO: 8) and amino acid sequence (SEQ ID NO: 9) for SRp40.
FIG. 10C depicts the effect of SF2 and SRp40 overexpression on exon 9 splicing using the common allele mini-gene. 293T cells were co-transfected with common allele mini-gene plasmid and pcDNA or SF2 or SRP40 expression constructs. Expression level of exon8/10 transcript was quantitated by real-time qRT-PCR.

The term "Splicing Factor 2" (SF2) refers to splicing factor, arginine/serine-rich 1 (SFRS1) or alternative splicing factor (ASF). The nucleotide coding sequence is shown in FIG. 10A (SEQ ID NO: 6). SF2 is an essential sequence-specific splicing factor involved in pre-mRNA splicing. SF2 is found on chromosome 17. The resulting splicing factor is a protein of approximately 33 kDa (SEQ ID NO: 7). SF2 is necessary for all splicing reactions to occur, and influences splice site selection in a concentration-dependent manner, resulting in alternative splicing.

The term "SF2 binding site" refers to the nucleic acid sequence that is specifically recognized and is bound by SF2 protein.

The term "phosphorothioate oligonucleotide" means an oligonucleotide having a phosphorothioate linkage in place of a naturally occurring phosphodiester linkage.

The term "mini-gene" generally refers to a gene segment that codes for a portion of a protein. For the present application, the term "mini-gene" refers to a genomic fragment that includes the alternative exon(s) (i.e., exon 9) and the surrounding introns (intron 8 and intron 9) as well as the flanking constitutively spliced exons (exon 8 and exon 10) (SEQ ID NO: 1 to 3; FIGS. 3A, 3B, 3C and 3D). Such a mini-gene is cloned in a eukaryotic expression vector. Thus, the transfected mini-gene should contain the RNA-elements necessary for mRNA splicing. The elements include 5' splice donor site, 3' splice acceptor site and "A" branch site. In this invention, the mini-gene contains entire exon 8, exon 9 and exon 10. However, only parts of the intron 8 and intron 9 are included in the mini-gene (FIGS. 3A, 3B, 3C 15 and 3D).

The term "bacterial artificial chromosome (BAC)" refers a DNA construct containing a piece of chromosome. For purposes of this application, the BAC refers to BAC RP11-684P13 and it contains a DNA insert with a ~138 kB from human chromosome 1. This particular piece of chromosome includes a ~33 kKB of DNA fragment upstream of IL-23Rαtranscriptional start, ~93 kB of a DNA fragment containing all the exons and introns of IL-23Rα, as well as a ~12 kB of DNA fragment downstream of the exon 11 of IL-23Rα. Unlike mini-gene, BAC contains authentic regulatory elements (including promoters and enhancers) for the IL-23Rα transcriptional regulation.

The term "5' splice donor site" refers to an almost invariant sequence GU at the 5' end of the intron.

The term "3' splice acceptor site" refers to almost invariant AG sequence at the 3' end of the intron.

The term "branch site" refers to the location upstream from the 3' splice acceptor site. There is a region high in pyrimidines (C and U), or polypyrimidine tract. Upstream from the polypyrimidine tract is the branch point, which includes an adenine nucleotide.

The term "hybridization" refers to the process of forming a double stranded nucleic acid from joining two complementary strands of DNA or RNA.

The term "mammal" refers to any animal classified as a mammal, including humans, and animals. Preferably, the mammal is human.

The term "autoimmune disease" refers to a pathological condition in mammals that is typically characterized by an unregulated immune cell activity. Examples of autoimmune include but are not limited to, inflammatory bowel disease, Crohn's disease, asthma and the like. Preferably, the autoimmune diseases are characterized by an increased Th17 activity (likely attributed to enhanced IL-17A and IL-17F activity). The present invention provides an isolated soluble IL-23Rα protein useful for treating inflammatory bowel diseases, such as Crohn's disease. The present invention also provides a composition and method for treating inflammatory bowel diseases.

The term "inflammatory bowel disease" means an inflammatory disease in bowel that involves Th17 cells. Crohn's disease and Ulcerative colitis represent exemplary diseases of the inflammatory bowel disease.

The term "effective amount" refers to an amount of soluble IL-23Rα sufficient to ameliorate a symptom of a pathological disease (such as Crohn's disease).

The present inventors discovered a hitherto unknown soluble form of a human IL-23Rα receptor (e.g., Δ9). The Δ9 mRNA is a result of alternative splicing of the IL-23Rα gene that encodes the native IL-23Rα protein. The splice variant Δ9 is missing the exon 9 and does not contain a transmembrane domain and an intracellular domain. In Δ9, Exon 8 joins to Exon 10 and results in the shift of open reading frame and hence generates the novel eight (8) amino acid sequences (i.e., GLKEGSYC (SEQ ID NO: 42)). Δ9 mRNA represents up to 20% of human leukocyte IL-23Rαtranscript and thus is a major form of IL-23Rα mRNA. Δ9 mRNA is detectable in the Fragment Analysis studies. The Δ9 form of IL-23Rα is secreted as a soluble monomer form and binds to IL-23 in solution.

The present inventors further discovered that this soluble IL-23Rα form is capable of blocking IL-23 induced STAT3 phosphorylation and Th17 maturation. A detailed description of these findings has been provided in two (2) pending U.S. patent applications (i.e., "Therapeutic Applications of Isolated Naturally-Occurring Soluble Truncated Forms of IL-23 Receptor" application Ser. No. 13/065,878 filed Mar. 31, 2010; and "ELISA for Naturally-Occurring Soluble Truncated Form of IL-23 Receptor" application Ser. No. 13/065,867 filed Mar. 31, 2010). The entire disclosure of these two (2) pending applications is hereby incorporated by reference.

The present inventors discovered that rs11209026 enhances exon 9 skipping, and that anti-sense oligonucleotides against the exon 9 of the IL-23Rαgene mimics the functional effect of the rs11209026. In one embodiment, the present invention provides an anti-sense oligonucleotide against the exon 9 of the IL-23Rα gene to induce production of an isolated truncated IL-23Rα protein (i.e., Δ9). The subsequent Δ9 protein can be used as an inhibitor of IL-23 cell signaling, in particularly in the context of inflammatory bowel diseases.

It is known that the native form of human IL-23Rα mRNA (SEQ ID NO: 46) is 2.8 kb long, with 11 exons (NM_144701). This mRNA is translated into a type-I transmembrane protein of 629 amino acids (SEQ ID NO: 41). The native human IL-23Rα protein comprises an extracellular domain that contains 353-residue extracellular domain that includes a signal peptide, a fibronectin-III-like domain, as well as a 253-residue cytoplasmic domain with three potential tyrosine phosphorylation sites. Genetic studies have suggested an association the IL-23Rαlocus with protection/susceptibility in autoimmune inflammatory disorders, although the exact mechanistic basis remains elusive.

Using Fragment Analysis, the present inventors surprisingly discovered that there are six (6) alternative splice forms in human leukocytes. One of the forms (i.e., Δ9)

represents the majority alternative splice form. Δ9 is found to be soluble and exists as monomer, and it has the ability to bind IL-23 and inhibit the generation of functional human Th-17 cells in vitro. Different from that of the native IL-23Rαprotein, the present soluble truncated IL-23Rα lacks a transmembrane domain and contains 356 amino acids. The soluble monomer of Δ9 protein possesses the ability to block IL-23R mediated cell signaling.

The present inventors have unexpectedly discovered a novel soluble truncated IL-23Rα. The present invention extends our previous findings that IL-23Rα mRNA undergoes extensive alternative splicing—resulting in twenty-four (24) different potential transcripts. Four different classes of putative translation products could be deduced from these alternatively spliced mRNA sequences: (i) short premature IL-23Rα extracellular peptides; (ii) soluble forms of IL-23Rα lacking transmembrane/intracellular domains; (iii) full-length IL-23Rα with a truncated extracellular region; and (iv) a membrane bound receptor isoform of IL-23Rα that lacked likely intracellular signaling components.

The present inventors have unexpectedly discovered a novel functional role of the rs11209026 in inducing the exon 9 skipping and formation of a soluble truncated IL-23Rα. According to the present invention, the soluble truncated IL-23Rα contains a unique eight (8) amino acid sequence (GLKEGSYC (SEQ ID NO: 42)) at its C-terminus (in proximity of the transmembrane domain) due to the alternative translation reading frame on exon 10. When analyzed under conditions of a reducing gel electrophoresis, the molecular weight of the protein is approximately 60 kDa. The soluble truncated IL-23Rα protein corresponds to a N-terminal fragment of IL-23Rα lacking the transmembrane domain and has 326 amino acids (with 318 amino acids correspond to that of the native IL-23Rα). The amino acid sequence of the soluble truncated IL-23Rα is set forth in SEQ ID NO: 5.

Several factors should be taken into account when it comes to optimization of AON length. Short AONs may have the advantage of being easily internalized by cells. However, if they are not long enough, for example less than 10 nucleotides in length, they may not form specific and stable hybrids with target sequence. On the other hand, long AONs may hybridize to their targets with increased stability and enhance exon skipping. However, if they are too long, for example greater than 100 nucleotides in length, it may not be efficiently taken up by cells or could potentially be cytotoxic.

The present invention encompasses an optimal length of the AONs that can function to induce exon 9 skipping for IL-23Rα. Preferably, the AONs are about 10 to 50 nucleotides in length. Preferably, the AONs are about 15 to 30 nucleotides in length, and more preferably about 15 to 22 nucleotides in length. The lengths of AONs may conveniently be optimized. For example, the optimization is achieved by determining the efficiency of these oligonucleotides to induce exon 9 skipping (that is, induces the production of Δ9). The existence of any modifications in the oligonucleotide will influence the effects of length on overall efficiency of the oligonucleotide.

The AONs of the present invention may be unmodified or modified. Modified AONs include altering the natural structures of a nucleic acid. For example, AONs may include altering the phosphodiester linkage, sugars (ribose for RNA and deoxyribose for DNA) and purine/pyrimidine bases. Modifications can be made to an oligonucleotide insofar as they retain ability to hybridize to the target nucleic acid.

Preferably, modifications of the phosphodiester linkage render AONs more stable against nucleases, as well as enhancing cellular uptake. Modified phosphodiester linkages include phosphorothioate, methylphosphonate, phosphorodithioate, or phosphoselenate linkages. The AONs of the present invention may contain all of these modified linkages, including a mixture of different modified linkages and unmodified linkages. The synthesis of the modified AONs is recognized by one of the ordinary skill in the art.

Preferably, modification of AONs includes the incorporation of modified sugar groups such as alpha-anomers or the sugars incorporated into 2'-O-methyloligonucleotides.

Also contemplated are modifications to the nucleotide purine or pyrimidine bases. As used herein, "unmodified" (or "natural") nucleobases include the purine bases adenine (A) and guanine (G), and the pyrimidine bases thymine (T), cytosine (C) and uracil (U). Modified nucleobases include other, for example, synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaacdenine.

The anti-sense compounds used in accordance with this invention may be conveniently and routinely made through the well-known technique of solid phase synthesis. For example, equipment for such synthesis is sold by several vendors including, for example, Applied Biosystems (Foster City, Calif.). Other means for such synthesis known in the art may also be employed. It is well known to use similar techniques to prepare oligonucleotides such as the phosphorothioates and alkylated derivatives.

Preferably, the AONs of the present invention contain phosphorothioate linkages to increase stability, facilitate cellular uptake and enable the AONs to induce exon skipping via sequence specific anti-sense mechanisms. Modifications of the antisense-oligonucleotides are advantageous because they would not rapidly destroyed by endogeneous factors when applied, as this is valid for naturally occurring nucleotide sequences. It is understood by one skilled in the art that naturally occurring oligonucleotides having one of the disclosed sequences can be used according to the invention. A preferred embodiment of the modification is a phosphorothioate modification.

The anti-sense oligonucleotide may anneal entirely to exon 9 or at least to a portion of exon 9. For purposes of this application, it is intended to cover the anti-sense oligonucleotides that would sufficiently induce exon 9 skipping. One skilled in the art would conveniently determine exon 9 skipping simply by measuring increases in the production of a soluble truncated IL-23Rα (Δ9) mRNA (SEQ ID NO: 4) and/or its translated product–a soluble truncated IL-23Rα (Δ9) protein (SEQ ID NO: 5).

Figure 28:
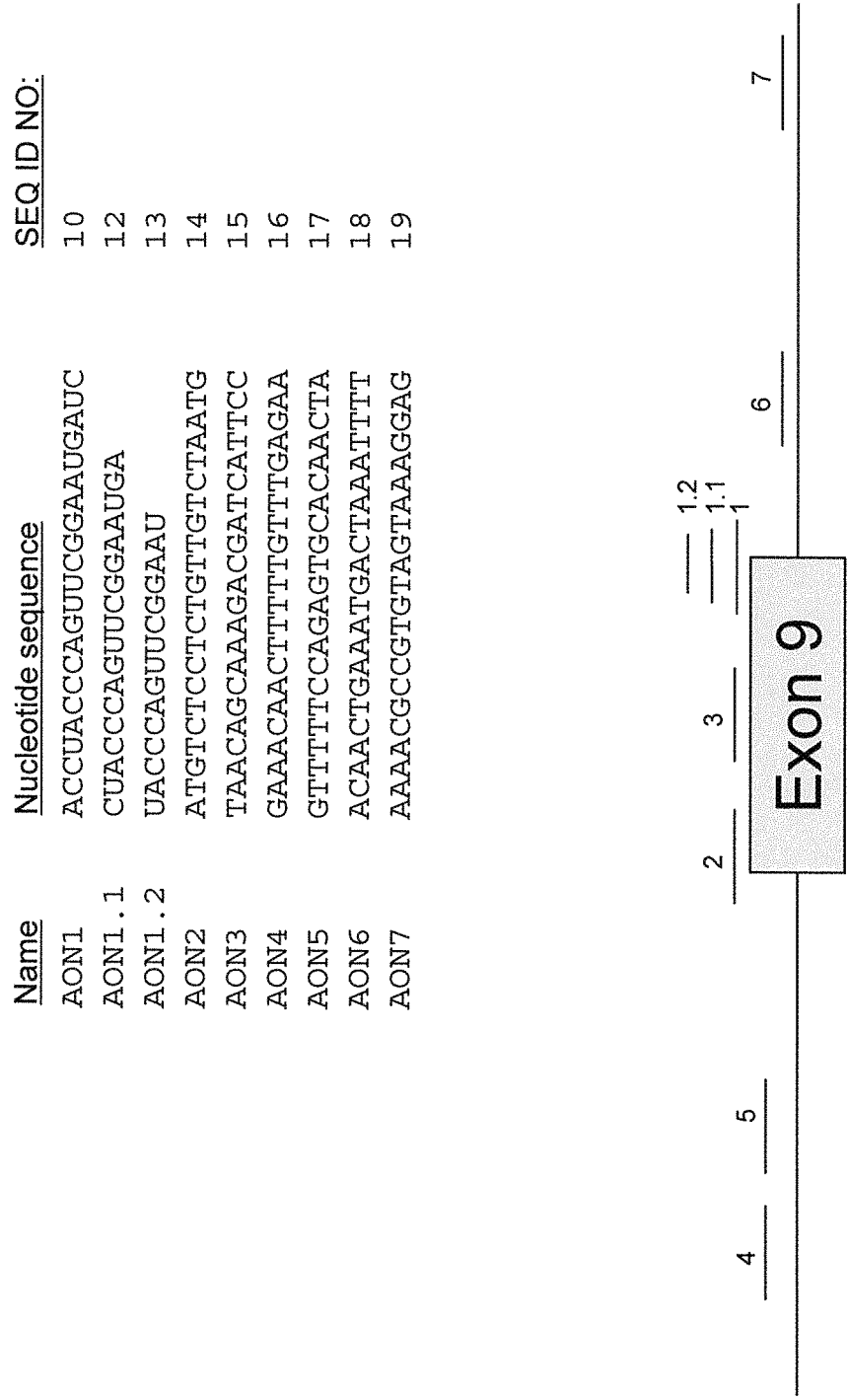
FIG. 28 depicts the nucleotide sequence and location of AONs (SEQ ID NOs: 10, 12-19) targeted against the exon 9 of the IL-23Rα.
Figure 29:
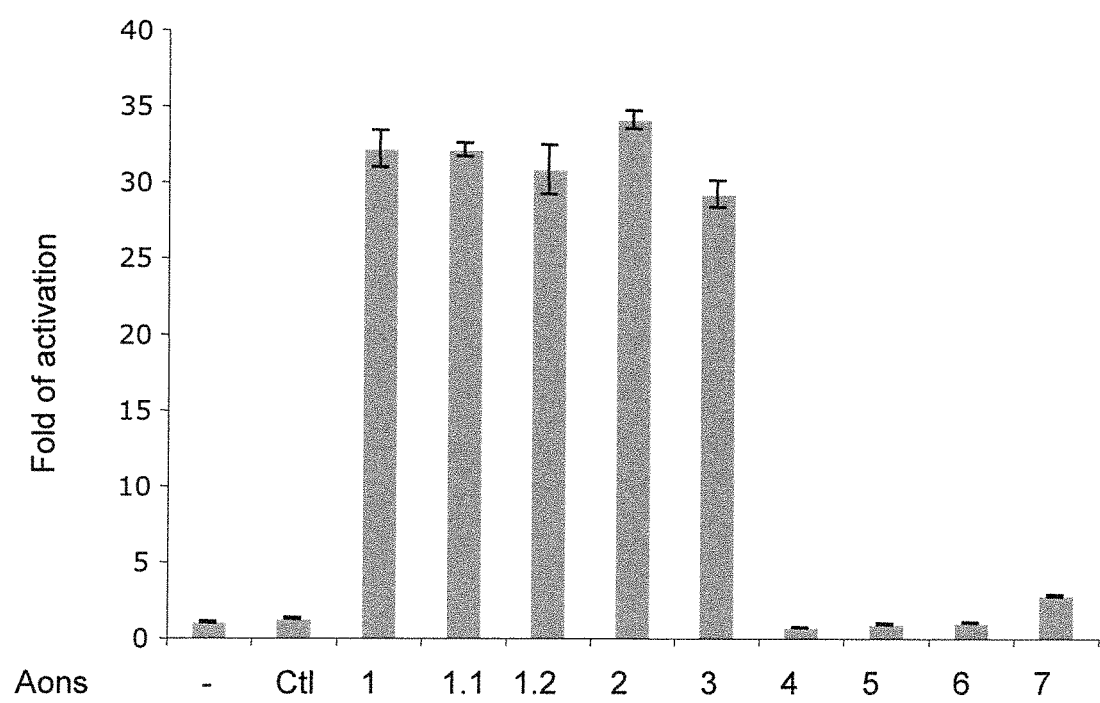
FIG. 29 depicts the effect of AONs on the exon 9 skipping in the mini-Gene. The mini-Gene was co-transfected with different AONs (50 pmole) into the 293T cells. The expression level of Exon8/10 (results from exon 9 skipping) was measured by qRT-PCR.

In one embodiment, AON2 (SEQ ID NO: 14) anneals to sixteen (16) nucleotides of the exon 9 (i.e., ACAACAGAGGAGACAT) and sufficiently induces exon 9 skipping, as evidenced by an increase in Δ9 production (See, FIG. 28 and FIG. 29).

In another embodiment, AON3 (SEQ ID NO: 15) anneals to twenty-two (22) nucleotides of exon 9 (i.e., GGAAT-GATCGTCTTTGCTGTTA) and sufficiently induces exon 9 skipping, as evidenced by an increase in Δ9 production (See, FIG. 28 and FIG. 29).

In another embodiment, AON1 (SEQ ID NO: 10) anneals to sixteen (16) nucleotides of exon 9 (i.e., GATCATTC-CGAACTGG) and sufficiently induces exon 9 skipping, as evidenced by an increase in Δ9 production (See, FIG. 28 and FIG. 29).

In another embodiment, AON1.1 (SEQ ID NO: 12) anneals to fourteen (14) nucleotides of exon 9 (i.e., TCAT-TCCGAACTGG) and sufficiently induces exon 9 skipping, as evidenced by an increase in Δ9 production (See, FIG. 28 and FIG. 29).

In yet another embodiment, AON1.2 (SEQ ID NO: 13) anneals to twelve (12) nucleotides of exon 9 (i.e., ATTC-CGAACTGG) and sufficiently induces exon 9 skipping, as evidenced by an increase in Δ9 production (See, FIG. 28 and FIG. 29).

In one preferred embodiment, the present invention provides an anti-sense oligonucleotide selected from the group consisting of SEQ ID NO: 10, SEQ ID NO: 12, SEQ ID NO: 13, SEQ ID NO: 14, and SEQ ID NO: 15.

The present invention further provides a pharmaceutical composition for alleviating inflammatory bowel disease in a subject which comprises an anti-sense oligonucleotide targeted against exon 9 of the IL-23Rα and a pharmaceutically acceptable carrier. Pharmaceutical acceptable carrier in the context of this invention means any pharmaceutical composition or formulation suitable for the administration of the anti-sense oligonucleotide.

Pharmaceutically acceptable carrier encompasses any of the standard pharmaceutical carriers. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Examples of pharmacologically acceptable carriers include aqueous solutions such as water, saline, or buffers solutions. Delivery vehicles include, for example, liposomes, microspheres, or emulsions. Delivery vehicles can be utilized to enhance in vivo stability. In a preferred embodiment, liposomes can be used as a delivery vehicle because of their ability to enhance intracellular delivery, long circulation half-lives, ease of incorporation of receptor targeted molecules, and minimal toxicity and good biodegradability. Liposomes may be made by a variety of techniques known in the art. These methods generally involve first dissolving and mixing the lipids in an organic solvent, followed by evaporation. Then an appropriate amount of the aqueous phase is mixed with the lipid phase, and then allowed to incubate for a sufficient time for the liposomes to form. In an embodiment, the pharmaceutical composition is suitable for administering a nasal route to a subject. An example includes aerosolized solution.

Routes of administration include, but are not limited to, intra-arterial, intra-venous, buccal, intra-muscular, nasal, oral, pulmonary inhalation (e.g., by inhalation or insufflation of powders or aerosols, including by nebulizer), subcutaneous, transdermal, and the like. The exact dosage and number of doses of the pharmaceutical compositions described herein depends upon several factors such as the disease indication, the route of administration, the delivery vehicle and the oligonucleotide composition. Dosage optimization may be conveniently achieved by measuring effectiveness of elevating the plasma level of Δ9 protein and reduction of the inflammation mediated by IL-23R.

In one embodiment, subject doses of the anti-sense oligonucleotides described herein may range from about 0.05 μg/kg to about 500 mg/kg, preferred about 1 μg/kg to about 100 mg/kg, and more preferred from about 100 μg/kg to about 50 mg/kg per administration. Typically, dosage for oral administration is higher (likely due to some degradation). For example, oral dosages may be up to 1 mg/kg or even up to about 5 mg/kg. Duration of treatment will depend on the effects of the treatment on the disease symptoms, and may be given hourly, daily, weekly, or monthly depending on the mode of application as well as multiple daily doses for extended periods of time.

Th17 cells represent a novel, distinct subset of CD41+ T-helper cells. Differentiation of naive human CD4+ T cells to Th17 cells is recognized to have critical functions in autoimmune disease models in mice. Evidence indicates that mice deficient in p19, the unique subunit of IL-23, demonstrated resistance in different autoimmune disease models, mainly because of the absence of T cells producing IL-17 (i.e., Th17 cells). Differentiation of Th17 cells in vivo requires the presence of IL-23, which is secreted by activated antigen-presenting cells. It is well that IL-23 per se cannot induce the differentiation of naive CD4+ T cells into Th17 cells in vitro, but may synergies with Th17 cell differentiation agents including IL-1, IL-6 and TGF-& to induce expression of IL-17 cytokine.

According to one embodiment, the present invention provides a therapeutic application of an anti-sense oligonucleotide targeted against exon 9 of the IL-23Rα and hence leads to formation of a soluble truncated IL-23Rα (e.g., Δ9) protein. Because Δ9 protein has the capability of inhibiting the cell signaling mediated by IL-23 as well as inhibiting the maturation of Th17 cells, the present inventors believe that anti-sense oligonucleotide against exon 9, when administered, would lead to formation of Δ9 which then behave as an inhibitor to inhibit the IL-23-mediated cell signaling (e.g., production of IL-17A and IL-17F) and Th17 maturation, and thus alleviating the development and progression of Th17-associated diseases such as inflammatory bowel diseases that include Crohn's disease.

In one embodiment, the present invention provides an anti-sense oligonucleotide that leads to formation of a soluble truncated IL-23Rα that inhibits the secretion of IL-17A and IL-17F. IL-23 is the key element in the final stages of Th-17 phenotypic maturation. In the present Th-17 maturation assays, naive CD4+ T cells were successfully differentiated to Th17 cells, based on their up-regulation of RORyt (the signature transcription factor for this cell subtype), and secretion of IL-17A and IL-17F. The induction of IL-17A and F expression was abolished when Δ9 was present is consistent with the observation that Δ9 did not affect changes in RORyt expression level. These results reinforce our hypothesis that Δ9 protein can function as a naturally-occurring specific inhibitor of IL-23 which has the ability to regulate Th-17 cell development.

In one embodiment, the present invention provides that the use of an anti-sense oligonucleotide against exon 9 of the IL-23Rα that would lead to formation of Δ9 and suppress the secretory phenotype of human Th17 cells, demonstrating the existence of a novel regulatory mechanism for human Th17 cells. The present findings have practical utility for the therapeutic application of the anti-sense oligonucleotide against exon 9 through formation of Δ9 protein. Specifically, anti-sense oligonucleotide against exon 9 may be used as a therapeutic agent for treating human Th17-dependent conditions such as Crohn's Disease, asthma and psoriasis. Many attempts have been made based on the premise that IL-23 is a target for anti-inflammatory therapies, particularly in the intestine; the present finding adds that anti-sense oligonucleotide against exon 9 may represent a novel therapeutic tool in this field.

Therefore, one aspect of the present invention relates to a method of anti-sense therapy, the method comprising the step of administering to a mammal in need thereof, an effective therapeutic (or prophylactic) amount of at least one anti-sense oligonucleotide as disclosed in this application. This method is particularly useful for preventing and/or treating inflammatory bowel diseases such as Crohn's disease.

The present invention provides a method of treating or alleviating inflammatory bowel disease in a subject which comprises administering to the subject an amount of any of the aforementioned compositions comprising the invented purified proteins, said amount effective to block IL-23 cell signaling in the subject. A subject may be a mammal, for example, a human. As mentioned above, the amount of anti-sense oligonucleotide present in the composition of the present invention is a therapeutically effective amount. A therapeutically effective amount of anti-sense oligonucleotide is that amount necessary so that the oligonucleotide performs its biological function without causing, into the host to which the composition is administered, overly negative effects. The exact amount of anti-sense oligonucleotide to be used may be conveniently determined by one skilled in the art. The present composition to be administered will vary according to factors such as the oligonucleotide biological activity, the type of condition being treated, the mode of administration, as well as the other ingredients in the composition.

The present composition may further include other anti-inflammatory compounds that are useful in the treatment of inflammatory bowel diseases. An exemplary compound may include recombinant soluble Δ9 protein, antibodies against IL-23, or IL-23R and the like.

The present invention will be better understood from the following experimental studies. One of ordinary skill in the art would readily appreciate that the specific methods and results discussed therein are for illustrative purposes only, and are not intended to limit the scope of the present invention. The experimental studies merely serve illustrative purposes, and the invention is more fully described by the claims which follow thereafter.

EXPERIMENTAL STUDIES

Example 1 SNP rs11209026

A) Protection Against Crohn's Disease

In a 2003 genome-wide association studies (GWAS), a significant association was found between Crohn's disease and a SNP (rs11209026) present on the IL-23Rα gene on chromosome 1 p31. The rs11209026 is located on exon 9 at nucleotide position 1142 of IL-23Rα, and it results in nucleotide change at position 1142 from G to A, amino acid change at 381 from Arg (R) to Gln (Q) (FIG. 1). The rs11209026 allele is found to confer strong protection against Crohn's disease, as well as other inflammatory diseases including psoriasis, ankylosing spondylitis and graft-versus-host disease.

B) IL-23Rα Genomic Organization

Figure 2:
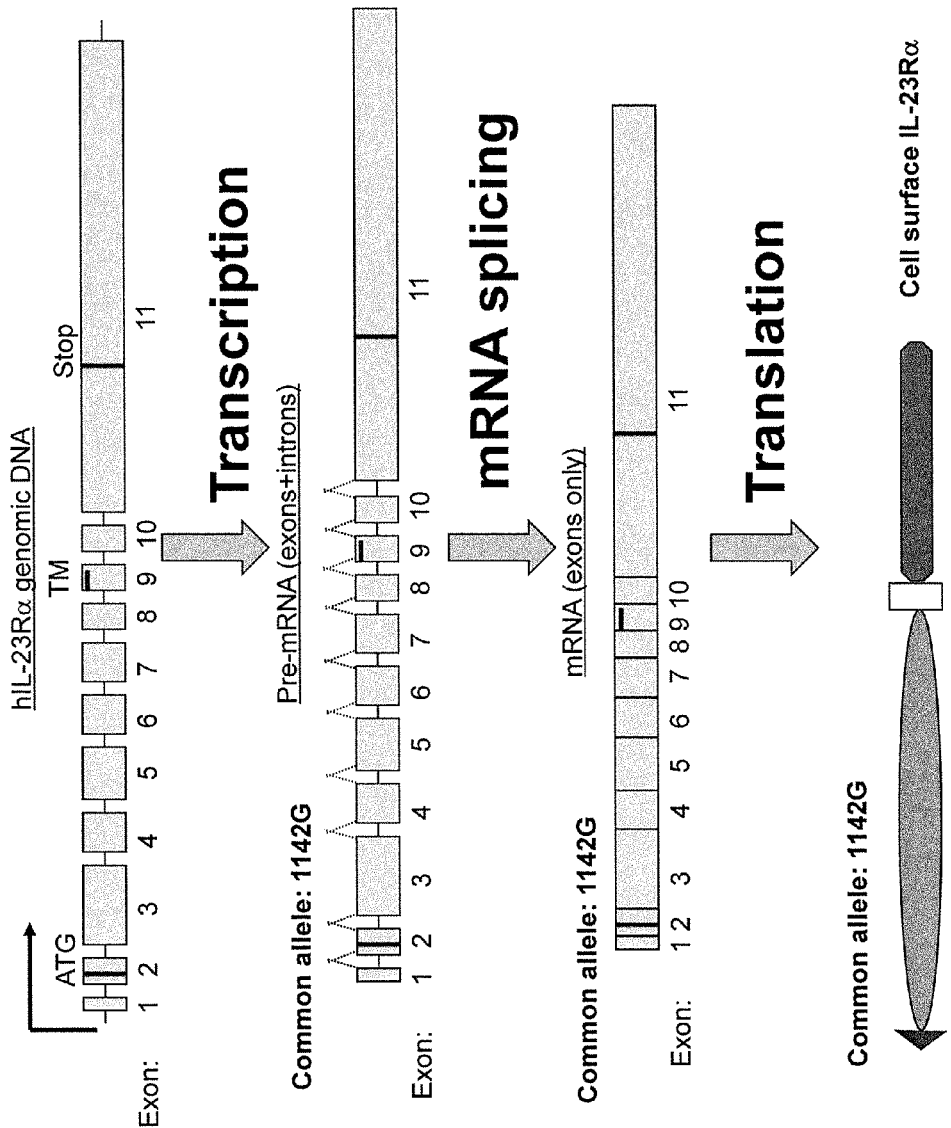
FIG. 2 depicts the expression of IL-23Rα when the common allele sequence is present in the IL-23Rα gene (1142G). First, transcription starts to produce pre-mRNA, which includes exons and introns. During mRNA maturation, RNA splicing occurs to join all the exons to form mRNA. Then, protein translation starts and results in expression of cell surface IL-23Rα protein.

IL-23Rα gene contains a total of 11 exons (i.e., exons 1-11) (See, FIG. 1 and FIG. 2). The IL-23Rα gene is first transcribed as pre-mRNA, which contains all the exons and introns. Upon mRNA maturation, mRNA splicing occurs, resulting in the removal of all the introns and joining of all the exons to become mRNA.

IL-23Rα protein translation starts at exon 2 and ends in exon 11 (FIG. 1). The mature IL-23Rα protein is a type-I cell surface membrane protein, containing a single-pass transmembrane domain encoded by exon 9. The IL-23Rα protein has a signal peptide followed by the extracellular domain, which is responsive for the binding to IL-23 cytokine. The protein also contains the cytoplasmic domain for intracellular signaling upon cytokine stimulation.

Example 2 Mini-Gene Constructs

A) Mini-Gene Constructs Containing Genomic DNA from Exon 8 To Exon 10 of IL-23Rα: Common Allele 1142G We sought to determine if rs11209026 affects alternative splicing of the IL-23Rα. To do so, we created expression constructs (i.e., Mini-Gene) containing genomic region (i.e., the exons 8, 9 and 10, and introns 8 & 9) of the IL-23Rα gene. However, the large size of the IL-23Rα introns (e.g., intron 9 is around 93 kb) rendered it impossible to perform PCR cloning or site-directed mutagenesis to introduce the SNP rs11209026 into the full-length IL-23Rα gene.

Figure 3A:
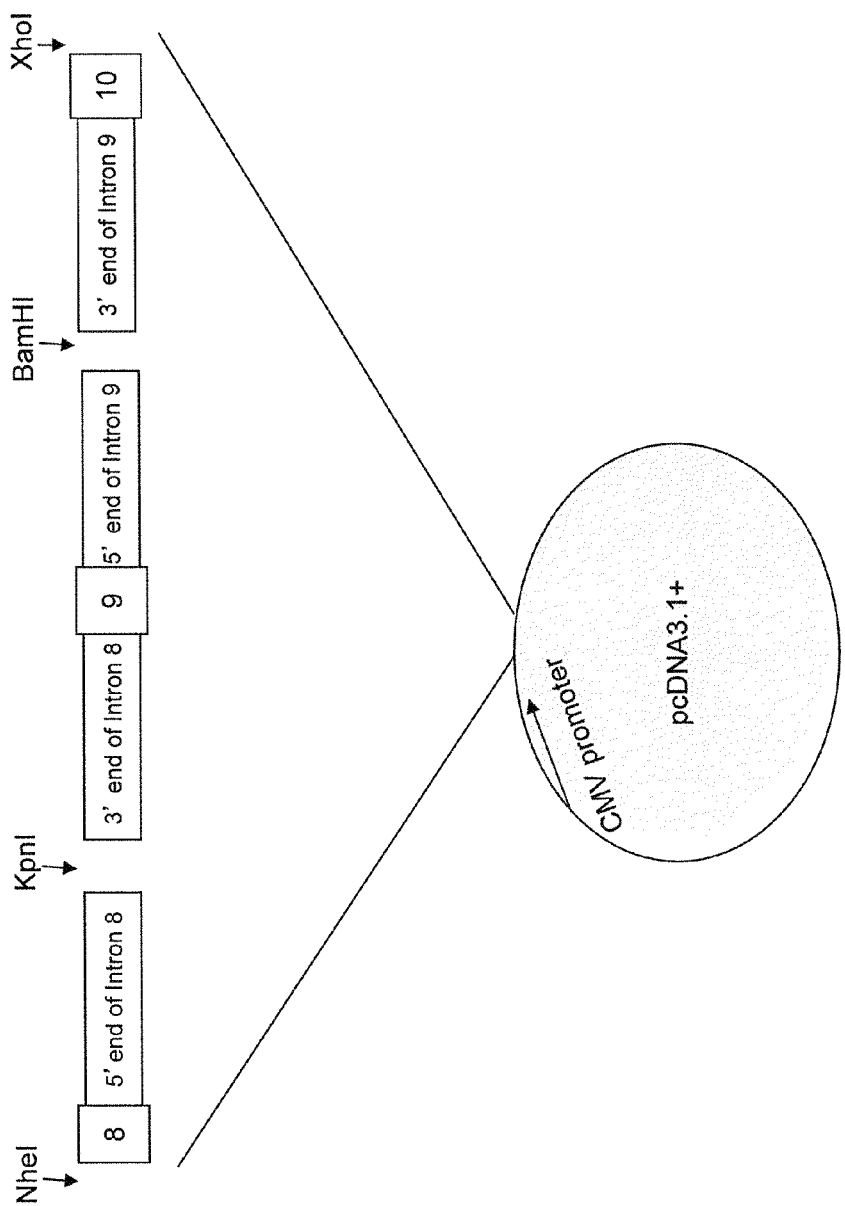
FIG. 3A depicts the schematic representation of human mini-gene plasmid. The mini-gene plasmid contains the exon 8, exon 9 and exon 10. Intronic sequences, intron 8 and intron 9, between these exons are also included. Since the sizes of intron 8 and intron 9 are large (i.e., intron 8>3 KB and intron 9>15 KB), internal deletion is made for these two introns. The corresponding size of intron used in the mini-gene is shown. The mini-gene was constructed by PCR. The restriction enzymes used in the cloning were shown in the figure. The mini-gene plasmid was verified by DNA sequencing. This mini-gene contains the common allele sequence 1142G on exon 9.

We circumvented the difficulty by constructing a Mini-Gene plasmid that contains the genomic sequence from the start of exon 8 to the end of exon 10 (FIG. 3A) of IL-23Rα using PCR. Three (3) PCR were performed to amplify three (3) fragments of IL-23Rα gene (FIG. 3A). The first IL-23Rα gene fragment contains the genomic sequence of exon 8 and 5' end of intron 8 (FIG. 3B) (SEQ ID NO: 1). The second IL-23Rα gene fragment contains the genomic sequence of 3' end of intron 8, exon 9 and 5' end of intron 9 (FIG. 3C) (SEQ ID NO: 2). The third IL-23Rαgene fragment contains the genomic sequence of 3' end of intron 9 and exon 10 (FIG. 3D) (SEQ ID NO: 3).

All the IL-23Rα gene fragments were ligated in its sequential order (i.e., exon 8—exon 9—exon 10) and subcloned into the pcDNA 3.1 using the restriction enzymes illustrated in the FIG. 3A. The Mini-Gene was under the control of a CMV promoter (See, Method). The Mini-Gene does not contain the entire intron 8 and 9 of the IL-23Rα in order to minimize the size of the plasmid. We kept only the intronic regions that contained the essential elements, including the 5' splice donor site, "A" branch point and 3' splice acceptor site, so as to allow IL-23Rα mRNA splicing (FIGS. 3B, 3C and 3D).

B) Mini-Gene Construct And Expression of Exon 8/9/10 and Exon 8/10 Transcripts i) Presence of mRNA Transcripts for Exon 8/9/10 and Exon 8/10.

Figure 4:
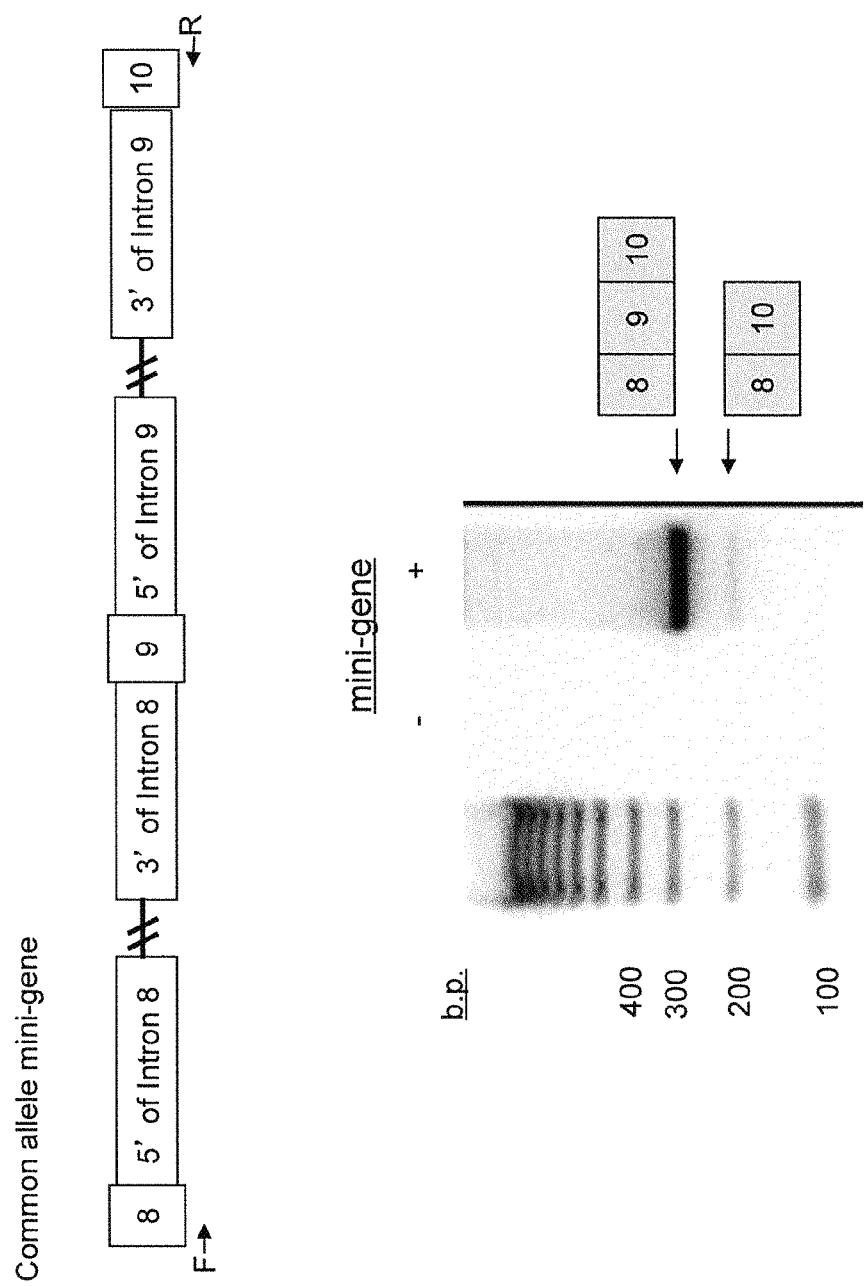
FIG. 4 depicts the expressions of exon 8/9/10 and exon 8/10 mRNAs by the common allele mini-gene. 293T cells were transfected with either control vector or the mini-gene. RNA was prepared and reverse transcribed into cDNA. Expressions of exon 8/9/10 and exon 8/10 were measured by RT-PCR.

We transfected 293T cells with control vector or the Mini-Gene construct using Fugene HD (Roche). Using RT-PCR, we monitored the basal expression of exon 8/9/10 and exon 8/10 (i.e., exon 9 was skipped) transcripts in the transfected 293T cells (FIG. 4). RNA was isolated 24 hours after transfection using RNA mini-prep kit (Stratagene). The isolated RNA was reverse transcribed into cDNA using AffinityScript cDNA synthesis kit (Stratagene).

The expressions of exon 8/9/10 and exon 8/10 transcripts were measured by RT-PCR using the following primer pair:

```
Forward primer (F):
                                      (SEQ ID NO: 20)
TCCCCAGGTCACATCAAAAG Reverse primer (R):
                                      (SEQ ID NO: 21)
TTCACAACATTGCTGTTTTTCA
```

As shown in FIG. 4, transfection of the mini-gene constructs carrying the common allele 1142G leads to a predominate expression of exon 8/9/10 mRNA transcripts, and a weak expression of the exon 8/10 transcript. These data indicate that there is an intrinsic low expression of exon 8/10 mRNA transcript, confirming a minimal basal activity of exon 9 skipping in the IL-23Rα.

ii) Quantification of mRNA Transcripts for Exon 8/9/10 and Exon 8/10.

Figure 5:
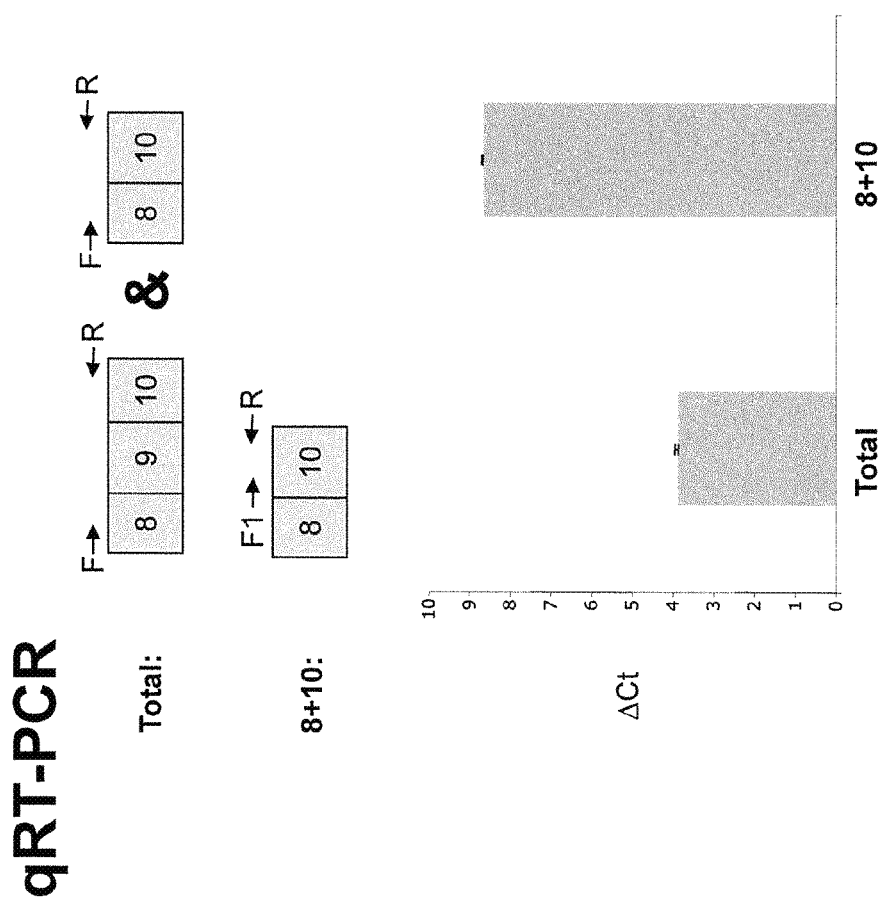
FIG. 5 depicts the expressions of exon 8/9/10 and exon 8/10 mRNAs by the common allele mini-gene. 293T cells were transfected with either control vector or the mini-gene. RNA was prepared and reverse transcribed into cDNA. Expressions of exon 8/9/10 and exon 8/10 were measured by real-time qRT-PCR.

We transfected 293T cells with control vector or the Mini-Gene construct using Fugene HD (Roche). Using qRT-PCR, we quantitatively measured the expression level of total mRNA transcripts (i.e., exon 8/9/10 and exon 8/10) and exon 8/10 (i.e., exon 9 was skipped) transcript in the transfected 293T cells (FIG. 5).

Expression level of total mRNA transcripts (exon 8/9/10 and exon 8/10) was measured by qRT-PCR using the following primers:

```
Forward primer (F):
                             (SEQ ID NO: 20)
TCCCCAGGTCACATCAAAAG Reverse primer (R):
                             (SEQ ID NO: 21)
TTCACAACATTGCTGTTTTCA
```

The following pair of primers only measured the expression level of exon8/10:

```
Forward primer (F1):
                             (SEQ ID NO: 22)
GGCACCTTACTTCTGGATTAAAAG Reverse primer (R):
                             (SEQ ID NO: 21)
TTCACAACATTGCTGTTTTCA
```

As shown in FIG. 5, transfection of the mini-gene showed weak expression of a transcript joining exons 8 and 10 together (FIG. 5). This observation showed that there was a basal activity of exon 9 skipping, which results in the production of mRNA transcript containing exons 8 and 10.

Example 3 Mini-Gene Containing Allele 1142A

A) Mini-Gene Constructs Containing Uncommon Variant Allele 1142A (rs11209026)

Figure 6:
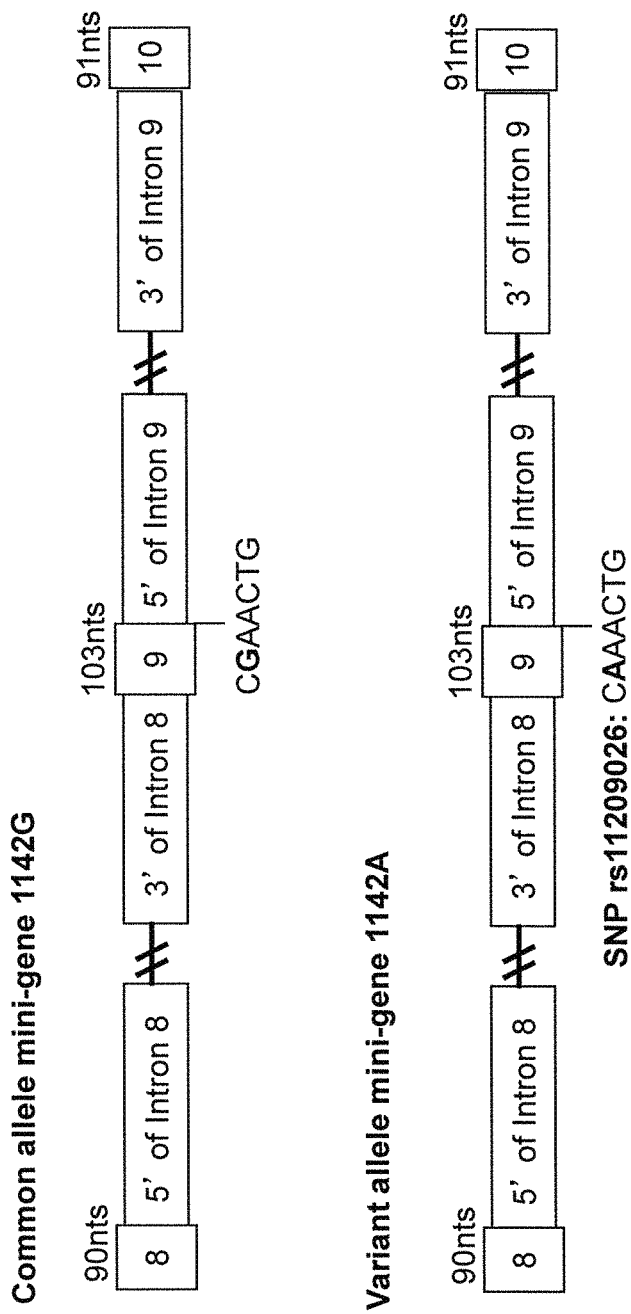
FIG. 6 depicts the schematic representation of human mini-genes carrying either the common allele (1142G) or variant allele (1142A) on exon 9. Variant allele mini-gene was generated by PCR-mediated site directed mutagenesis. The plasmid was verified by DNA sequencing.

We used PCR approach to perform site directed mutagenesis in the mini-gene containing exon 8/9/10 to introduce the SNP 1142A into the mini-gene as described above in Example 2. Using this approach, we prepared two (2) mini-gene constructs: one carrying the common allele 1142G and the other carrying the uncommon allele 1142A (rs11209026) (FIG. 6).

B) Mini-Gene Constructs And Expression of Exon 8/9/10 and Exon 8/10 Transcripts

We transfected 293T cells with the two mini-gene constructs using Fugene HD (Roche). RNA was prepared after 24 hours of transfection using RNA miniprep kit (Stratagene). The isolated RNA was reverse transcribed into cDNA using AffinityScript cDNA synthesis kit (Stratagene). Expressions of exon 8/9/10 and exon 8/10 were measured by RT-PCR and qRT-PCR using the same primer pair sets as described above (Example 2) to monitor the expressions of exon 8/9/10 and exon 8/10 (FIG. 7).

Figure 7:
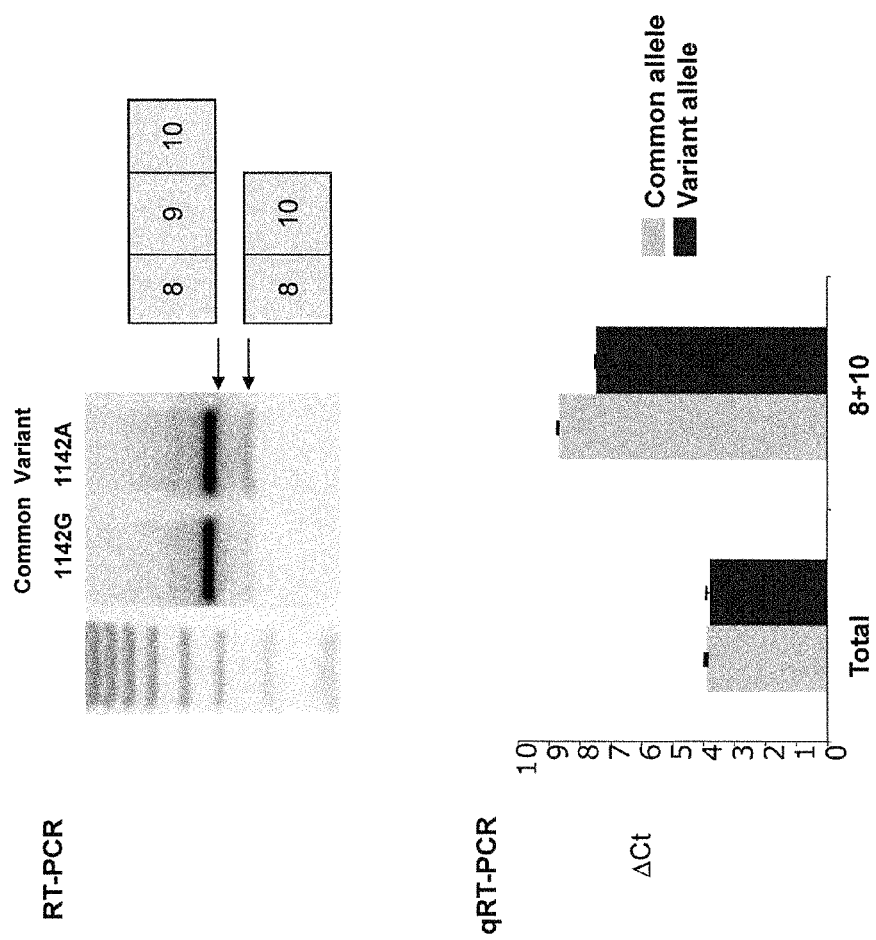
FIG. 7 depicts the effect variant allele on exon 9 splicing. Common allele "G" and variant allele "A" mini-gene plasmids were transfected into the 293T cells. RNA was prepared 24 hours post-transfection and was reverse transcribed into cDNA. The expression levels of two mRNA transcripts, exon 8/9/10 and exon 8/10, were measured by RT-PCR (Top) and real-time qRT-PCR (Bottom). The results clearly showed that the mini-gene plasmid carrying the variant allele "A" expressed higher level of exon8/10 transcript than the plasmid containing the common allele.

Transfection of these two mini-gene constructs showed similar expression levels of total transcripts (exon 8/9/10 and exon 8/10) (FIG. 7 Bottom). However, mini-gene carrying 1142A (rs11209026) showed ~2 fold (~1 Ct difference) increase expression of exon 8/10 mRNA transcripts when compared to the mini-gene carrying the common allele (1142G). This observation confirms that rs11209026 plays a role in exon 9 splicing. The presence of rs11209026 reduces the efficiency of exon 9 splicing and consequently causes exon 9 skipping. Exon 9 skipping results in an increased expression of exon 8/10 mRNA transcripts. Altogether, these data suggest that the rs11209026 allele may disrupt the splice enhancer binding site on exon 9 and thus reduces exon 9 splicing.

Figure 8A:
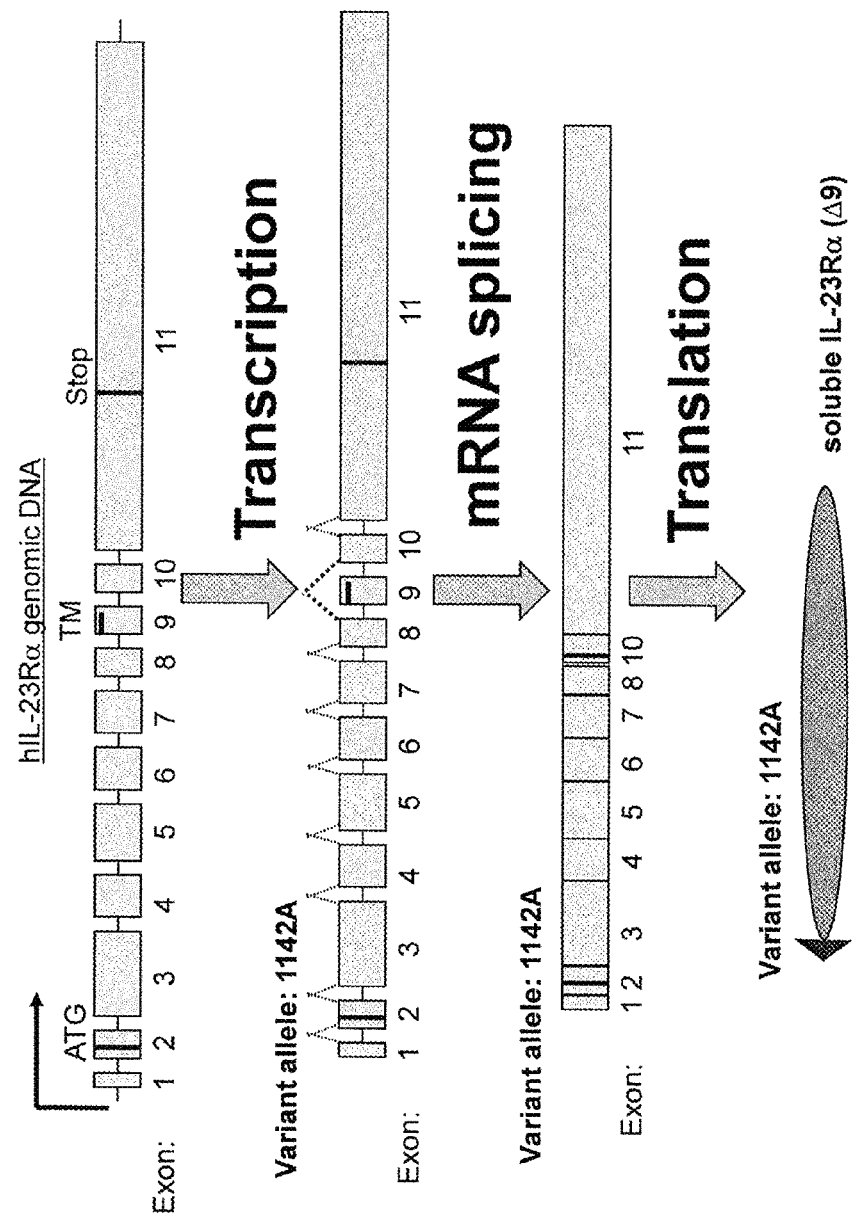
FIG. 8A depicts the hypothetical model of the function of variant allele (SNP rs11209026) (1142A) during exon 9 splicing of IL-23Rα. First, transcription starts to produce pre-mRNA, which includes exons and introns. During mRNA maturation, RNA splicing occurs to join all the exons to form mRNA. However, variant allele on exon 9 causes aberrant exon 9 splicing, which results in exon 9 skipping. Consequently, the exon 9 is missing in the IL-23Rα mRNA. Joining between exon 8 and 10 results in open reading frameshift and introduces pre-mature translational termination signal on exon10. As a result, protein translation starts normally at exon 2 but ends pre-maturely at exon 10, which result in the expression of soluble IL-23R protein (Δ9). This Δ9 splice variant contains almost the entire extracellular domain with addition of 8 novel amino acids (GLKEGSYC (SEQ ID NO: 42)) at the c-terminus.

The IL-23Rα gene contains 11 exons and rs11209026 is located on exon 9 (FIG. 8). The gene is first transcribed as pre-mRNA, which contains all the exons and introns. Upon mRNA maturation, mRNA splicing takes place which results in the removal of all the introns and joining of all the exons to become mRNA. However, the rs11209026 disrupts the splice enhancer binding site, which causes exon 9 skipping. Therefore, expression of Δ9 mRNA transcript was increased. In the Δ9 mRNA, deletion of exon 9 results in the premature translational termination signal used on exon 10. The protein translation starts at exon 2 and ends in exon 10. The Δ9 protein belongs to naturally occurring soluble form of IL-23Rα and negatively regulates IL-23 receptor function.

The translated Δ9 protein has 356 amino acids and notably contains a unique eight (8) amino acid sequence at the C-terminus (FIGS. 8B and 8C). The entire nucleotide coding sequence and amino acid sequence are set forth in FIG. 8B as SEQ ID NO: 4 (nucleotide coding sequence) and SEQ ID NO: 5 (amino acid sequence). Because of the alternative translation reading frame used on exon 10 (resulted from the alterative splicing event), an extra eight (8) amino acids are uniquely present in the Δ9 protein, which is not present in the naïve full-length IL-23Rα protein (FIGS. 8B and 8C). This observation indicates that the amino acid sequence (GLKEGSYC SEQ ID NO: 42)) present in Δ9 is novel and unique to the Δ9 protein.

Example 4 rs11209026 Changes the Splice Enhancer Site Prediction Using ESE

Figure 9:
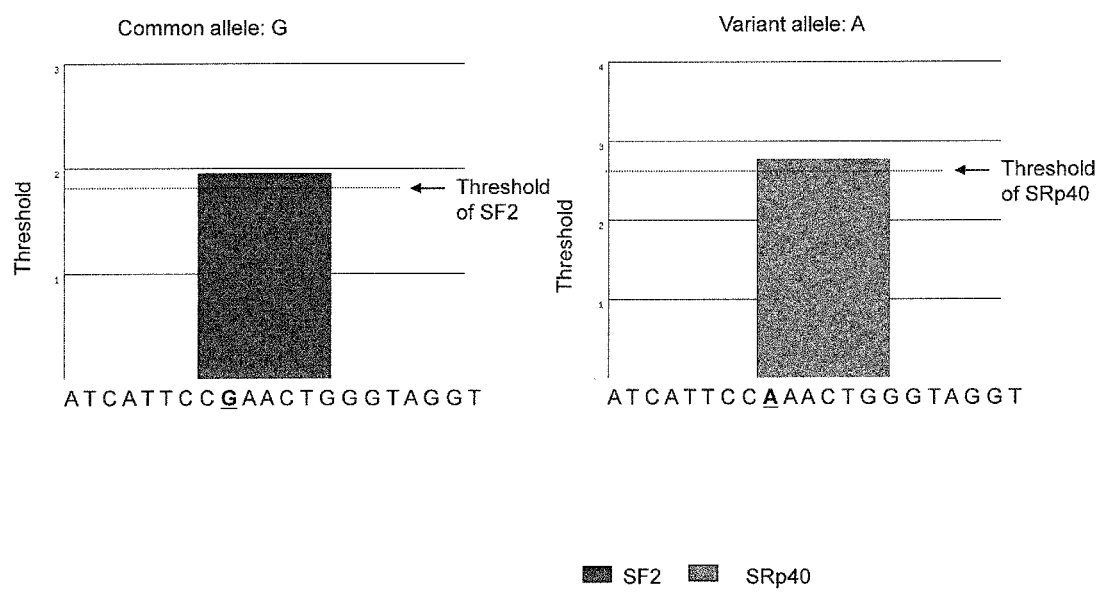
FIG. 9 depicts the predicted SF2 and SRp40 binding sites in the common allele "G" (SEQ ID NO: 44) and variant allele "A" (SEQ ID NO: 45) respectively using ESE finder program.

In this study, we examined if rs11209026 may disrupt the splice enhancer binding site, thus causes exon 9 skipping (i.e., reduced the efficiency of exon 9 splicing). To do so, we first employed an ESE (Exonic Splice Enhancer) finder program, a web-based prediction program, to predict the splice enhancer binding site (FIG. 9). Our analysis revealed binding sites of SF2 and SRp40 are predicted in the common allele "G" and variant allele "A" respectively (FIG. 9). Both SF2 and SRp40 proteins were found to belong to the SR protein family splice enhancer). Both SF2 and SRp40 have a modular structure containing two copies of an RPM (RNA recognition motif) at the N-terminus that provides RNA-binding specificity and a C-terminal RS domain that acts to promote protein-protein interactions, which facilitate recruitment of the spliceosome.

Example 5 SF2 Over-Expression (but not SRp40) Enhances Exon 9 Splicing in IL-23Rα

A) SF2 and SRP40 Expression Plasmids

In this study, we constructed expression plasmids containing SF2 and SRp40 in order to study their effects on exon 9 splicing. RNA was extracted from 293T cells using the RNA mini-prep kit (Stratagene). The isolated RNA was reverse transcribed into cDNA using AffinityScript cDNA synthesis kit (Stratagene). PCR was performed to obtain the DNA fragments encoded SF2 and SRp40 genes (from translational start "ATG" to translational stop) using the following primer pairs (FIGS. 10A and 10B).

```
SF2 F:
                                        (SEQ ID NO: 24)
ACAAGCTTGCCACCATGTCGGGAGGTGGTGTGATT

SF2 R:
                                        (SEQ ID NO: 25)
ATCTCGAGTTATGTACGAGAGCGAGATCT

SRp40 F:
                                        (SEQ ID NO: 26)
ACAAGCTTGCCACCATGAGTGGCTGTCGGGTATTC

SRp40 R:
                                        (SEQ ID NO: 27)
ATCTCGAGTTAATTGCCACTGTCAACTGA
```

The PCR fragments were sub-cloned into the mammalian expression vector (pcDNA3.1). The expression plasmids were verified by DNA sequencing.

B) SF2 Over-Expression (Rut not SRp40) Enhances Exon 9 Splicing

We next examined the effect of the SF2 (SEQ ID NO: 7) and SRp40 (SEQ ID NO: 9) proteins on exon 9 splicing. In this study, we co-expressed the common allele "1142 G" mini-gene constructs, together with SF2 or SRp40 expression constructs. Empty expression constructs were used as a negative control. RNA was prepared 48 hours post-transfection using RNA mini-prep kit (Stratagene). The isolated RNA was reverse transcribed into cDNA using AffinityScript cDNA synthesis kit (Stratagene). Expression of exon 8/10 were measured by qRT-PCR using the primers as described above (Example 2).

Over-expression of SF2 enhanced exon 9 splicing, and resulted in a reduction of exon8/10 expression. In contrast, over-expression of SRp40 did not have any significant effects (FIG. 10C).

Example 6 Knock-Down of SF2 Reduces the Exon 9 Splicing

A) siRNA Against SF2

Figure 11:
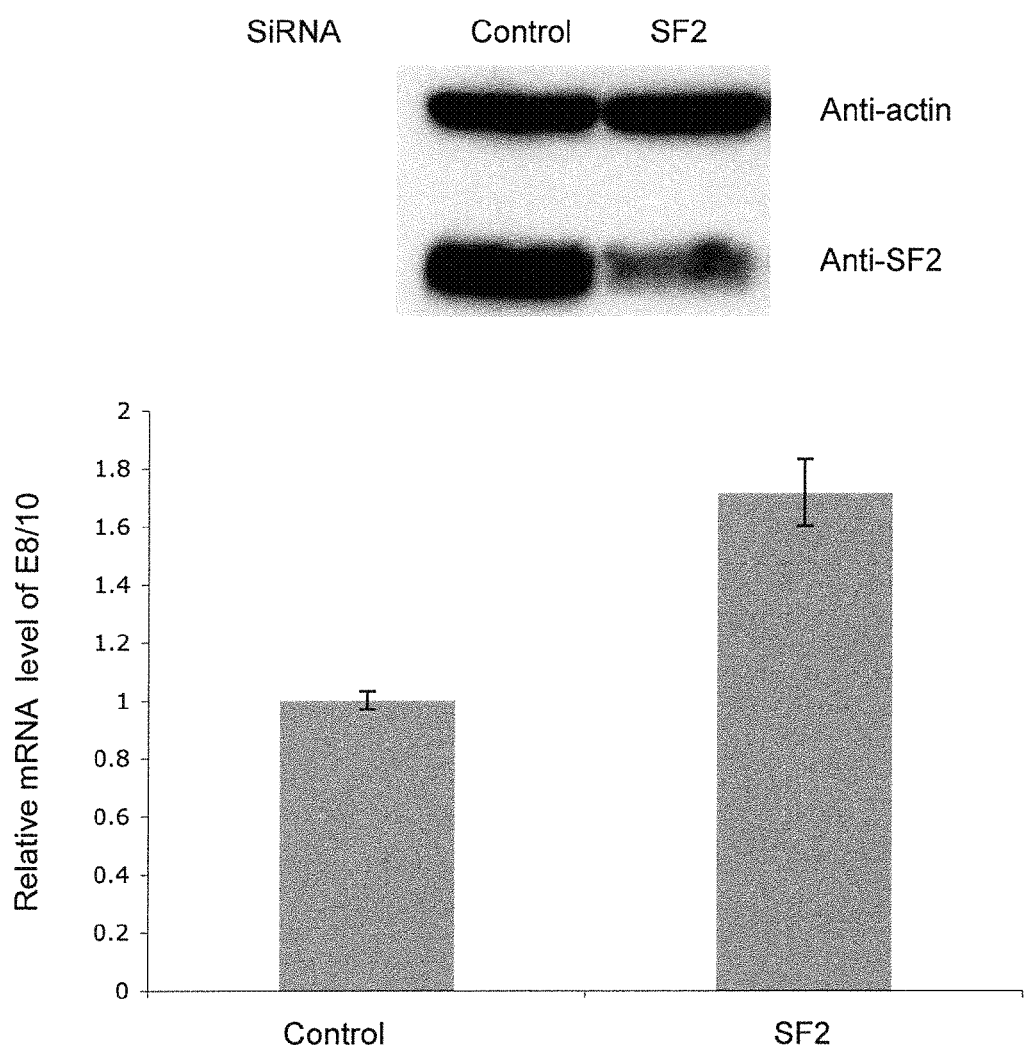
FIG. 11 depicts the effect of SF2 knockdown on exon 9 splicing. 293T cells were co-transfected with common allele mini-gene plasmid and control or SF2 siRNA. The top panel shows the successful knockdown of SF2 protein expression. Cell lysates were prepared 48 hours post-transfection. Immunoblot was performed using anti-actin and anti-SF2 antibodies. The bottom panel showed the expression level of exon8/10 transcript was quantitated by real-time qRT-PCR.

We sought another approach to identify the relationship between SF2 and exon 9 splicing. In Example 5, we over-expressed SF2 and found an enhancement of exon 9 splicing. In these series of studies, we employed siRNA against SF2 to knock-down SF2 expression. We used SF2 On-TARGETplus siRNA 3'UTR available from Dharmacon. The mini-gene construct plasmid was co-transfected with 20 pmole of control siRNA or SF2 siRNA into the 293T cells using Lipofectamine 2000 (Invitrogen). Transfected cells were collected 48 hours post-transfection and were separated into two equal parts. One part was used to prepare the protein lysates whereas the remaining part was used to prepare the RNA. The expression of SF2 protein was measured by immunoblot using anti-SF2 antibody (Santa Cruz). The anti-actin immunoblot was used as loading control (FIG. 11 Top). We showed that SF2 protein expression was reduced by the siRNA SF2.

B) SF2 siRNA Increases Expression of Exon 8/10

In this study, we measured the expression level of exon 8/10. RNA from transfected cells was isolated and reverse transcribed into cDNA using AffinityScript cDNA synthesis kit (Stratagene). Expression of exon 8/10 were measured by qRT-PCR using the primers as described in Example 2.

As shown in FIG. 11, reduced expression of SF2 enhanced exon 9 skipping (i.e., reduced exon 9 splicing), and increased the expression of exon 8/10 mRNA (FIG. 11 Bottom). The data confirms the SF2 function as splice enhancer during exon 9 splicing.

Figure 12:
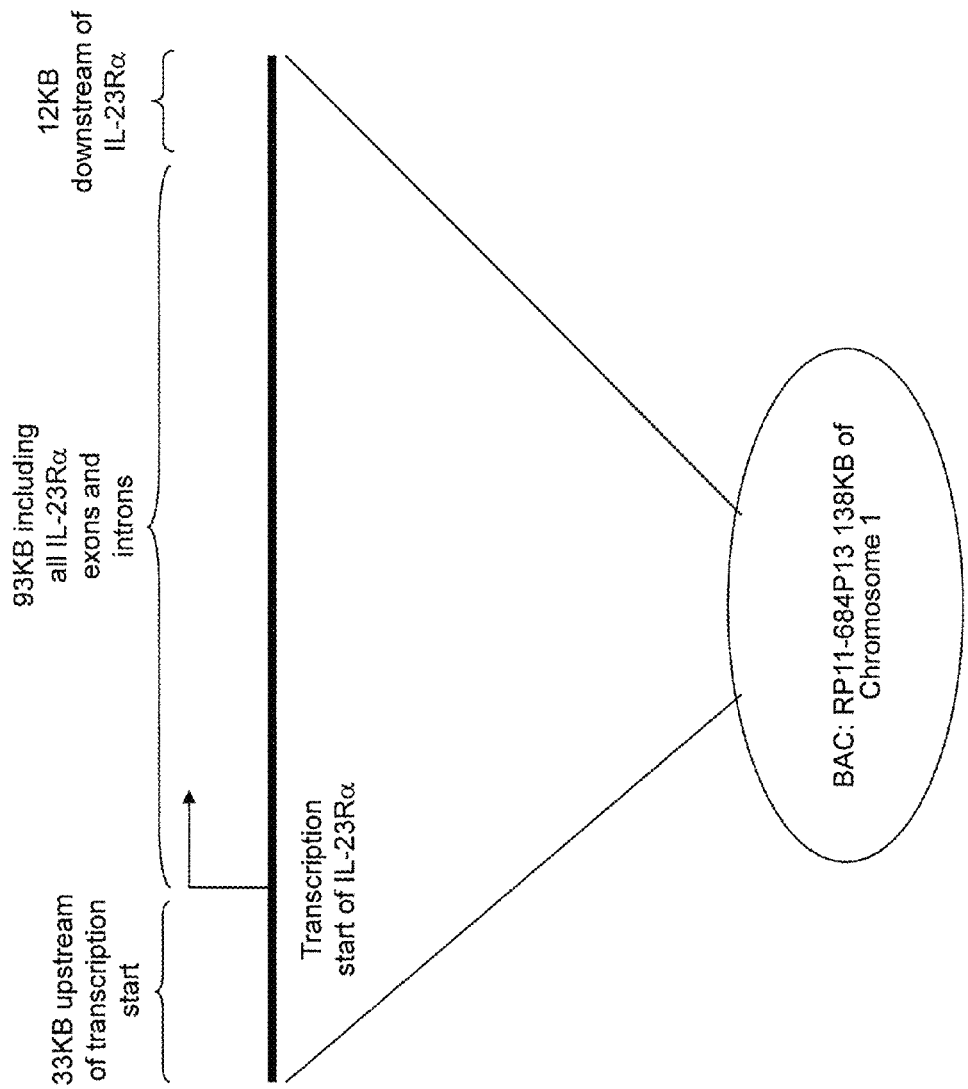
FIG. 12 depicts the schematic representation of BAC (Bacterial Artificial Chromosome) RP11-684P13. This BAC clone contains 138 KB of human chromosome 1 and covers the whole human IL-23Rα locus, which includes 33 KB DNA sequence upstream of the transcriptional start, 93 KB DNA sequence of introns and exons and 12 KB DNA sequence after the transcriptional stop.

Example 7 SF2 as Splice Enhancer During Exon 9 Splicing Using BAC Containing IL-23Rα Gene A) BAC Clones We obtained a BAC (Bacterial Artificial Chromosome) clone RP11-684P13 that contains a 138 Kb fragment of human chromosome 1 covering the entire human IL-23Rα locus. The 138 Kb fragment includes a 33 Kb DNA sequence upstream of the transcriptional start, 93 Kb DNA sequence of introns and exons and 12 Kb DNA sequence after the transcriptional stop (FIG. 12). The transcription of IL-23Rα gene was controlled by its own regulatory element containing in this BAC.

B) SF2 Over-expression (But not SRp40) Enhances Exon 9 Splicing in BAC

In order to confirm the effects of SF2 and SRp20 proteins on exon 9 splicing, BAC clones containing IL-23Rα gene were co-expressed with empty vector, SF2 or SRp40 expression constructs. RNA was prepared 48 hours post-transfection using RNA mini-prep kit (Stratagene). The isolated RNA was reverse transcribed into cDNA using AffinityScript cDNA synthesis kit (Stratagene). Expression of mRNA transcript missing exon 9 (Δ9) was measured by qRT-PCR using the following primers:

```
Forward primer (F1):
                                        (SEQ ID NO: 23)
GGCACCTTACTTCTGGATTAAAAG Reverse primer (Ex11R):
                                        (SEQ ID NO: 28)
AGGACCTGCTCACTGGAATTA
```

Figure 13:
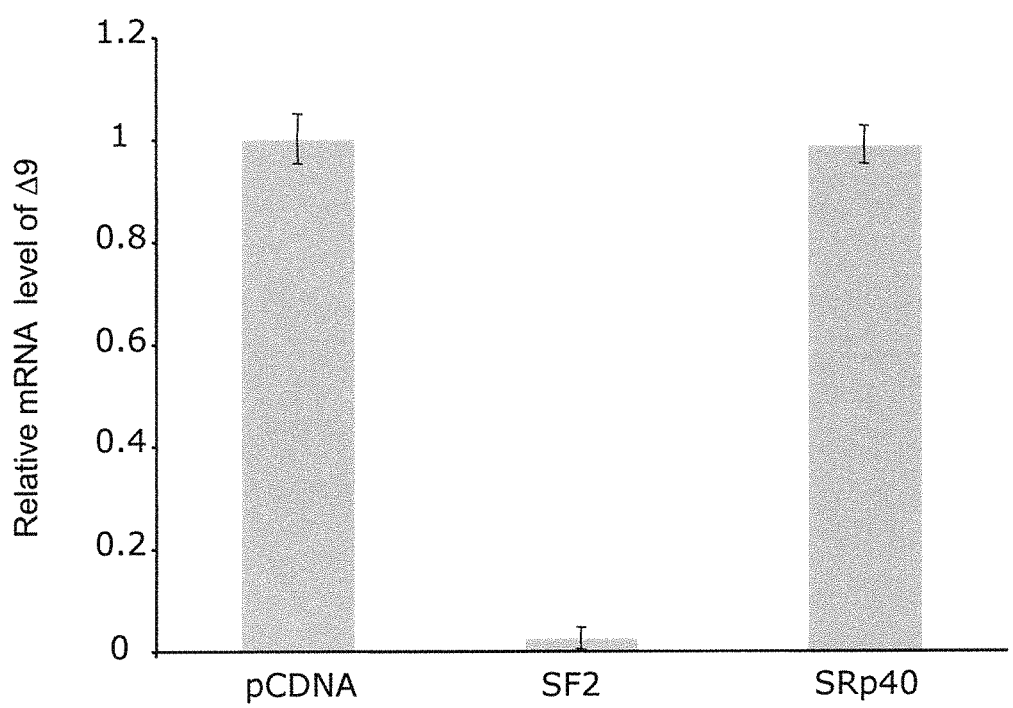
FIG. 13 depicts the effect of SF2 and SRp40 overexpression on exon 9 splicing using the BAC cells. 293T cells were co-transfected with the BAC clone and pcDNA or SF2 or SRp40 expression constructs. Expression level of exon8/10 transcript was quantitated by real-time qRT-PCR.

Over-expression of SF2 enhanced exon 9 splicing (i.e., reduced exon 9 skipping), and reduced exon8/10 expression. Over-expression of SRp40 showed little effect (FIG. 13). These data confirmed that SF2 functions as splice enhancer during exon 9 splicing.

Example 8 Over-Expression of SF2 Corrects Aberrant Exon 9 Splicing in the Mini-Gene Containing rs11209026 (1142A)

In Example 6, we showed that SF2 knock-down caused exon 9 skipping (i.e., increased expression of E8/10 transcript). The mini-gene carrying rs11209026 showed enhanced exon 9 skipping (see Example 3). In addition, the knockdown of SF2 protein mimics the effect of the SNP rs11209026 in exon 9 splicing. These observations implies that the mechanism of enhanced exon 9 skipping in the variant allele's mini-gene (rs11209026) may be due to a reduced binding affinity of SF2 on exon 9 of the pre-mRNA.

Figure 14:
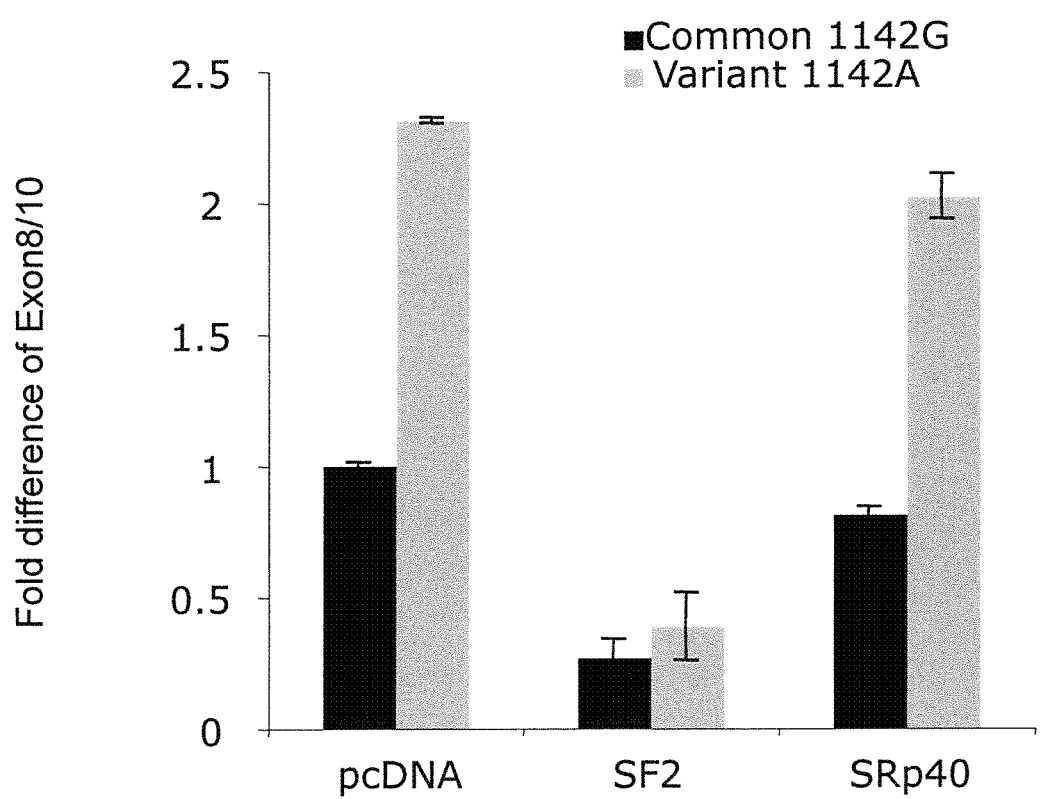
FIG. 14 depicts the effect of SF2 and SRp40 overexpression on exon 9 splicing using the common allele and variant allele mini-gene plasmids. 293T cells were co-transfected with common allele "G" or variant allele "A" mini-gene plasmid and pcDNA or SF2 or SRp40 expression constructs. Expression level of exon8/10 transcript was quantitated by real-time qRT-PCR.

In this study, we examined if SF2 over-expression may restore the exon 9 splicing. We co-transfected the expression constructs of SF2 or SRp40 with the common or variant allele's mini-gene constructs into the 293T cells (FIG. 14). Expression of exon 8/10 in the variant allele's mini-gene was increased by around 2 fold compared to that in the common allele's mini-gene (FIG. 14). Over-expression of SF2 minimized the difference of the expression of exon 8/10 in these two mini-genes (FIG. 14). In contrast, over-expression of SRp40 showed no effect (FIG. 14). These results indicate that over-expression of SF2 is capable to correct the aberrant exon 9 skipping in the variant allele's mini-gene. We conclude that the aberrant exon 9 skipping in the mini-gene carrying the variant allele (rs11209026) is due to the reduced binding of SF2, which functions as a splice enhancer during exon 9 splicing.

Example 9 rs11209026 "1142 A" Reduces the SF2 Binding on the Exon 9

A) Recombinant SF2

Figure 15:
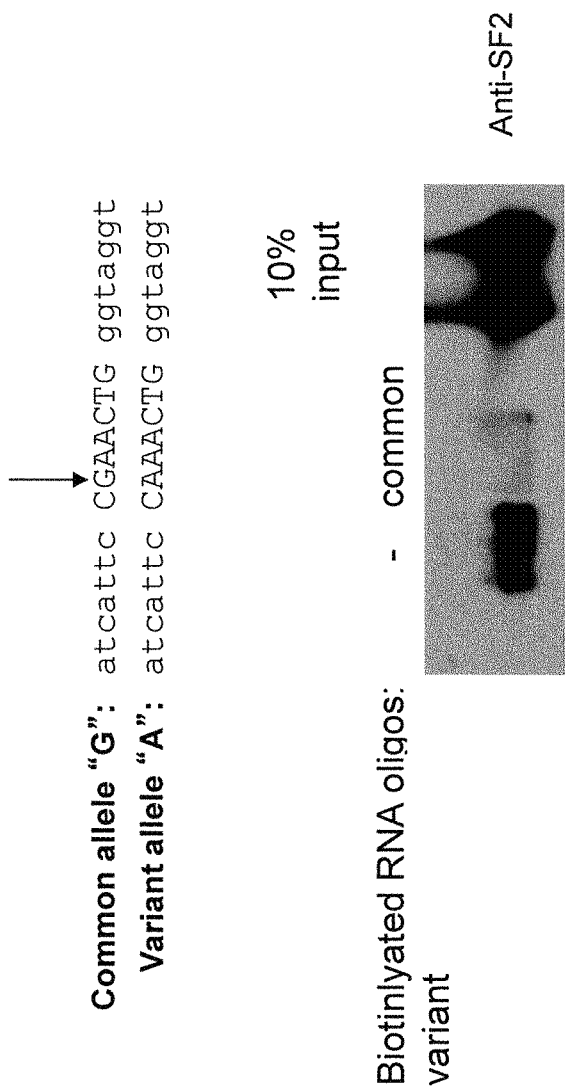
FIG. 15 depicts in vitro binding assay using biotin-labeled RNA oilgonucleotides. 100 ng biotinlyated RNA oligos containing either common allele "G" (SEQ ID NO: 44) or variant allele "A" (SEQ ID NO: 45) were incubated with purified recombinant SF2 protein. The biotinlyated RNA molecules were precipitated by streptavidinagarose. The amount of SF2 bound to the oligonucleotides was examined by immunoblot using anti-SF2 antibody.

In order to examine the SF2 binding affinity on the common allele and variant allele sequence, an oligonucleotide pull down experiment was performed (FIG. 15). Biotin-labeled RNA oligonucleotides (100 ng/reaction) containing either common allele "G" or variant allele "A" were incubated with the SF2 recombinant protein. The biotin-labeled RNA molecules were then precipitated by the streptavidin-agarose. The amount of SF2 bound to the RNA molecules in the precipitates were analyzed by the immunoblot using anti-SF2 antibody. SF2 was precipitated in the assay (FIG. 15). The SF2 protein bound weaker to the variant allele's (rs11209026,1142A) oligonucleotide than the common allele's (1142G) oligonucleotide.

B) 293T Cell Lysate

Figure 16:
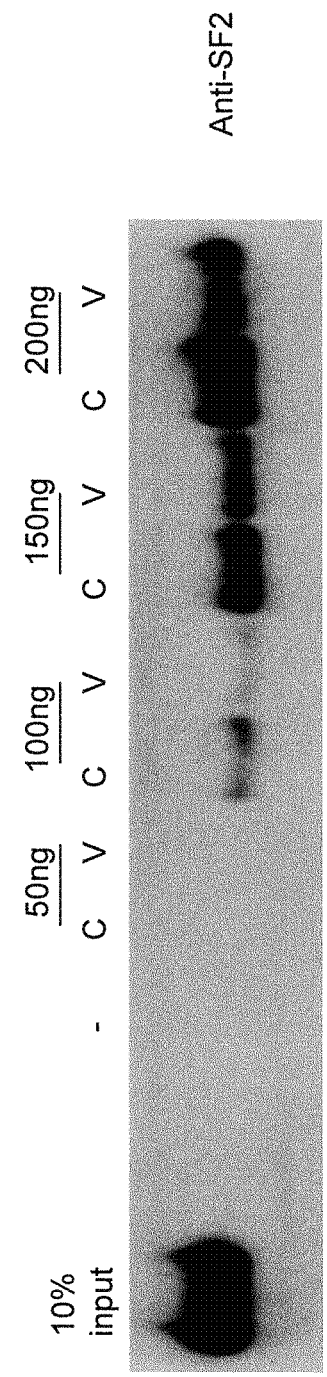
FIG. 16 depicts in vitro binding assay using biotin-labeled RNA oilgonucleotides. In vitro binding assay was performed by incubating the 293T cellular lysates with different amount of the biotinlyated RNA oligonucleotides, from 50 ng to 200 ng, containing either common allele "G" or variant allele "A". The biotinlyated RNA molecules were precipitated by streptavidin-agarose. The amount of SF2 bound to the oligonucleotides was examined by immunoblot using anti-SF2 antibody.

We performed an in vitro binding assay using the 293T cell lysate. The 293T cell lysates was incubated with different amount of the biotinlyated RNA oligonucleotides, from 50 ng to 200 ng, containing either common allele "G" or variant allele "A". The biotinlyated RNA molecules were precipitated by streptavidin-agarose. The amount of SF2 bound to the oligonucleotides was examined by immunoblot using anti-SF2 antibody. As shown in FIG. 16, the SF2 protein bound weaker to the variant allele's (rs11209026, 1142A) oligonucleotide than the common allele's (1142G) oligonucleotide (FIG. 16).

C) Competition Binding Assay

Figure 17:
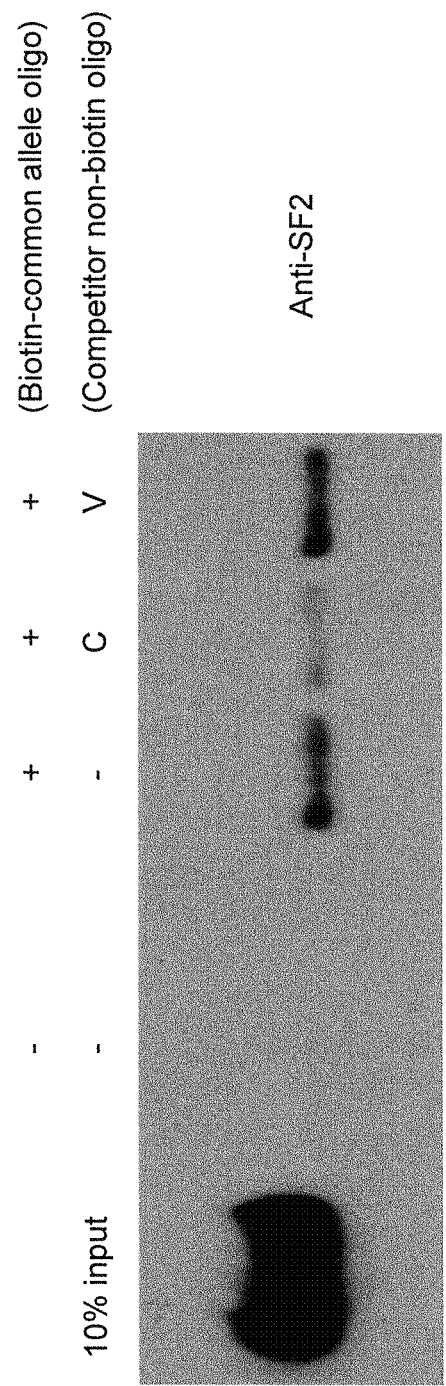
FIG. 17 depicts the competitive in vitro binding assay. 293T cellular lysates were incubated with 100 ng biotinlyated RNA oligonucleotides carrying the common allele "G". Non-biotinlyated competitor RNA oligonucleotides (100 ng), either common allele "G" or variant allele "A", were also added to the mixture. The biotinlyated RNA molecules were precipitated by streptavidin-agarose. The amount of SF2 bound to the oligonucleoties was examined by immunoblot using anti-SF2 antibody.
Figure 18A:
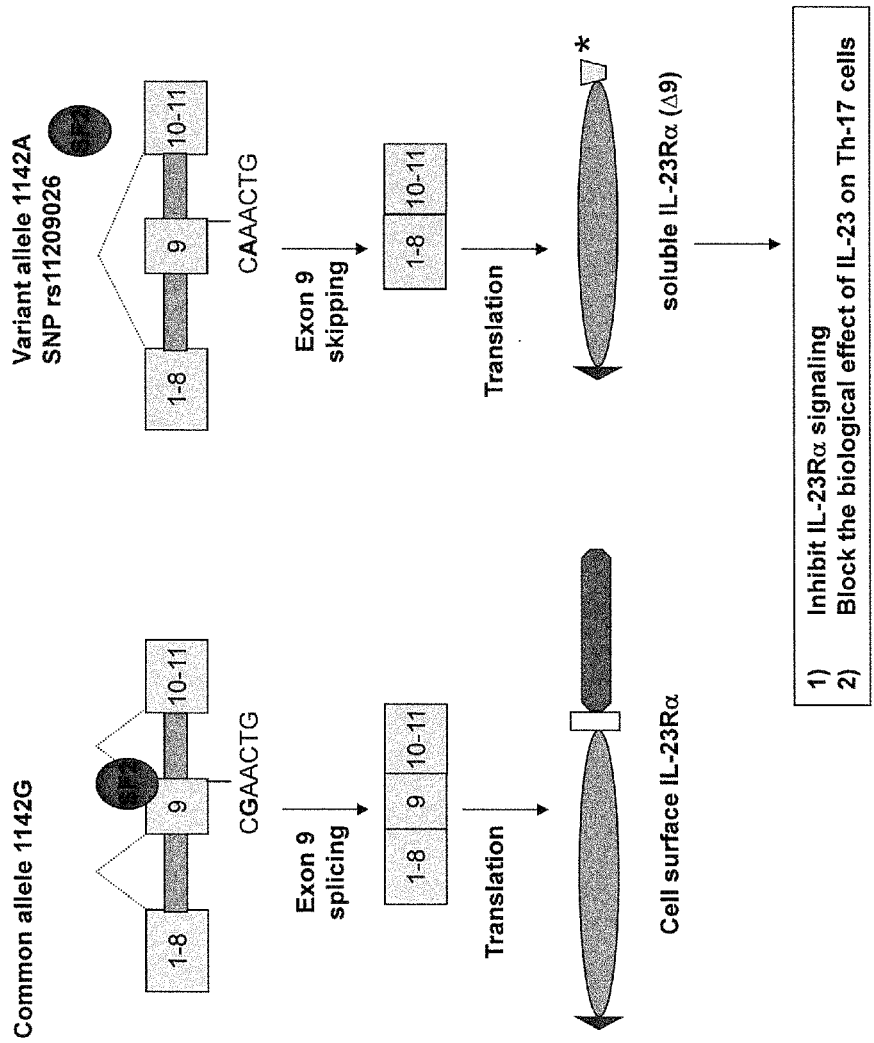
FIG. 18A depicts the summary of the function of two alleles on the IL-23Rα RNA splicing. IL-23Rα gene containing the common allele "G" is effectively bound by the SF2 (Splice enhancer) for proper exon 9 splicing. Translation of this gene product with the inclusion of exon 9 results in the expression of cell surface IL-23Rα. However, IL-23Rα gene containing the variant allele "A" failed to recruit the SF2 on the exon 9 during pre-mRNA splicing, which results in exon 9 skipping. Translation of mRNA transcription with exon 9 deletion results in the expression of soluble IL-23Rα(Δ9). This Δ9 protein contains almost the entire extracellular domain with a novel amino acid sequence at the C-terminus. The novel sequence was illustrated in the figure.

In order to confirm our observation obtained from the in vitro binding assay, we performed the competition binding asasy. The nonbiotinlyated RNA oligonucleotides were used as competitors. 293T cellular lysates were incubated with 100 ng biotinlyated RNA oligonucleotides carrying the common allele "G". Non-biotinlyated competitor RNA oligonucleotides (100 ng), either common allele "G" or variant allele "A", were also added to the mixture. The biotinlyated RNA molecules were precipitated by streptavidin-agarose. The amount of SF2 bound to the oligonucleotides in the precipitates was examined by immunoblot using anti-SF2 antibody (FIG. 17). The common allele's oligonucleotide reduced the amount of SF2 being pulled down in the assay. In contrast, the variant allele's oligonucleotide failed to compete. These results showed that variant allele "A" reduced the binding affinity of SF2 on exon 9 of IL-23Rα pre-mRNA. During mRNA splicing, exon 9 is skipped and the expression of Δ9 mRNA is increased (due to reduce efficiency on exon 9 splicing). As a result, soluble IL-23Rα protein is expressed (FIG. 18).

Figure 18B:
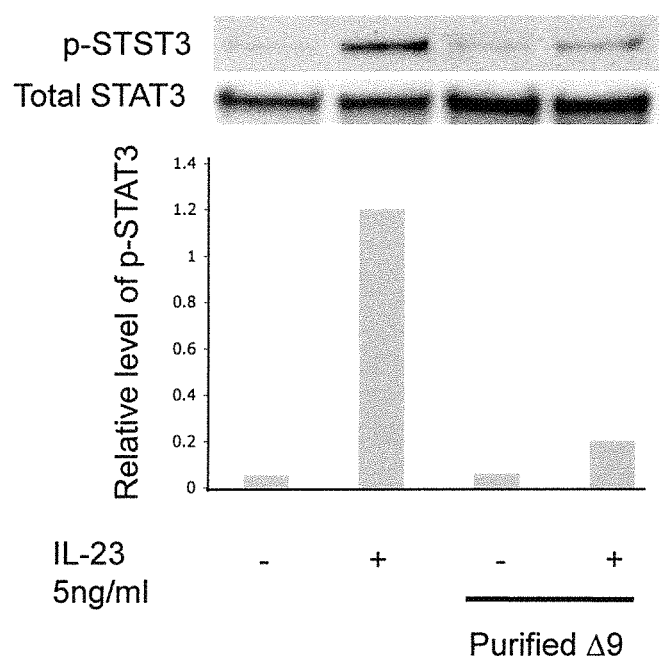
FIG. 18B depicts the inhibition of purified Δ9 protein on STAT3 activation induced by IL-23 in the human leukocytes. The human leukocytes were cultured in the RPMI medium and stimulated with 5 ng/mL IL-23 in the presence or absence of the purified recombinant Δ9 protein (500 ng/mL). Immunoblots were performed using p-STAT3 and total-STAT3 antibodies. Relative level of p-STAT3 was illustrated in the bar chart. Purified recombinant Δ9 protein significantly inhibited the STAT3 activation upon IL-23 stimulation.

To examine the function of Δ9, we purified recombinant Δ9 protein from the secreted source to apparent homogeneity. This purified Δ9 inhibited IL-23-induced STAT3 phosphorylation (FIG. 18B). Thus, Δ9 negatively regulates IL-23 signaling in human leukocytes.

Figure 18C:
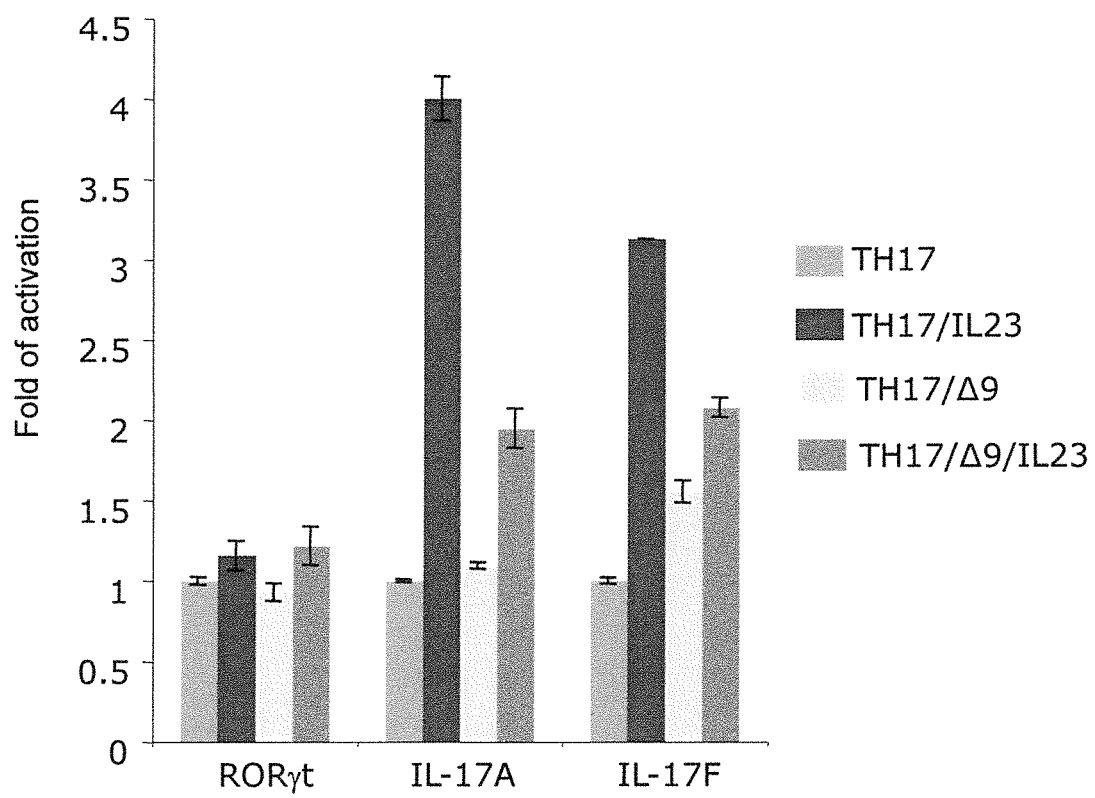
FIG. 18C depicts the ability of Δ9 to block the effect of IL-23 in enhancing the expression of IL-17A and IL-17F during the differentiation of CD4+ naïve T cells into Th17 cells.

We purified human CD3+CD4+CD45RA+ cells ("naive CD4+ T-cells") by negative selection (using magnetic beads coupled with specific bound antibodies against the cell surface markers. We differentiated the isolated cells to Th17 cells in vitro by stimulating the cells with anti-CD3/CD28 coated microbeads ("beads") in the presence of a cytokine cocktail comprising IL-1β, IL-6 and TGF-β for two days, at which point medium, IL-23, Δ9 or IL-23+Δ9 were added. Incubation continued for a further two days, whereupon cells were harvested for RNA. Terminal maturation of the Th17 phenotype by IL-23 was demonstrated by the enhanced expression of IL-17A, IL-17F mRNA in the presence of IL-23 (FIG. 18C); as expected, RORγt was not elevated by the addition of IL-23 to the Th17 cocktail, reaffirming that IL-23 is not a human Th17 cell differentiation factor. Addition of Δ9 alone to the Th17 cocktail failed to induce the mRNA expression of IL-17A or IL-17F, confirming its lack of stimulatory activity (FIG. 18C). FIG. 18C depicts that when IL-23 was added in the presence of Δ9, maturation of Th17 cells to an active phenotype was greatly reduced; mRNA expression of both IL-17A and IL-17F being significantly diminished.

Example 10 Anti-Sense Oliqonucleotides (AONs) Induces Exon 9 Skipping

We tested the hypothesis that SNP results in exon 9 skipping and thus increases the expression of soluble IL-23Rα protein (i.e., Δ9). In this study, we designed anti-sense oligonucleotides (AONs) and see if these AONs could mimic the effects of SNP rs11209026 during exon 9 splicing. The AON is an RNA oligonucleotide that is complementary to the end of exon 9 and the beginning of intron 10 (FIG. 19). Our designed AONs block the SF2 binding site on exon 9 and the 5' splice donor site on intron 9 to induce exon 9 skipping.

A) Mini-Gene (mRNA)

In order to examine the effects of AONs on exon 9 splicing, mini-gene was co-transfected with AONs into the 293T cells by Lipofectamine 200 (Invitrogen). RNA was prepared after 24 hours of transfection using RNA miniprep kit (Stratagene). The isolated RNA was reverse transcribed into cDNA using AffinityScript cDNA synthesis kit (Stratagene). Expressions of exon 8/9/10 and exon 8/10 were measured by RT-PCR using the primers as described above in Example 2. We found that AONs increased expression of exon 8/10 transcripts (FIG. 19). Thus, AONs induce exon 9 skipping in a dose-dependent manner.

B) BAC Containing IL-23Rα Gene (mRNA)

In order to confirm the observed AONs effects on exon 9 splicing using the mini-gene, BAC containing IL-23Rα gene was cotransfected with AONs into the 293T cells by Lipofectamine 2000 (Invitrogen). RNA was prepared after 24 hours of transfection using RNA miniprep kit (Stratagene). The isolated RNA was reverse transcribed into cDNA using AffinityScript cDNA synthesis kit (Stratagene). Expressions of total IL-23Rα and mRNA transcript missing exon 9 (Δ9) were measured by qRT-PCR using the primers as described in the following.

Total IL-23Rα:

```
        Forward primer (F3):
                                      (SEQ ID NO: 29)
        AGAACTGCCAACCAAGGAAA Reverse primer (R4):
                                      (SEQ ID NO: 30)
        TAGGTGAGCTTCCCAGCATT

Δ9:

(SEQ ID NO: 23)
  Forward primer (F1): GGCACCTTACTTCTGGATTAAAAG (SEQ ID NO: 28)
    Reverse primer (Ex11R): AGGACCTGCTCACTGGAATTA
```

Figure 20:
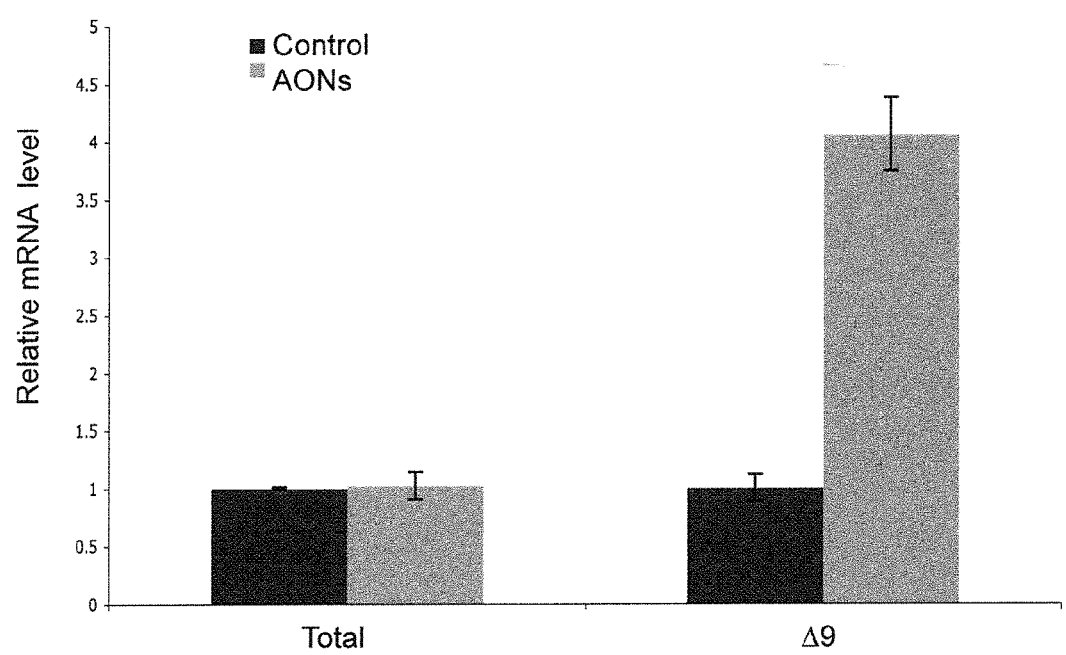
FIG. 20 depicts the effect of AONs on the exon 9 skipping using the BAC clone. 293T cells were co-transfected with the BAC DNA and control or IL-23Rαspecific AONs. RNA was prepared 24 hours posttransfection and was reverse transcribed into cDNA. The mRNA levels of total IL-23Rα and Δ9 variant were measured by real-time qRT-PCR.

AONs had no effect on the total expression level of IL-23Rα (FIG. 20); however, AONs increased expression of Δ9 transcripts. Therefore, the AONs could induce exon 9 skipping when the transcription of IL-23Rα gene is controlled by its own regulatory elements (present in the BAC clone).

C) BAC Containing IL-23Rα Gene (Protein by ELISA)

Figure 21:
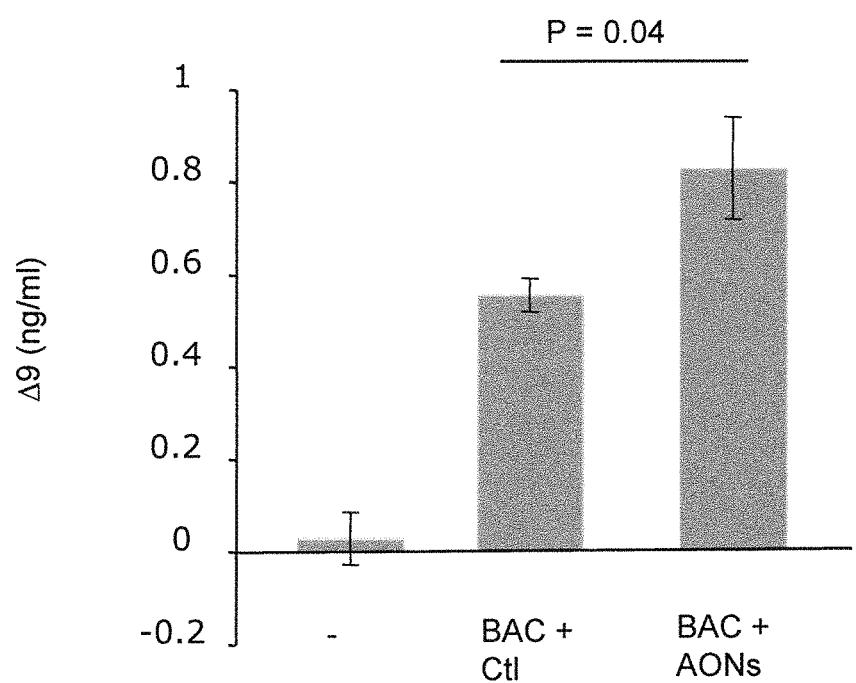
FIG. 21 depicts the ELISA experiment to measure the level of soluble IL-23Rα (Δ9) upon AONs treatment. The 293T cells were transfected with BAC DNA and AONs. The culture media were harvested 48 hours post-transfection. The culture medium from non-transfected 293T cells was used as control.

We examined if the AONs increase the expression of Δ9 mRNA and also induced the expression of Δ9 proteins. To do so, we performed an ELISA experiment (FIG. 21). 293T cells were transfected with empty vector, BAC+ control AONs or BAC+AONs. The culture media were harvested 48 hours post-transfection. We performed the Sandwich ELISA to measure the amount of Δ9 in these culture media (FIG. 21). No Δ9 was detected when the 293T cells were transfected with empty vector. In contrast, 293T cells transfected with BAC+ control AONs and BAC+AONs showed ~0.5 ng/ml and ~0.8 ng/ml Δ9, respectively. These results clearly demonstrated that the AONs induced the expression of Δ9 protein.

D) Endogenous IL-23Rα (Human Leukocytes)

In addition to the over-expression studies, AONs were transfected into human PBMCs, which naturally expressed IL-23Rα, by Amaxa Nculeofector Transfection kit (Amaxa). RNA was prepared after 24 hours of transfection using RNA miniprep kit (Stratagene). The isolated RNA was reverse transcribed into cDNA using AffinityScript cDNA synthesis kit (Stratagene). Expressions of total IL-23Rα and mRNA transcript missing exon 9 (Δ9) were measured by qRT-PCR using the primers as described in Example 10.

Figure 22:
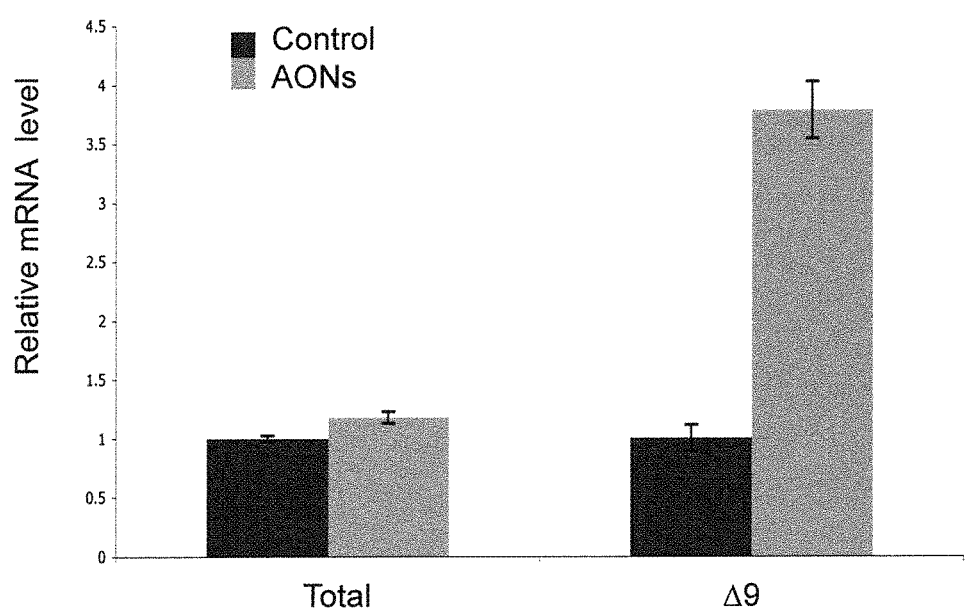
FIG. 22 depicts the effect of AONs on the exon 9 skipping in the human leukocytes. Human Leukocytes were transfected with the control or IL-23Rαspecific AONs (100 pmole). RNA was prepared 24 hours posttransfection and was reverse transcribed into cDNA. The mRNA levels of total IL-23Rα and Δ9 variant were measure by real-time qRT-PCR.

AONs had no effect on the total expression level of IL-23Rα. In contrast, the AONs increased expression of Δ9 transcripts by around 4 fold (FIG. 22). AONs also dose-dependently induced expression of Δ9 (FIG. 23 TOP: qRT-PCR and Bottom: RT-PCR).

Figure 24:
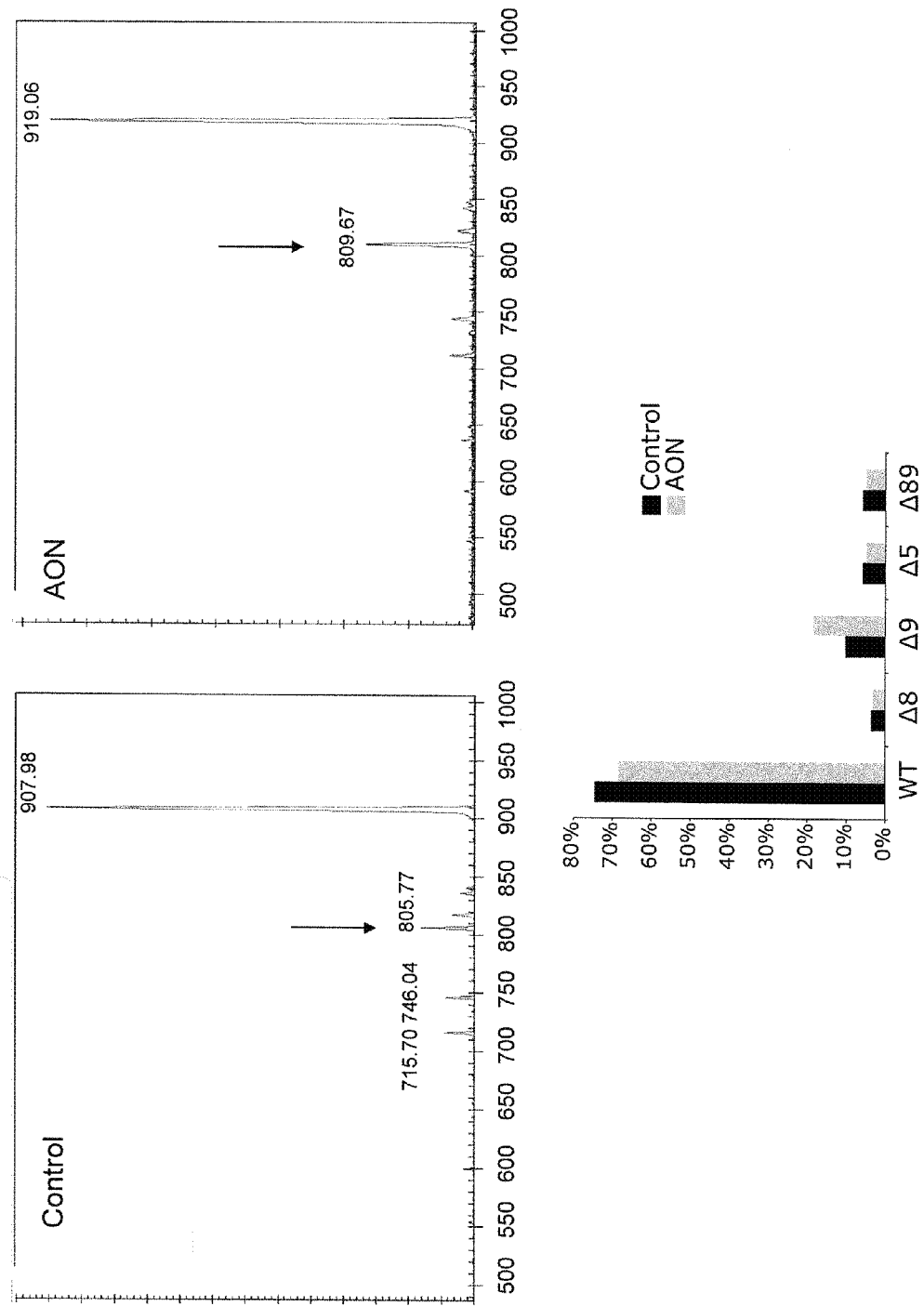
FIG. 24 depicts the fragment analysis on the expression profile of IL-23Rα and its variants including Δ8, Δ9, Δ5 and Δ89 in the human leukocytes treated with AONs. Peaks were assigned to corresponding IL23Rαspliced variants based on their size. The percentage expression of the wild-type and 4 measurable variants is shown.

Example 11 Anti-Sense Oligonucleotides (AONs) Specifically Induces Expression of Δ9 but not Other Splice Variants In order to examine the specific effect of AONs on Δ9 induction, we performed a Fragment Analysis to semi-quantitatively measure the mRNA expression level of these IL-23Rα isoforms in a single PCR reaction using a Beckman CEQ8000 machine (FIG. 24). We compared quantitatively the individual human IL23Rαsplice variant forms relative to the full-length (wild-type, "wt") IL-23Rα form (FIG. 24). Human leukocytes were isolated and used as a cellular model to examine the expression of different IL-23Rα isoforms. 100 pmole of AONs was transfected into the human leuokocytes by Amaxa Nculeofector Transfection kit (Amaxa). RNA was extracted (using Stratagene RNA miniprep kits) from the transfected leukocytes 24 hours post-transfection and its concentration was measured in Nano-drop. Two (2) micrograms (μg) of RNA was reversely transcribed into cDNA. A pair of gene specific IL-23R primers (P5) and (P6), which was fluorescent labeled (P6-D3), was designed to amplify IL-23R isoforms by PCR (see "Materials & Methods" section, infra, for primer sequence information). Amplified products were denatured, run on the CEQ8000 machine and separated by size. Peaks were assigned to the corresponding variants based on their size. The fluorescent signal represented the level of expression (FIG. 24). AONs specifically induced the expression of Δ9 without altering the expression of other variants.

Figure 25:
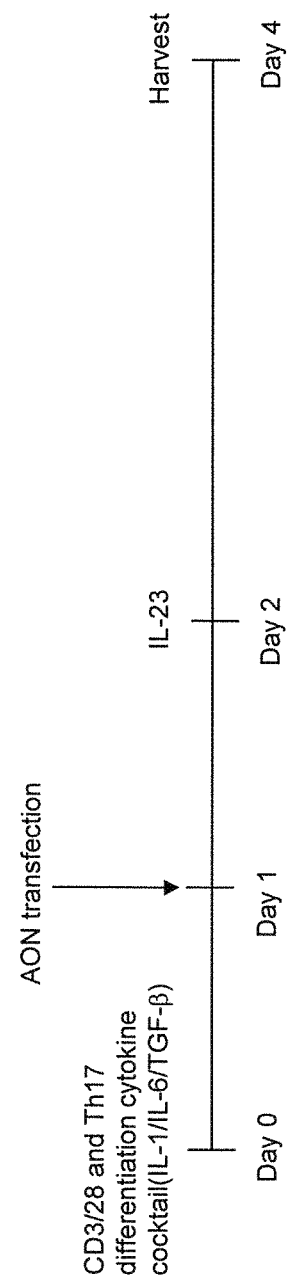
FIG. 25 depicts the in vitro differentiation protocol of Th17 cell. CD4+ human T cells were prepared by negative enrichment (Stemcell Technologies, Vancouver). These cells were differentiated to Th17 cells as shown. AONs were transfected into the stimulated T cells on day 1. One day after transfection, IL-23 was added to the cells. In vitro differentiated Th17 cells were harvested on day 4.

Example 12 Anti-Sense Oligonucleotides (AONs) Inhibits the Maturation of Th17 Cells Th17 cells play an important role in Crohn's disease and IL-23R signaling is essential for terminal maturation of Th17 cells. The CD-protective variant allele "A" induced exon 9 skipping to increase the expression of soluble IL-23Rα (i.e., Δ9). In a previous study, we showed that Δ9 protein not only inhibits IL-23 signaling but also blocks the functional maturation of human Th17 cells. In Example 11, we showed that AONs, which can mimic the effect of rs11209026 on exon 9 splicing, specifically induced the expression of Δ9 mRNA and protein. Therefore, we hypothesized that the AONs may negatively regulate the terminal maturation of Th17 cells. CD4+ T cells were purified using kit provided by StemCell Technology. The enriched CD4+ T cells were differentiated into $T_H$-17 cell under the influence of CD3/28 and a $T_H$-17 differentiation cytokine cocktail composing IL-1, TGF-β and IL-6 (FIG. 25). AONs were transfected into the differentiating T cells on Day 1 by using Amaxa Nculeofector Transfection kit (Amaxa). IL-23 cytokine was added to the differentiation reaction on Day 2. The RNA was harvested on Day 4 (FIG. 25). The expression levels of total IL-23Rα, Δ9, IL-17A and IL-17F were measured by qRT-PCR using the following primers.

Total:

```
                                      (SEQ ID NO: 29)
    Forward primer (F3): AGAACTGCCAACCAAGGAAA (SEQ ID NO: 30)
    Reverse primer (R4): TAGGTGAGCTTCCCAGCATT
```

Δ9:

```
                                      (SEQ ID NO: 23)
    Forward primer (F1): GGCACCTTACTTCTGGATTAAAAG (SEQ ID NO: 28)
    Reverse primer (Ex11R): AGGACCTGCTCACTGGAATTA
```

IL-17A:

```
                                      (SEQ ID NO: 31)
    Forward primer: CTGGGAAGACCTCATTGGTGTCAC (SEQ ID NO: 32)
    Reverse primer: CGGTTATGGATGTTCAGGTTGACC
```

IL-17F:

```
                                      (SEQ ID NO: 33)
    Forward primer: CCTCCCCCTGGAATTACACTGTC (SEQ ID NO: 34)
    Reverse primer: CAGGGTCTCTTGCTGGATGGG
```

Figure 26:
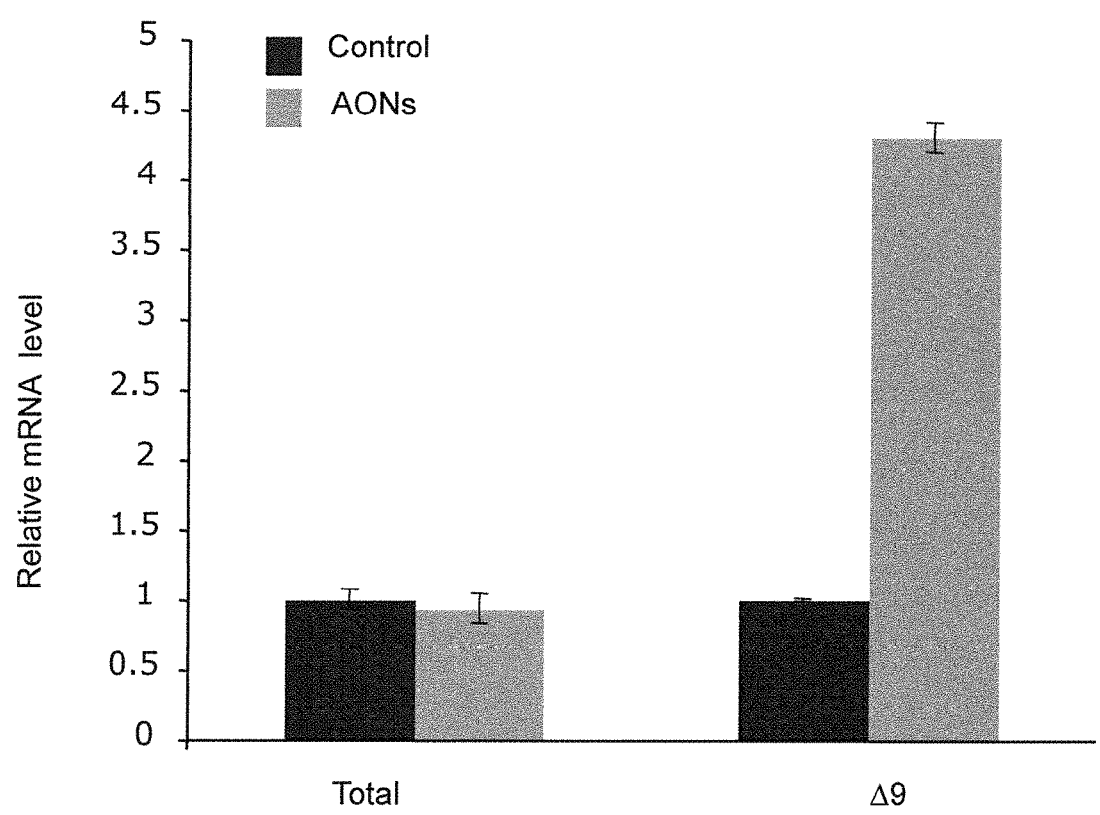
FIG. 26 depicts the induction of Δ9 mRNA by AONs in the in vitro differentiated Th17 cells. mRNA was extracted from the differentiated cells and was reverse transcribed into cDNA. Successful induction of exon 9 skipping was measured by the expression level of its Δ9 variant by real-time qRT-PCR. Total IL-23Rα level was also measured.

AONs (but not control oligonucleotides) induced the expression of Δ9 without altering the expression level of total IL-23Rα in the in vitro differentiated Th17 cells (FIG. 26).

Figure 27:
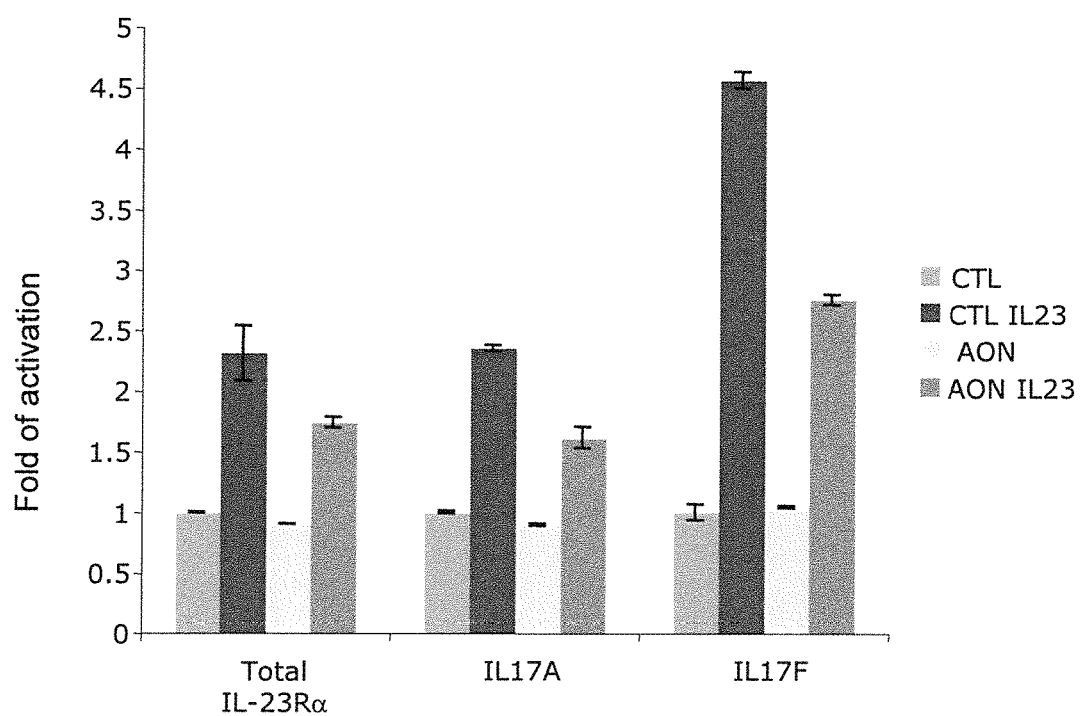
FIG. 27 depicts the effect of AONs on Th17 differentiation. mRNA levels of IL-23Rα, IL-17A and IL-17F in the in vitro differentiated Th17 cells were quantitated by real-time qRT-PCR. IL-23 was required for the induction of IL-23Rα, IL-17A and IL-17F mRNA expression. Transfection of AONs blocked the induction of IL-23Rα, IL-17A & F by IL-23.

Maturation of Th17 cells was measured by the expression levels of IL-17A and IL-17F cytokines. IL-23 stimulated IL-17A and IL-17F expressions by ~2.5 and ~4 fold respectively. In contrast, differentiated cells treated with AONs greatly reduced the stimulating effect of IL-23 on IL-17A and IL-17F expressions (FIG. 27). Thus, AONs induced the expression of soluble IL-23Rα (Δ9) to block the function of IL-23 cytokine on the maturation of Th17 cells.

Example 13 Anti-Sense Oligonucleotides (AONs) Against Exon 9 Induces Exon 9 Skipping In Example 10, we used AON1 (FIG. 28) targeting the end of exon 9 (i.e., SF2 binding site) and the beginning of intron 10 and found that it induced exon 9 skipping. In this study, we designed additional AONs to examine the effects of varying lengths (i.e., 22nts, 18nts and 15nts) and targeting positions (i.e., intron 8, exon 9 and intron 9). The nucleotide sequence for the AONs used in this study (i.e., SEQ ID NOs: 10, 11, 12, 13, 14, 15, 16, 17, 18 and 19) is listed as follows.

| Name | Nucleotide Sequence | SEQ ID NO: |
|---|---|---|
| AON1 | ACCUACCCAGUUCG-GAAUGAUC | 10 |
| (Control) | UAUCUGGACUAGUACGAC-UUAC | 11 |
| AON1.1 | CUACCCAGUUCGGAAUGA | 12 |
| AON1.2 | UACCCAGUUCGGAAU | 13 |
| AON2 | ATGTCTCCTCTGTT-GTCTAATG | 14 |
| AON3 | TAACAGCAAAGACGATCAT-TCC | 15 |
| AON4 | GAAACAACTTTTGTTT-GAGAA | 16 |
| AON5 | GTTTTTCCAGAGTGCA-CAACTA | 17 |
| AON6 | ACAACTGAAAT-GACTAAATTTT | 18 |
| AON7 | AAAACGCCGTGTAG-TAAAGGAG | 19 |

In order to examine the effects of AONs on exon 9 splicing mini-gene was co-transfected with AONs (50 pmole) into the 293T cells by Lipofectamine 2000 (Invitrogen). RNA was prepared after 24 hours of transfection using RNA miniprep kit (Stratagene). The isolated RNA was reverse transcribed into cDNA using AffinityScript cDNA synthesis kit (Stratagene). Expressions of exon 8/10 were measured by qRT-PCR using the primers as described above in Example 2.

There is no difference in the ability of inducing exon 9 skipping when different lengths of AONs (i.e., AON1=22nts, AON1.1=18nts and AON1.2=15nts) were used. All of the tested AONs were used at a concentration of 50 pmole. All of tested AONs increased expression of exon 8/10 transcripts (FIG. 29). In addition, all the tested AONs targeting the exon 9 (i.e., AON1, AON1.1, AON1.2, AON2 and AON3) showed the same ability to induce exon 9 skipping (i.e., ~30 fold increased in Exon 8/10 mRNA transcript). In contrast, AONs targeting to the intron (i.e., AON4, AON5 and AON6) failed to induce the exon 9 skipping. AON7, which targeted the intron 9 (FIG. 28), weakly induced the exon 9 skipping (i.e., ~3 fold increase in Exon 8/10 mRNA transcript) (FIG. 29).

Materials and Methods

Construction of Mini-Gene Plasmids

RP11-684P13 BAC clone carrying 138 kb of human chromosome 1 was purchased from Invitrogen. This fragment of chromosome 1 contains 33 kb of DNA sequence upstream of transcription start, all the exonic and intronic sequences, and 12 kb DNA sequence downstream of transcription stop. Common allele mini-gene plasmid as illustrated in FIG. 1B was constructed by the PCR using the following primer pairs.

Exon 8/Intron 8 Fragment:

```
                                        (SEQ ID NO. 35)
8F: AAGCTAGCTCCCCAGGTCACATCAAAAG (SEQ ID NO. 36)
8R: AAGGTACCAAAATTAGCTGGGCGTGATG
```

Intron 8/Exon9/Intron10 Fragment:

```
                                        (SEQ ID NO. 37)
9F: AAGGTACCCCTGTGTCAGACAAGCCAAA (SEQ ID NO. 38)
9R: AAGGATCCAAGGCAACCCTGGAGTCTTT
```

Intron 10/Exon10 Fragment:

```
                                        (SEQ ID NO. 39)
9F: AAGGATCCTCTGTTGCCCAGAGTGAGTG (SEQ ID NO. 40)
9R: AACTCGAGTTCACAACATTGCTGTTTTCA
```

The PCR fragments were sub-cloned into mammalian expression vector, pCDNA3.1. The mini-gene plasmid was sequence verified. PCR mediated site directed mutagenesis was employed to change the common allele sequence "G" into variant allele sequence "A".

Construction of SF2 and SRP40 Expression Plasmids

Expression plasmids of SF2 and SRp40 were constructed by amplifying SF2 and SRp40 coding sequences using the following primers.

```
                                        (SEQ ID NO. 24)
SF2 F: ACAAGCTTGCCACCATGTCGGGAGGTGGTGTGATT (SEQ ID NO. 25)
SF2 R: ATCTCGAGTTATGTACGAGAGCGAGATCT (SEQ ID NO. 26)
SRP40 F: ACAAGCTTGCCACCATGAGTGGCTGTCGGGTATTC (SEQ ID NO. 27)
SRP40 R: ATCTCGAGTTAATTGCCACTGTCAACTGA
```

The PCR fragments were subcloned into mammalian expression vector, pcDNA3.1. The expression plasmids were sequence verified.

AON-Mediated Exon Skipping

The RNA anti-sense oilgonucleotide (AON), ACCUAC-CCAGUUCGGAAUGAUC (SEQ ID NO. 10), was synthesized by Integrated DNA Technolgies. The phosphodiester bond was modified by replacing one of the non-bridging oxygen by sulfur. The RNA AON containing the sulfur-substituted oligonucleotides has a phosphorothioate linkage and 2'-O-Methyl RNA bases. The AON was transfected into the 293T cells and primary human cells (such as CD4$^+$ T cells and PBMCs) using lipofectamine 2000 (Invitrogen) and human T-cells transfection kit (Amaxa).

In Vitro Th-17 Cell Differentiation

CD4$^+$ T cells were negatively enriched using human CD4$^+$ T cells enrichment kit (StemCell Technologies). 1×10$^6$ cells/ml of CD4$^+$ naive T cells were differentiated into Th-17 cells under Th-17 culture condition (CD3/28 beads, 10 ng/ml of IL-18, 10 ng/ml of IL-6, 10 ng/ml of IL-23 and 1 ng/ml of TGF-β) for 5 days. All cytokines were purchased from Humanzyme. The CD3/28 beads were used according to the manufacture's instructions (Miltenyi Biotec). The differentiated cells were subjected to RNA extraction and real-time PCR to analyze gene expression.

Real-Time PCR

Naive T-cells were differentiated under Th-17 condition for 5 days. Differentiated cells were collected and RNA was extracted by Trizol (Invitrogen). RNA was reverse transcribed into cDNA by AffinityScript QPCR cDNA Synthesis Kit (Stratagene) according to the manufacturer's instructions. The real-time PCR was performed using Brilliant II SYBR Green QPCR Master Mix (Stratagene). The following primers were used in the study:

IL-17A:

```
                                      (SEQ ID NO. 31)
F5'CTGGGAAGACCTCATTGGTGTCAC3', (SEC) ID NO. 32)
R5'CGGTTATGGATGTTCAGGTTGACC3';
```

IL-17F:

```
                                      (SEQ ID NO. 33)
F5'CCTCCCCCTGGAATTACACTGTC3', (SEQ ID NO. 34)
R5'CAGGGTCTCTTGCTGGATGGG3';
```

GAPDH:

```
                                      (SEQ ID NO. 47)
F5'GAGTCAACGGATTTGGTCGT3', (SEQ ID NO. 48)
R5'GACAAGCTTCCCGTTCTCAG3'.
```

SF2 RNA Interference Experiment 293T cells were transfected with 20 pmoles of anti-sense SF2 RNA (Dharmacon). Transfected Cells were collected, washed in PBS and lysed in ProteoJET mammalian cell lysis reagent (Fermentas) with protease and phosphatase inhibitors (Sigma) 48 hours post-transfection. Lysates were centrifuged and supernatants were prepared for SDS-PAGE by addition of sample loading buffer (Bio-Rad). Lysates were subjected to 4-12% PAGE (Bio-Rad) and transferred to Immun-Blot PVDF membrane (BioRad) per manufacturer's recommendations. Membranes were blocked in 5% milk/TPBT at room temperature for 1 hour. Membranes were first probed with antibodies against SF2 (Santa Cruz), and then stripped and reprobed for Actin (Santa Cruz).

Fragment Analysis

Total RNA was isolated from PBMCs by 'Absolutely RNA' miniprep kit (Stratagene) following the manufacturer's instructions. Purified RNA was reverse-transcribed into cDNA using AffinityScript cDNA synthesis kit (Stratagene). PCR was carried out using 'Expand Long Template Enzyme' mix (Roche Applied Science) with forward primer (P5) 5'AATGCTGGGAAGCTCACCTACATA3' (SEQ ID NO. 49) and reverse primer 5'D3-GCTTGTGT-TCTGGGATGAAGATTTC3' (P6-D3) (SEQ ID NO. 50), which was fluorescent labeled with D3 dye. The amplified product was then analyzed in the Beckman CEQ8000 using Fragment Analysis Program. 1 µl (5%) of PCR product was denatured in 39 µl of SLS buffer (Beckman) containing DNA standard size markers. Two DNA standard size markers, DNA size standard marker kit 600 (0.5 µl/reaction) (Beckman) and custom made D1 labeled 600-1200 size marker (1 µl/reaction) (Bioventures, Inc) were used in to cover the DNA size from 60 to 1200 nucleotides.

Isolation and Culture of Human PBMCs and Immune Cells

Peripheral blood mononuclear cells were isolated from heparinized whole venous blood of healthy donors by density gradient centrifugation using Ficoll-Paque (Sigma-Aldrich, St Louis, Mo., USA) according to the manufacture's instructions. Blood was purchased as anonymous buffy coats from New Jersey blood transfusion service with no donor identifying details. Isolated PBMCs were maintained in RPMI-1640 medium (Invitrogen-Gibco, Carlsband, Calif., USA) supplemented with 10% heat-inactivated fetal bovine serum (Invitrogen-Gibco) and 1 mM glutamine (Invitrogen-Gibco).

In Vitro Binding Assay

Biotinlyated RNA oligonucleotides containing either common allele "G" or variant allele "A" were used.

Common Allele (G):

```
                                      (SEQ ID NO. 44)
Biotin-ATCATTCCGAACTGGGTAGGT
```

Variant Allele (A):

```
                                      (SEQ ID NO. 45)
Biotin-ATCATTCCAAACTGGGTAGGT
```

The RNA oligonucleotides were incubated with either whole cell lysates from the 293T cells or SF2 recombinant protein for 1 hour at room temperature. The biotinlyated RNA molecules were then precipitated by streptavidin agarose (Pierce). The precipitates were extensively washed with phosphate buffered saline pH=7.4. The amount of SF2 bound to the RNA oligonucleotides was assayed by immunoblot using anti-SF2 antibody (Santa Cruz).

Enzyme-Linked Immunosorbent Assay (ELISA)

Sandwich ELISA was developed using 5 µg/ml of mouse anti-hIL-23Rα(R&D) as capture antibody and 1.6 µg/ml of Goat biotinlyated antiIL-23Rα (R&D) as detection antibody. Capture antibody was first coated on the microtiter plate using 50 mM of bicarbonate buffer (pH=9.6) at 4° C. overnight. The plate was then blocked with 10% FBS/TBST at room temperature for 2 hours. Samples were added to the well and incubated at 4° C. overnight. Detection antibody in TBST was added to the wells and incubated at room temperature for 2 hours. The plate was extensively washed with TBST during each change. The immuno-complex was detected by addition of Streptavidin-HRP (R&D) and TMB substrate (eBioscience). The plate was read at O.D.450 nm.

While the present invention has been described in connection with specific embodiments thereof, it will be understood that it is capable of further modifications and this application is intended to cover any variations of the invention thereof. One of skill in the art will recognize that various modifications may be made to the embodiments described herein without departing from the spirit and scope of the invention, which is defined by the appended claims. All the references and patents cited in this application are incorporated by reference in their entirety.

REFERENCES

1. Dubinsky, M. C. et al. IL-23 receptor (IL-23R) gene protect against pediatric Crohn's disease. Inflamm Bowel Dis 13, 511-515 (2007).

2. Duerr, R. H. et al. A genome-wide association study identifies IL23R as an inflammatory bowel disease gene. Science 314, 1461-1463 (2006).
3. Newman, W. G., Zhang, Q., Liu, X., Amos, C. I. & Siminovitch, K. A. Genetic variants in IL-23R and ATG16L1 independently predispose to increased susceptibility to Crohn's disease in Canadian population. J Clin Gastroenterol 43, 444-447 (2009).
4. McKenzie, B. S., Kastelein, R. A. & Cua, D. J. Understanding the IL-23-1L-17 immune pathway. Trends Immunol 27, 17-23 (2006).
5. de Paus, R. A., van de Wetering, D., van Dissel, J. T. & van de Vosse, E. IL-23 and IL-12 responses in activated human T cells retrovirally transduced with IL-23 receptor variants. Mol Immunol 45, 3889-3895 (2008).
6. Kan, S. H., Mancini, G. & Gallagher, G. Identification and characterization of multiple splice forms of the human interleukin-23 receptor alpha chain in mitogen-activated leukocytes. Genes Immun 9, 631-639 (2008).
7. Mancini, G., Kan, S. H. & Gallagher, G. A novel insertion variant of the human IL-23 receptor-alpha chain transcript. Genes Immun 9, 566-569 (2008).
8. Cooper, T. A. & Mattox, W. The regulation of splice-site selection, and its role in human disease. Am J Hum Genet 61, 259-266 (1997).
9. Watakabe, A., Tanaka, K. & Shimura, Y. The role of exon sequences in splice site selection. Genes Dev 7, 407-418 (1993).
10. Woodley, L. & Valcarcel, J. Regulation of alternative pre-mRNA splicing. Brief Funct Genomic Proteomic 1, 266-277 (2002).
11. Lin, S. & Fu, X. D. SR proteins and related factors in alternative splicing. Adv Exp Med Biol 623, 107-122 (2007).
12. Shiga, N. et al. Disruption of the splicing enhancer sequence within exon 27 of the dystrophin gene by a nonsense mutation induces partial skipping of the exon and is responsible for Becker muscular dystrophy. J Clin Invest 100, 2204-2210 (1997).
13. Vuillaumier-Barrot, S. et al. Characterization of the 415G>A (E139K) PMM2 mutation in carbohydrate-deficient glycoprotein syndrome type Ia disrupting a splicing enhancer resulting in exon 5 skipping. Hum Mutat 14, 543-544 (1999).
14. Long, J. C. & Caceres, J. F. The SR protein family of splicing factors: master regulators of gene expression. Biochem J 417, 15-27 (2009).
15. Cua, D. J. et al. Interleukin-23 rather than interleukin-12 is the critical cytokine for autoimmune inflammation of the brain. Nature 421, 744-748 (2003).
16. Langrish, C. L. et al. IL-23 drives a pathogenic T cell population that induces autoimmune inflammation. J Exp Med 201, 233-240 (2005).

What is claimed is:

1. A method of producing a soluble truncated IL-23Rα protein, comprising the step of exposing an anti-sense RNA oligonucleotide to a mammalian cell,
   wherein said anti-sense RNA oligonucleotide is targeted against exon 9 of IL-23Rα gene to induce skipping of exon 9 in said mammalian cell, and is selected from the group consisting of SEQ ID NO: 10, SEQ ID NO: 12, SEQ ID NO: 13, SEQ ID NO: 14, and SEQ ID NO: 15, and
   wherein said anti-sense RNA oligonucleotide comprises a modified inter-nucleoside linkage.

2. The method of claim 1, wherein said modified inter-nucleoside linkage is a phosphorothioate linkage.

3. The method of claim 1, wherein said anti-sense oligonucleotide comprises a modified sugar moiety.

4. The method of claim 3, wherein said modified sugar moiety is 2'-O-methyl sugar moiety.

5. The method of claim 1, further comprising the step of quantifying said soluble truncated IL-23Rα protein after said exposing step.

6. The method of claim 5, wherein said soluble truncated IL-23Rα protein is quantified using an enzyme-linked immunosorbent assay (ELISA).

7. The method of claim 1, further comprising the step of quantifying mRNA of said soluble truncated IL-23Rα protein after said exposing step.

8. The method of claim 7, wherein said mRNA of said soluble truncated IL-23Rα protein is quantified using qRT-PCR.

9. The method of claim 1, where said mammalian cell is a peripheral blood mononuclear cell (PBMC), a CD4+ T cell, or a Th17 cell.

* * * * *